(12) United States Patent
Wu et al.

(10) Patent No.: US 11,753,363 B2
(45) Date of Patent: Sep. 12, 2023

(54) 13-OXIDIZED INGENOL DERIVATIVE AND USE THEREOF

(71) Applicant: Tianjin Pharmaceutical Da Ren Tang Group Corp., Ltd. Traditional Chinese Medicine Research Institute, Tianjin (CN)

(72) Inventors: Xiao Wu, Tianjin (CN); Qin Pan, Tianjin (CN); Yanyun Li, Tianjin (CN); Yu Yang, Tianjin (CN); Yuzhen Guan, Tianjin (CN); Xiaolei Wu, Tianjin (CN); Chuanteng Sun, Tianjin (CN); Yuan Wang, Tianjin (CN)

(73) Assignee: Tianjin Pharmaceutical Da Ren Tang Group Corp., Ltd. Traditional Chinese Medicine Research Institute, Tianjin (CN)

( * ) Notice: Subject to any disclaimer, the term of this patent is extended or adjusted under 35 U.S.C. 154(b) by 0 days.

(21) Appl. No.: 16/620,803

(22) PCT Filed: Jun. 7, 2018

(86) PCT No.: PCT/CN2018/090272
§ 371 (c)(1),
(2) Date: Dec. 9, 2019

(87) PCT Pub. No.: WO2018/224007
PCT Pub. Date: Dec. 13, 2018

(65) Prior Publication Data
US 2020/0140369 A1 May 7, 2020
US 2021/0147334 A9 May 20, 2021

(30) Foreign Application Priority Data
Jun. 9, 2017 (WO) ................ PCT/CN2017/087700

(51) Int. Cl.
| | | |
|---|---|---|
| C07C 69/013 | (2006.01) | |
| A61P 35/00 | (2006.01) | |
| C07C 69/608 | (2006.01) | |
| C07D 317/70 | (2006.01) | |
| C07D 319/08 | (2006.01) | |
| C07D 493/08 | (2006.01) | |
| C07D 317/18 | (2006.01) | |
| C07D 319/06 | (2006.01) | |
| C07C 69/533 | (2006.01) | |
| C07C 69/33 | (2006.01) | |
| C07D 261/18 | (2006.01) | |
| C07D 493/04 | (2006.01) | |

(52) U.S. Cl.
CPC ............ *C07C 69/013* (2013.01); *A61P 35/00* (2018.01); *C07C 69/608* (2013.01); *C07D 261/18* (2013.01); *C07D 317/70* (2013.01); *C07D 319/08* (2013.01); *C07D 493/04* (2013.01); *C07D 493/08* (2013.01); *C07C 2603/86* (2017.05)

(58) Field of Classification Search
CPC .. C07D 261/18; C07D 493/04; C07D 493/08; C07D 319/08; C07D 319/06; C07D 317/18; C07D 317/70; C07C 2603/86; C07C 69/533; C07C 69/608; C07C 69/013; C07C 69/33; A61P 35/00
See application file for complete search history.

(56) References Cited

U.S. PATENT DOCUMENTS

| | | |
|---|---|---|
| 2013/0177952 A1 | 7/2013 | Hogberg et al. |
| 2019/0083443 A1 | 3/2019 | Zhang et al. |

FOREIGN PATENT DOCUMENTS

| | | |
|---|---|---|
| CN | 103119016 A | 5/2013 |
| CN | 106928063 A | 7/2017 |
| JP | 08245379 A | 9/1996 |
| JP | 08245505 A | 9/1996 |
| WO | WO 2012/010172 A1 | 1/2012 |

OTHER PUBLICATIONS

Zhang et al., 2018, caplus an 2018:2347785.*
RN2053505-31-8, registry database compound, entry date Dec. 22, 2016.*
RN2102886-76-8, registry database compound, entry date Jul. 25, 2017.*
RN 2053505-28-3, registry database compound, Dec. 22, 2016.*
International Search Report and Written Opinion dated Sep. 6, 2018 in connection with PCT/CN2018/090272.
Abreu et al., Dual role of novel ingenol derivatives from Euphorbia tirucalli in HIV replication: inhibition of de novo infection and activation of viral LTR. PLoS One. May 14, 2014;9(5):e97257. doi: 10.1371/journal.pone.0097257. eCollection 2014.
Asada et al., Induction of thymocyte apoptosis by Ca2+-independent protein kinase C (nPKC) activation and its regulation by calcineurin activation. J Biol Chem. Oct. 23, 1998;273(43):28392-8.
Challacombe et al., Neutrophils are a key component of the anti-tumor efficacy of topical chemotherapy with ingenol-3-angelate. J Immunol. Dec. 1, 2006;177(11):8123-32.
Khiev et al., Ingenane-type diterpenes with a modulatory effect on IFN-γ production from the roots of Euphorbia kansui. Arch Pharm Res. Sep. 2012;35(9):1553-8. doi: 10.1007/s12272-012-0905-1. Epub Oct. 9, 2012.

(Continued)

*Primary Examiner* — Sun Jae Yoo
(74) *Attorney, Agent, or Firm* — Wolf, Greenfield & Sacks, P.C.

(57) ABSTRACT

The present invention relates to a derivative of 13-oxidized ingenol, use thereof in the prevention and/or treatment of a disease associated with proliferation or tumor in a subject, or a cosmetic indication, and use thereof in the prevention and/or treatment of a disease responsive to neutrophil oxidative burst, a disease responsive to a release of IL-8 by keratinocyte, or a disease responsive to induction of necrosis.

8 Claims, No Drawings

(56) References Cited

OTHER PUBLICATIONS

Ogbourne et al., Antitumor activity of 3-ingenyl angelate: plasma membrane and mitochondrial disruption and necrotic cell death. Cancer Res. Apr. 15, 2004;64(8):2833-9.

Ohyoshi et al., Total synthesis of natural derivatives and artificial analogs of 13-oxyingenol and their biological evaluation. Org Biomol Chem. Dec. 28, 2016; 14(48):11426-11437. Epub Nov. 22, 2016.

Rosen et al., Dual mechanism of action of ingenol mebutate gel for topical treatment of actinic keratoses: rapid lesion necrosis followed by lesion-specific immune response. J Am Acad Dermatol. Mar. 2012;66(3):486-93. doi: 10.1016/j.jaad.2010.12.038. Epub Nov. 4, 2011. Review.

Wang et al., Bioactivity-guided isolation of antiproliferative diterpenoids from Euphorbia kansui. Phytother Res. Jun. 2012;26(6):853-9. doi: 10.1002/ptr.3640. Epub Nov. 14, 2011.

Wu et al., Antitumor agents, 119. Kansuiphorins A and B, two novel antileukemic diterpene esters from Euphorbia kansui. J Nat Prod. May-Jun. 1991;54(3):823-9.

Zhao et al., Research progress on biology, chemical constituents in *Euphorbia kansui*, and their pharmacological effects. Chinese Traditional and Herbal Drugs. Oct. 2014;45:3029-33. doi: 10.7501/j.issn.0253-2670.2014.20.027.

PCT/CN2018/090272, Dec. 19, 2019, International Preliminary Report on Patentability and English translation thereof.

EP 18812748.4, Mar. 10, 2011, Extended European Search Report.

PCT/CN2018/090272, Sep. 6. 2018, International Search Report and Written Opinion.

Extended European Search Report for Application No. 18812748.4, dated Mar. 10, 2021.

International Preliminary Report on Patentability for Application No. PCT/CN2018/090272, dated Dec. 19, 2019.

Chinese Office Action for Application No. 201880038226.7, dated Jan. 6, 2022.

CAS RN 76663-56-4, entered Nov. 16, 1984. 4 pages.

* cited by examiner

13-OXIDIZED INGENOL DERIVATIVE AND USE THEREOF

RELATED APPLICATIONS

This application is a national stage filing under 35 U.S.C. § 371 of international PCT application, PCT/CN2018/090272, filed Jun. 7, 2018, which claims priority to international PCT Application, PCT/CN2017/08770, filed on Jun. 9, 2017, each of which is incorporated herein by reference in their entirety.

TECHNICAL FIELD

The present invention relates to a derivative of 13-oxidized ingenol (13-oxyingenol), use thereof in the prevention and/or treatment of a disease associated with proliferation or tumor in a subject, or a cosmetic indication, and use thereof in the prevention and/or treatment of a disease responsive to neutrophil oxidative burst, a disease responsive to a release of IL-8 by keratinocyte, or a disease responsive to induction of necrosis.

BACKGROUND ART

Ingenol is a class of tetranuclear diterpenoids, which is mostly present in the form of an ester in the *Euphorbia*. It was originally isolated as a stimulant and a tumor promotor from *Leptochloa chinensis* in the 70s of last century. Modern studies have shown that such compounds have antitumor activity (Wang H Y et al, Phytotherapy research, 2012, 26 (6): 853-9), and antiviral activity (Abreu C M et al, PLOS ONE, 2014, 9 (5): e97257), etc., and certain ingenol compounds are PKC agonists (Asada A. et al, The Journal of Biological Chemistry, 1998, 273(43): 28392-28398). Ingenol 3-angelate has been approved by the US FDA in 2012 for topical treatment of solar keratosis, its use in the treatment of non-melanoma skin cancer is also in clinical trials.

The parent nucleus of ingenol compounds of natural source exists mainly in three forms: ingenol, 13-oxidized ingenol (i.e. 13-oxyingenol), and 16-oxidized ingenol. Among them, 13-oxidized ingenol is mainly found in *Euphorbia kansui* L., *Euphorbia cornigera* B. and *Euphorbia cyparissias* L. The *kansui* L. is one of the commonly used toxic Chinese herbal medicines. It has the purgative and dampness-eliminating function. Modern research has found that it has obvious purgative effect, anti-tumor effect, anti-viral effect and anti-fertility effect (Zhao Xueyan et al., Chinese herbal medicine, 2014, 45 (20): 3029-3033). Studies on the chemical components and biological activities of *kansui* L. have shown that ingenol and 13-oxidized ingenol-type compounds are the main active components of the anti-tumor effects (Wang H Y et al., Phytotherapy Research, 2012, 26(6): 853-859; Wu T S et al, Journal of Natural Products, 1991, 54(3): 823-829), wherein certain 13-oxidized ingenol-type compounds can also induce production of IFN-γ in NK92 cells (Khiev P. et al, Archives Pharmacal Research, 2012, 35(9): 1553-1558). The naturally occurring 13-oxidized ingenane diterpene ester compounds have a broad spectrum of cytotoxicity, which limits their use. It is necessary to find new 13-oxidized ingenane diterpene ester compounds which have the advantage of being highly efficient and less toxic than naturally occurring compounds.

Studies have shown that treatment of solar keratosis by ingenol-3-angelate is achieved through a dual-acting mechanism: (i) inducing the death of aberrant keratinocytes by direct cytotoxicity or induction of apoptosis; (ii) inducing an immune response in a targeted lesion area, further killing abnormal cells by neutrophil-mediated antibody-dependent cytotoxicity (Rosen R H et al, Journal of the American Academy of Dermatology, 2012, 66 (3): 486-493). At high concentrations (hundreds of micromoles), ingenol-3-angelate can induce rapid death of cancer cells (Ogbourne S. M. et al, Cancer Research, 2004, 64: 2833-2839). Ingenol-3-angelate can also induce proinflammatory effect in part by activating multiple PKC isoforms, including activation of vascular endothelial cells (Hampson P. et al, Cancer Immunol Immunother, 2008, 57: 1241-1251), and by inducing the release of IL-8 by keratinocytes and chemotaxis of neutrophils to the inflammatory site, a large amount of reactive oxygen species is released to kill the aberrant cells (Challacombe J M et al, The Journal of Immunology, 2006, 177: 8123-8132).

Studies have found that compounds having a dual-acting mechanism through direct cytotoxicity and immunostimulatory effect can be used for the preparation of a medication for treating diseases associated with proliferation or tumor, and can also be used for the preparation of a medication for treating or improving symptoms associated in the cosmetic field.

Therefore, it is necessary to find a new 13-oxidized ingenol derivative having a dual-acting mechanism of direct cytotoxicity and immunostimulatory effect, which has similar or improved biological activity to the ingenol-3-angelate.

SUMMARY

In the present invention, the scientific and technical terms used herein have the meanings commonly understood by those skilled in the art, unless otherwise stated. Moreover, the laboratory procedures involved herein are routine steps that are widely used in the corresponding art. Also, for a better understanding of the present invention, definitions and explanations of related terms are provided below.

As used herein, the term "ingenol" refers to a compound having the structure below (wherein the numbers 3, 4, 5, 13, and 20 represent the number of carbon atoms):

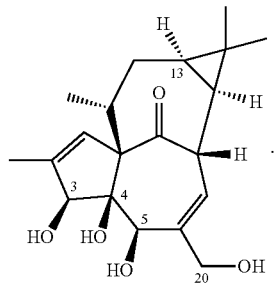

As used herein, the term "$C_1$-$C_{11}$ linear or branched alkyl" refers to a linear or branched alkyl containing 1 to 11 carbon atoms, including but not limited to $C_1$-$C_4$ linear alkyl, $C_1$-$C_4$ branched alkyl, $C_4$-$C_9$ linear alkyl, $C_4$-$C_9$ branched alkyl, $C_9$-$C_{11}$ linear alkyl, $C_9$-$C_{11}$ branched alkyl, $C_1$-$C_{11}$ linear alkyl, $C_1$-$C_{11}$ branched alkyl, such as methyl, ethyl, n-propyl, isopropyl, n-butyl, 2-methylpropyl, 1-methylpropyl, 1,1-dimethylethyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl, n-heptyl, n-octyl, n-nonyl, n-decyl, n-undecyl, and the like. The term "$C_1$-$C_4$ linear or branched alkyl" refers to a linear or branched alkyl containing 1 to 4 carbon atoms.

As used herein, the term "$C_1$-$C_4$ linear or branched alkoxyl" refers to a group formed in the form of "$C_1$-$C_4$ linear or branched alkyl-O—".

As used herein, the term "$C_2$-$C_{11}$ linear or branched alkenyl" refers to a linear or branched alkenyl containing 2 to 11 carbon atoms which may contain one or more (e.g., 2, 3, 4 or 5) carbon-carbon double bonds, including but not limited to $C_2$-$C_4$ linear alkenyl, $C_2$-$C_4$ branched alkenyl, $C_3$-$C_5$ linear alkenyl, $C_3$-$C_5$ branched alkenyl, $C_4$-$C_5$ branched alkenyl, $C_5$-$C_9$ linear alkenyl, $C_5$-$C_9$ branched alkenyl, $C_9$-$C_{11}$ linear alkenyl, $C_9$-$C_{11}$ branched alkenyl, $C_1$-$C_{11}$ linear alkenyl, $C_1$-$C_{11}$ branched alkenyl, such as vinyl group, propenyl group, allyl group,

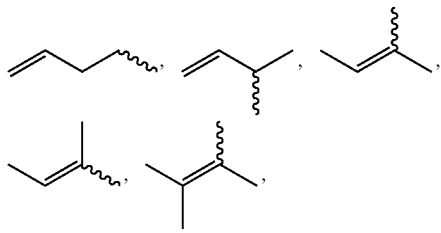

1,3-nondienyl and 1,3,5-nontrienyl.

As used herein, the term "6-10 membered aryl" refers to an aromatic cyclic group containing 6 to 10 carbon atoms, such as phenyl, and naphthyl.

As used herein, the term "5-8 membered heteroaryl" refers to an aromatic cyclic group containing 5 to 8 ring atoms, wherein one or more (e.g., 2, 3, 4 or 5) ring atoms are heteroatoms (e.g., an oxygen atom, a sulfur atom, a nitrogen atom), including, for example, 5-7-membered heteroaryl, 5-6-membered heteroaryl, 5-8-membered nitrogen-containing heteroaryl, 5-8-membered oxygen-containing heteroaryl, 5-6 membered nitrogen-containing heteroaryl, 5-6 membered oxygen-containing heteroaryl, and the like. Specific examples include, but are not limited to, furyl, thienyl, pyrrolyl, thiazolyl, isothiazolyl, thiadiazolyl, oxazolyl, isoxazolyl, oxadiazolyl, imidazolyl, pyrazolyl, indolyl, quinolyl, isoquinolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, 2-pyridone, 4-pyridone, pyrimidinyl, 1,4-dioxinyl, 2H-1,2-oxazinyl, 4H-1,2-oxazinyl, 6H-1,2-oxazinyl, 4H-1,3-oxazinyl, 6H-1,3-oxazinyl, 4H-1,4-oxazinyl, pyridazinyl, pyrazinyl, 1,2,3-triazinyl, 1,3,5-triazinyl, 1,2,4,5-tetrazinyl, azepinyl, 1,3-diazepinyl, azacyclooctatetraenyl, and the like.

As used herein, the term "5-8 membered cycloalkyl" refers to a cyclic alkyl containing 5 to 8 ring carbon atoms, such as a 5-6 membered cycloalkyl. Specific examples include, but are not limited to, cyclopentanyl, cyclohexanyl, cycloheptanyl, cyclooctanyl, and the like.

As used herein, the term "5-8 membered aliphatic heterocyclic group" is an aliphatic saturated or partially saturated, non-aromatic ring having at least one heteroatom (e.g., an oxygen atom, a sulfur atom, a nitrogen atom) as ring atom. Preferably, the number of said heteroatoms is 1, 2, 3 or 4, such as 5-8 membered nitrogen-containing aliphatic heterocyclic group, 5-6 membered nitrogen-containing aliphatic heterocyclic group, 5-8 membered oxygen-containing aliphatic heterocyclic group, and 6-7 membered oxygen-containing aliphatic heterocyclic group. Specific examples include, but are not limited to, 1,4-dioxanyl, 1,3-dioxanyl, 1,3-dioxolanyl, 1,4-dioxinyl, tetrahydrofuranyl, dihydropyrrolyl, pyrrolidinyl, imidazolidinyl, 4,5-dihydroimidazolyl, pyrazolidinyl, 4,5-dihydropyrazolyl, 2,5-dihydrothienyl, tetrahydrothiophenyl, 4,5-dihydrothiazolyl, piperidinyl, piperazinyl, morpholinyl, hexahydropyrimidinyl, hexahydropyridazinyl, 4,5-dihydrooxazolyl, 4,5-dihydroisoxazolyl, 2,3-dihydroisoxazolyl, 2H-1,2-oxazinyl, 6H-1,3-oxazinyl, 4H-1,3-thiazinyl, 6H-1,3-thiazinyl, 2H-pyranyl, 3,4-dihydro-2H-pyranyl.

As used herein, the term "8-10 membered saturated or partially saturated fused heterocyclic group" refers to a fused ring structure having 8 to 10 ring atoms formed by two or more cyclic structures which are joined together by sharing two adjacent atoms (i.e., sharing a bond) with each other, wherein one or more (e.g., 2, 3, 4 or 5) of the ring atoms are heteroatom(s) (e.g., oxygen atom, sulfur atom, nitrogen atom), and the fused ring structure is saturated or partially saturated. For example, 8-10 membered saturated nitrogen-containing fused heterocyclic group, 8-10 membered partially saturated oxygen-containing fused heterocyclic group, and 8-10 membered partially saturated nitrogen-containing fused heterocyclic group, such as a benzopiperidinyl group, a benzopiperazinyl, benzopyrrolidinyl, benzomorpholinyl, and the like.

As used herein, the term "halogen" includes, for example, fluorine, chlorine, bromine, and iodine.

As used herein, " ⌇ " means that a substituent is attached to another group via a chemical bond at the position of the wavy line.

As used herein, the term "solvate" refers to a substance formed by association of a compound with a solvent molecule. The solvent may be an organic solvent (e.g., methanol, ethanol, propanol, acetonitrile, etc.), water, and the like. For example, the compounds of the invention may form an acetonide with acetone or form a hydrate with water.

As used herein, the term "pharmaceutically acceptable salts" includes, but is not limited to, inorganic acid salts and organic acid salts such as hydrochloride, hydrobromide, hydroiodide, nitrate, sulfate, bisulfate, phosphate, hydrophosphate, acetate, propionate, butyrate, oxalate, trimethylacetate, oxalate, alginate, citrate, picrate, gluconate, tartrate, maleate, mesylate, succinate, pamoate, trifluoroacetate, and the like.

As used herein, the term "crystal form" refers to the crystal structure of a substance. When crystallization of a substance occurs, it is affected by various factors, so that the intramolecular or intermolecular bonding mode changes, resulting in the different arrangement of the molecules or atoms in the lattice space, thereby forming different crystal structures. The compound of the present invention may exist in a single crystal structure or in a plurality of crystal structures, i.e., has "polymorphs". The compounds of the invention may exist in different crystal forms.

As used herein, the term "prodrug" refers to a compound that can be converted to a compound of the invention by a reaction, such as oxidation, reduction, hydrolysis, and the like, in a subject. A prodrug of a compound of the invention may or may not possess the pharmaceutical activity of the compounds of the invention itself. For example, a compound comprising a hydroxyl group can be administered in the form of an ester which is hydrolyzed in vivo into a hydroxyl compound. Suitable esters which can be converted in vivo into hydroxyl compounds include acetate, citrate, lactate, tartrate, malonate, oxalate, salicylate, propionate, succinate, fumarate, maleate, methylene-bis-2-hydroxynaphthoate, and the like. Similarly, a compound comprising an amino group may be acylated, alkylated or phosphorylated to form a compound such as an eicosanoylamino, alanylamino, or pivaloyloxymethylamino compound for administration.

As used herein, the term "metabolite" refers to a substance produced by the metabolism of a compound in vivo, which may have a higher biological activity than the original compound, may also have lower biological activity than the original compound, or may not have biological activity.

As used herein, the term "prevention" refers to preventing or delaying the onset of a disease.

As used herein, the term "treatment" refers to curing or at least partially arresting a disease, or alleviating the symptoms of a disease.

The "effective amount" of the invention refers to an amount sufficient to achieve, or at least partially achieve, the desired effect. For example, "prophylactically effective amount" refers to an amount sufficient to prevent, arrest or delay the onset of a disease; "therapeutically effective amount" refers to an amount sufficient to cure or at least partially arrest a disease and a complication thereof of a patient already suffering from such disease. Determination of such an effective amount is well within the capabilities of those skilled in the art. For example, the amount effective for therapeutic use will depend on the severity of a condition to be treated, the overall status of the patient's own immune system, the general conditions of the patient such as age, weight and gender, the mode of administration of the drug, and other treatments administered simultaneously, and the like.

The inventors have obtained new 13-oxidized ingenol derivatives by intensive research and creative labor, and surprisingly found that the 13-oxidized ingenol derivatives have an influence on the oxidative burst of the neutrophils, and are capable of stimulating the release of IL-8 by human keratinocytes (HaCaT), thereby providing the following invention:

In one aspect, the application provides a compound of Formula (I), or a pharmaceutically acceptable salt, solvate, prodrug, metabolite or crystal form thereof,

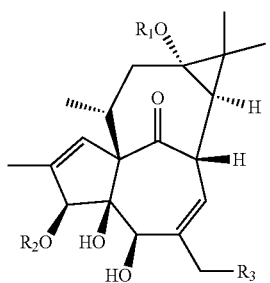

(I)

wherein, $R_1$ is selected from the group consisting of hydrogen and M-C(O)—, wherein M is selected from the group consisting of hydrogen, $C_1$-$C_{11}$ linear or branched alkyl, $C_2$-$C_{11}$ linear or branched alkenyl, 6-10 membered aryl and 5-8 membered heteroaryl;

$R_2$ is selected from the group consisting of hydrogen and Q-C(O)—, wherein Q is selected from the group consisting of hydrogen, $C_1$-$C_{11}$ linear or branched alkyl, $C_2$-$C_{11}$ linear or branched alkenyl, 5-8 membered cycloalkyl, 6-10 membered aryl, 5-8 membered aliphatic heterocyclic group, 5-8 membered heteroaryl group, 8-10 membered saturated or partially saturated fused heterocyclic group and NR'R", wherein R' is $C_1$-$C_4$ linear or branched alkyl group, R" is phenyl group optionally substituted with halogen(s);

$R_3$ is selected from the group consisting of hydrogen, hydroxyl and X—C(O)—O—, wherein X is selected from the group consisting of hydrogen, $C_1$-$C_{11}$ linear or branched alkyl, $C_2$-$C_{11}$ linear or branched alkenyl, 5-8 membered cycloalkyl, 6-10 membered aryl, 5-8 membered aliphatic heterocyclic group, 5-8 membered heteroaryl group, 8-10 membered saturated or partially saturated fused heterocyclic group and NR'R", wherein R' is $C_1$-$C_4$ linear or branched alkyl group, R" is phenyl group optionally substituted with halogen(s).

Optionally, the $C_1$-$C_{11}$ linear or branched alkyl or $C_2$-$C_{11}$ linear or branched alkenyl group is independently substituted with one or more phenyl groups, wherein the phenyl group is optionally substituted with methyl group(s).

Optionally, the 5-8 membered cycloalkyl, 6-10 membered aryl, 5-8 membered aliphatic heterocyclic group, 5-8 membered heteroaryl group, 8-10 membered saturated or partially saturated fused heterocyclic group is independently substituted with one or more substituents selected from the group consisting of halogen, $C_1$-$C_4$ linear or branched alkyl, $C_1$-$C_4$ linear or branched alkoxyl, phenyl, —$NH_2$, —$NHCH_3$ and —NH—$CH_2$-Ph.

In certain embodiments, when $R_2$ is Q-C(O)—, $R_3$ is hydrogen or hydroxyl, more preferably hydroxyl.

In certain embodiments, when $R_3$ is X—C(O)—O—, $R_2$ is hydrogen.

In certain embodiments, $R_1$ is hydrogen. In certain embodiments, $R_1$ is M-C(O)—, wherein M is selected from the group consisting of $C_1$-$C_{11}$ linear alkyl (e.g., methyl, n-propyl, n-pentyl, n-heptyl, n-nonyl, n-undecyl) and $C_2$-$C_{11}$ linear alkenyl (e.g., nondienyl, and nontrienyl).

In certain embodiments, $R_1$ is hydrogen. In certain embodiments, $R_1$ is M-C(O)—, wherein M is selected from the group consisting of methyl, n-propyl, n-pentyl, n-heptyl, n-nonyl, n-undecyl, 1,3-nondienyl and 1,3,5-nontrienyl.

In certain embodiments, $R_2$ is hydrogen. In certain embodiments, $R_2$ is Q-C(O)—, wherein Q is selected from the group consisting of $C_1$-$C_5$ linear alkyl, $C_4$-$C_5$ branched alkyl, $C_3$-$C_5$ linear alkenyl, $C_3$-$C_5$ branched alkenyl, 5-6 membered cycloalkyl, phenyl, 5-6 membered nitrogen-containing aliphatic heterocyclic group, 5-6 membered heteroaryl, 8-10 membered partially saturated nitrogen-containing fused heterocyclic group, and NR'R", wherein, R' is methyl group, R" is phenyl group optionally substituted with halogen(s); and in the 5-6 membered heteroaryl group, the heteroatom is selected from the group consisting of nitrogen and oxygen.

Optionally, the $C_1$-$C_5$ linear alkyl group, $C_4$-$C_5$ branched alkyl group, $C_3$-$C_5$ linear alkenyl group or $C_3$-$C_5$ branched alkenyl group is independently substituted with one or more phenyl groups, wherein the phenyl group is optionally substituted with methyl group(s).

Optionally, the 5-6 membered cycloalkyl, phenyl, 5-6 membered nitrogen-containing aliphatic heterocyclic group, 5-6 membered heteroaryl or 8-10 membered partially saturated nitrogen-containing fused heterocyclic group is independently substituted with one or more substituents selected from the group consisting of halogen, methyl, ethyl, methoxy, phenyl, —$NH_2$, —$NHCH_3$ and —NH—$CH_2$-Ph.

In certain embodiments, $R_2$ is hydrogen. In certain embodiments, $R_2$ is Q-C(O)—, wherein Q is selected from the group consisting of methyl, n-propyl, n-pentyl, t-butyl,

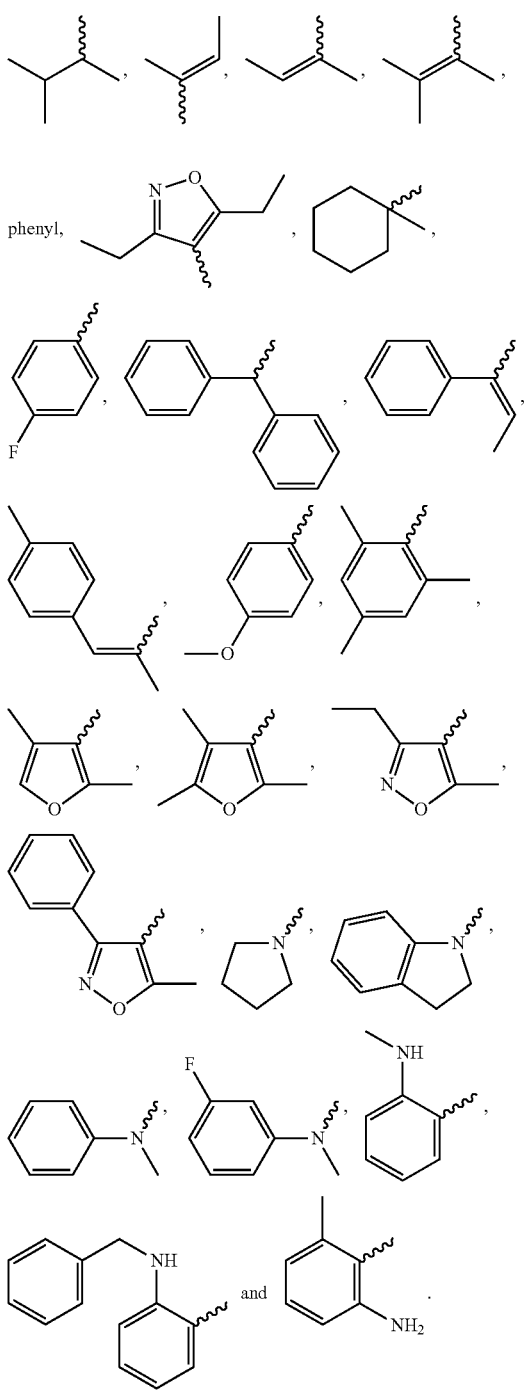

In certain embodiments, $R_2$ is hydrogen. In certain embodiments, $R_2$ is Q-C(O)—, wherein Q is selected from the group consisting of $C_1$-$C_5$ linear alkyl, $C_4$-$C_5$ branched alkyl, $C_3$-$C_5$ linear alkenyl, $C_3$-$C_5$ branched alkenyl, 5-membered heteroaryl group substituted with ethyl group(s), wherein the 5-membered heteroaryl group comprises heteroatom(s) selected from the group consisting of nitrogen and oxygen.

In certain embodiments, $R_2$ is hydrogen. In certain embodiments, $R_2$ is Q-C(O)—, wherein Q is selected from the group consisting of methyl, n-propyl, n-pentyl, t-butyl,

In certain embodiments, $R_2$ is hydrogen. In certain embodiments, $R_2$ is Q-C(O)—, wherein Q is selected from the group consisting of methyl, n-propyl,

In certain embodiments, $R_3$ is hydrogen. In certain embodiments, $R_3$ is hydroxyl group. In certain embodiments, $R_3$ is X—C(O)—O—, wherein X is selected from the group consisting of hydrogen, $C_1$-$C_5$ linear alkyl, $C_4$-$C_5$ branched alkyl, $C_3$-$C_5$ linear alkenyl, $C_3$-$C_5$ branched alkenyl, 5-6 membered cycloalkyl, phenyl, 5-6 membered nitrogen-containing aliphatic heterocyclic group, 5-6 membered heteroaryl, 8-10 membered partially saturated nitrogen-containing fused heterocyclic group, and NR'R", wherein, R' is methyl group, R" is phenyl group optionally substituted with halogen(s); and in the 5-6 membered heteroaryl group, the heteroatom is selected from the group consisting of nitrogen and oxygen.

Optionally, the $C_1$-$C_5$ linear alkyl group, $C_4$-$C_5$ branched alkyl group, $C_3$-$C_5$ linear alkenyl group or $C_3$-$C_5$ branched alkenyl group is independently substituted with one or more phenyl groups, wherein the phenyl group is optionally substituted with methyl group(s).

Optionally, the 5-6 membered cycloalkyl, phenyl, 5-6 membered nitrogen-containing aliphatic heterocyclic group, 5-6 membered heteroaryl or 8-10 membered partially saturated nitrogen-containing fused heterocyclic group is independently substituted with one or more substituents selected from the group consisting of halogen, methyl, ethyl, methoxy, phenyl, —NH$_2$, —NHCH$_3$ and —NH—CH$_2$-Ph.

In certain embodiments, $R_3$ is hydrogen. In certain embodiments, $R_3$ is hydroxyl group. In certain embodiments, $R_3$ is X—C(O)—O—, wherein X is selected from the group consisting of methyl, n-propyl, t-butyl, n-pentyl,

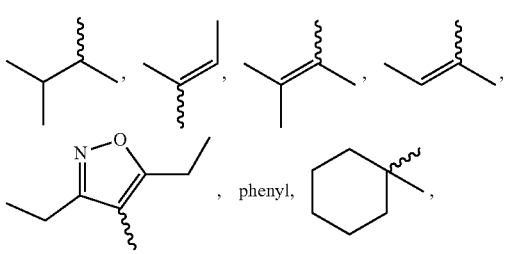

-continued

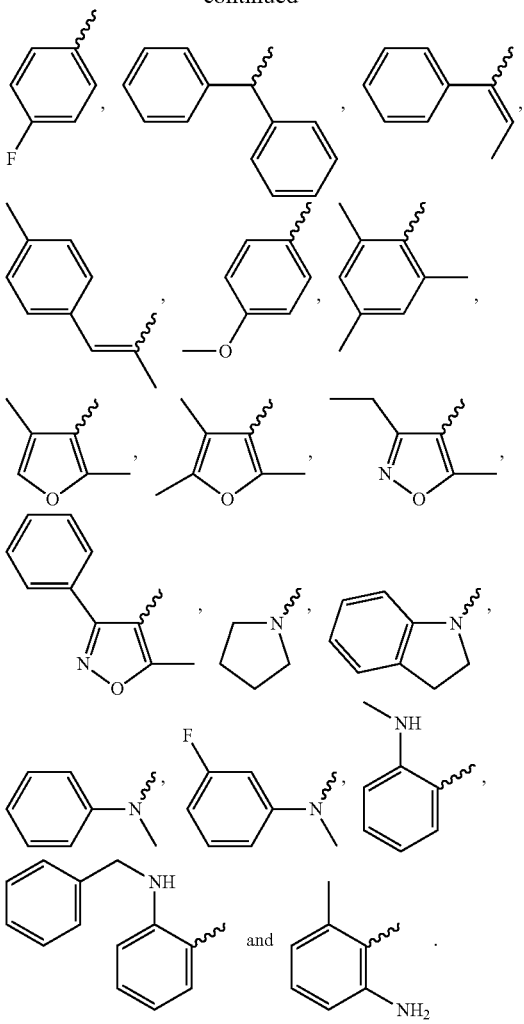

In certain embodiments, $R_3$ is hydrogen. In certain embodiments, $R_3$ is hydroxyl group. In certain embodiments, $R_3$ is X—C(O)—O—, wherein X is selected from the group consisting of $C_1$-$C_3$ linear alkyl, $C_3$-$C_5$ linear alkenyl, $C_3$-$C_5$ branched alkenyl, and 5-membered heteroaryl group substituted with ethyl group(s), wherein the 5-membered heteroaryl group comprises heteroatom(s) selected from the group consisting of nitrogen and oxygen.

In certain embodiments, $R_3$ is hydrogen. In certain embodiments, $R_3$ is hydroxyl group. In certain embodiments, $R_3$ is X—C(O)—O—, wherein X is selected from the group consisting of methyl, n-propyl, n-pentyl, t-butyl,

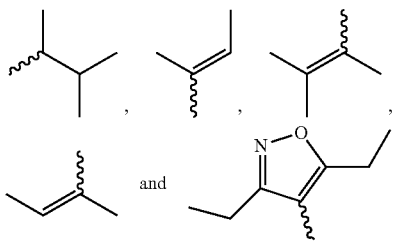

In certain embodiments, $R_3$ is hydrogen. In certain embodiments, $R_3$ is hydroxyl group. In certain embodiments, $R_3$ is X—C(O)—O—, wherein X is selected from the group consisting of n-propyl,

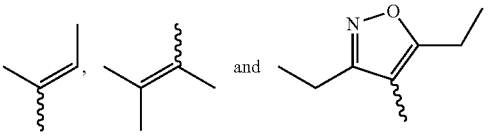

In certain embodiments, $R_1$ is selected from the group consisting of hydrogen and M-C(O)—, wherein M is selected from the group consisting of $C_1$-$C_{11}$ linear alkyl (e.g., methyl, n-propyl, n-pentyl, n-heptyl, n-nonyl, n-undecyl) and $C_2$-$C_{11}$ linear alkenyl (e.g., nondienyl, and nontrienyl);

$R_2$ is selected from the group consisting of hydrogen and Q-C(O)—, wherein Q is selected from the group consisting of $C_1$-$C_5$ linear alkyl, $C_4$-$C_5$ branched alkyl, $C_3$-$C_5$ linear alkenyl, $C_3$-$C_5$ branched alkenyl, phenyl, 5-membered heteroaryl group substituted with ethyl group(s), wherein the 5-membered heteroaryl group comprises heteroatom(s) selected from the group consisting of nitrogen and oxygen; and $R_3$ is selected from the group consisting of hydrogen, hydroxyl and X—C(O)—O—, wherein X is selected from the group consisting of $C_1$-$C_5$ linear alkyl, $C_4$-$C_5$ branched alkyl, $C_3$-$C_5$ linear alkenyl, $C_3$-$C_5$ branched alkenyl, phenyl, and 5-membered heteroaryl group substituted with ethyl group(s), wherein the 5-membered heteroaryl group comprises heteroatom(s) selected from the group consisting of nitrogen and oxygen.

In certain embodiments, $R_2$ is hydrogen. In certain embodiments, $R_2$ is Q-C(O)—, wherein Q is selected from the group consisting of $C_1$-$C_5$ linear alkyl, $C_4$-$C_5$ branched alkyl, $C_3$-$C_5$ linear alkenyl, $C_3$-$C_5$ branched alkenyl, phenyl, 5-membered heteroaryl group substituted with ethyl group(s), wherein the 5-membered heteroaryl group comprises heteroatom(s) selected from the group consisting of nitrogen and oxygen.

In certain embodiments, $R_3$ is hydrogen. In certain embodiments, $R_3$ is hydroxyl group. In certain embodiments, $R_3$ is X—C(O)—O—, wherein X is selected from the group consisting of $C_1$-$C_5$ linear alkyl, $C_4$-$C_5$ branched alkyl, $C_3$-$C_5$ linear alkenyl, $C_3$-$C_5$ branched alkenyl, phenyl, and 5-membered heteroaryl group substituted with ethyl group(s), wherein the 5-membered heteroaryl group comprises heteroatom(s) selected from the group consisting of nitrogen and oxygen.

In certain embodiments, $R_1$ is selected from the group consisting of hydrogen and M-C(O)—, wherein M is selected from the group consisting of methyl, n-propyl, n-pentyl, n-heptyl, n-nonyl, n-undecyl, 1,3-nondienyl and 1,3,5-nontrienyl.

$R_2$ is selected from the group consisting of hydrogen and Q-C(O)—, wherein Q is selected from the group consisting of methyl, n-propyl, n-pentyl, t-butyl,

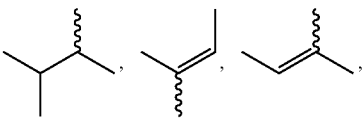

-continued

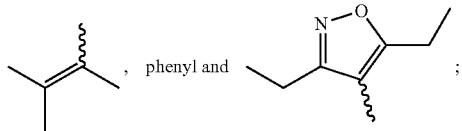, phenyl and and

R$_3$ is selected from the group consisting of hydrogen, hydroxyl and X—C(O)—O—, wherein X is selected from the group consisting of methyl, n-propyl, t-butyl, n-pentyl,

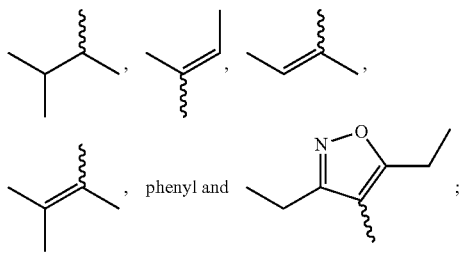, phenyl and ;

In certain embodiments, R$_2$ is hydrogen. In certain embodiments, R$_2$ is Q-C(O)—, wherein Q is selected from the group consisting of methyl, n-propyl, n-pentyl, t-butyl,

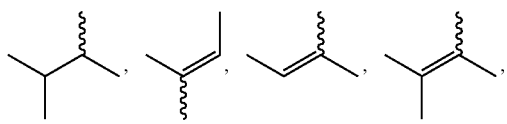

phenyl and

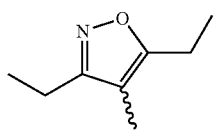.

In certain embodiments, R$_3$ is hydrogen. In certain embodiments, R$_3$ is hydroxyl group. In certain embodiments, R$_3$ is X—C(O)—O—, wherein X is selected from the group consisting of methyl, n-propyl, t-butyl, n-pentyl,

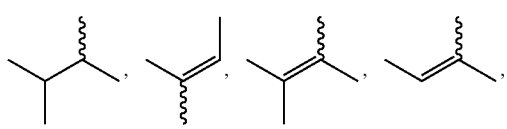

phenyl and

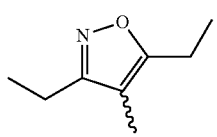.

In certain embodiments, R$_1$ is selected from the group consisting of hydrogen and M-C(O)—, wherein M is selected from the group consisting of methyl, n-propyl, n-pentyl, n-heptyl, n-nonyl, 1,3-nondienyl and 1,3,5-nontrienyl.

R$_2$ is selected from the group consisting of hydrogen and Q-C(O)—, wherein Q is selected from the group consisting of methyl, n-propyl, n-pentyl, t-butyl,

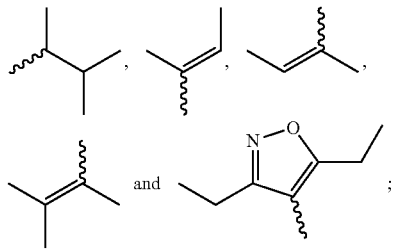

and

R$_3$ is selected from the group consisting of hydrogen and X—C(O)—O—, wherein X is selected from the group consisting of methyl, n-propyl, t-butyl, n-pentyl,

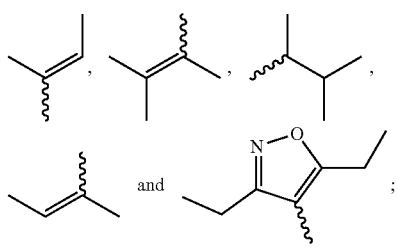

and,
when R$_1$ is M-C(O)—, M is methyl or 1,3,5-nontrienyl, R$_3$ is X—C(O)—O— and X is

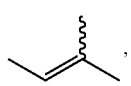,

R$_2$ is not hydrogen;
when R$_1$ is M-C(O)—, M is n-nonyl and R$_3$ is CH$_3$—C(O)—O—, R$_2$ is not

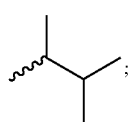;

when R$_1$ is hydrogen and R$_3$ is (CH$_3$)$_3$C—C(O)—O—, R$_2$ is not hydrogen or (CH$_3$)$_3$C—C(O)—.

In certain embodiments, R$_2$ is hydrogen. In certain embodiments, R$_2$ is Q-C(O)—, wherein Q is selected from the group consisting of methyl, n-propyl, n-pentyl, t-butyl,

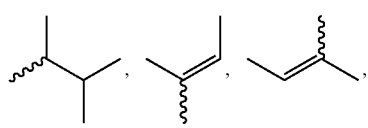

-continued

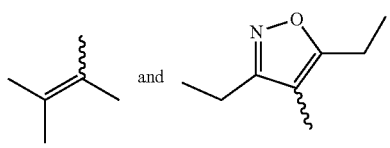

In certain embodiments, R₃ is hydrogen. In certain embodiments, R₃ is X—C(O)—O—, wherein X is selected from the group consisting of methyl, n-propyl, t-butyl, n-pentyl,

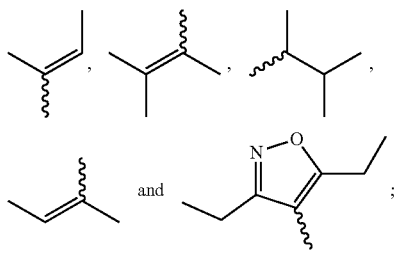

In certain embodiments, R₁ is selected from the group consisting of hydrogen and M-C(O)—, wherein M is selected from the group consisting of methyl, n-propyl, n-pentyl, n-heptyl, n-nonyl, 1,3-nondienyl and 1,3,5-nontrienyl.

R₂ is selected from the group consisting of hydrogen and Q-C(O)—, wherein Q is selected from the group consisting of methyl, n-propyl, n-pentyl, t-butyl,

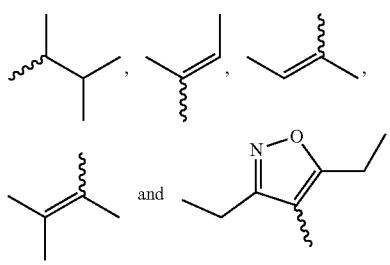

R₃ is hydroxyl group;
and,
when R₂ is Q-C(O)— and Q is

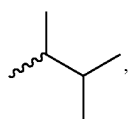

R₁ is not n-heptyl or n-nonyl;
when R₂ is hydrogen, R₁ is not hydrogen or 1,3,5-nontrienyl.

In certain embodiments, R₂ is hydrogen. In certain embodiments, R₂ 为 Q-C(O)—, wherein Q is selected from the group consisting of methyl, n-propyl, n-pentyl, t-butyl,

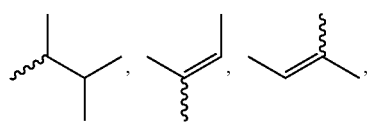

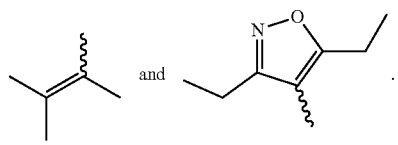

In certain embodiments, R₁ is M-C(O)—, and M is n-undecyl;

R₂ is Q-C(O)—, wherein Q is selected from the group consisting of methyl, n-propyl,

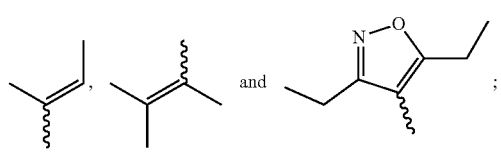

R₃ is selected from the group consisting of hydrogen, hydroxyl and X—C(O)—O—, wherein X is selected from the group consisting of methyl, n-propyl, t-butyl,

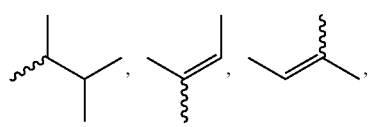

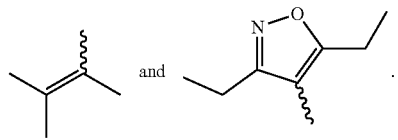

In certain embodiments, R₃ is hydrogen. In certain embodiments, R₃ is hydroxyl group.

In certain embodiments, R₃ is X—C(O)—O—, wherein X is selected from the group consisting of methyl, n-propyl, t-butyl,

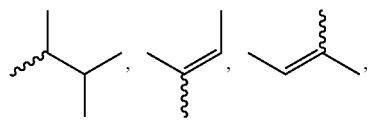

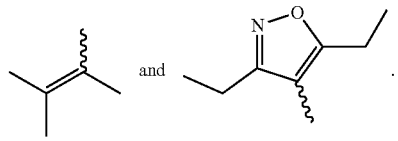

In certain embodiments, R₃ is X—C(O)—O—, wherein X is selected from the group consisting of methyl, n-propyl,

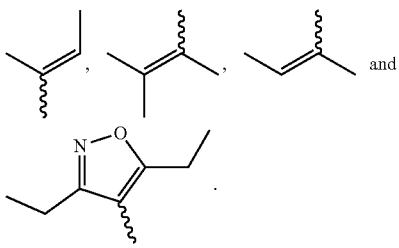

In certain embodiments, $R_1$ is M-C(O)—, M is n-undecyl; $R_2$ is hydrogen; $R_3$ is X—C(O)—O—, wherein X is selected from the group consisting of methyl, n-propyl,

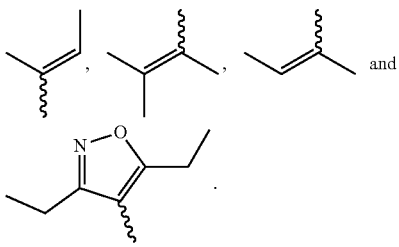

In certain embodiments, $R_1$ is M-C(O)—, M is n-undecyl; $R_2$ is

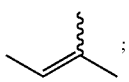

$R_3$ is X—C(O)—O—, wherein X is selected from the group consisting of methyl, n-propyl, t-butyl, n-pentyl,

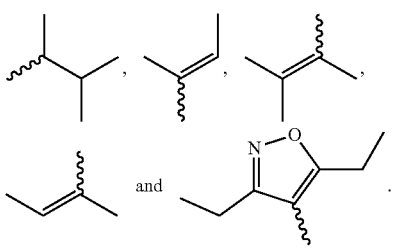

In certain embodiments, $R_1$ is selected from the group consisting of hydrogen and M-C(O)—, wherein M is selected from the group consisting of $C_1$-$C_{11}$ linear alkyl (e.g., methyl, n-propyl, n-pentyl, n-heptyl, n-nonyl, n-undecyl) and $C_2$-$C_{11}$ linear alkenyl (e.g., nondienyl, and nontrienyl);

$R_2$ is selected from the group consisting of hydrogen and Q-C(O)—, wherein Q is selected from the group consisting of methyl, $C_3$-$C_5$ linear alkenyl, $C_3$-$C_5$ branched alkenyl, 5-6 membered cycloalkyl, phenyl, 5-6 membered nitrogen-containing aliphatic heterocyclic group, 5-6 membered heteroaryl group, 8-10 membered partially saturated nitrogen-containing fused heterocyclic group, and NR'R", wherein R' is methyl, and R" is phenyl group optionally substituted with halogen(s); wherein the 5-6 membered heteroaryl group comprises heteroatom(s) selected from the group consisting of nitrogen and oxygen; wherein the methyl, $C_3$-$C_5$ linear alkenyl or $C_3$-$C_5$ branched alkenyl group is independently substituted with one or more phenyl groups, wherein the phenyl group is optionally substituted with methyl group(s);

optionally, the 5-6 membered cycloalkyl, phenyl, 5-6 membered nitrogen-containing aliphatic heterocyclic group, 5-6 membered heteroaryl or 8-10 membered partially saturated nitrogen-containing fused heterocyclic group is independently substituted with one or more substituents selected from the group consisting of halogen, methyl, ethyl, methoxy, phenyl, —NH$_2$, —NHCH$_3$ and —NH—CH$_2$-Ph;

$R_3$ is selected from the group consisting of hydroxyl and X—C(O)—O—, wherein X is selected from the group consisting of hydrogen, methyl, $C_3$-$C_5$ linear alkenyl, $C_3$-$C_5$ branched alkenyl, 5-6 membered cycloalkyl, phenyl, 5-6 membered nitrogen-containing aliphatic heterocyclic group, 5-6 membered heteroaryl group, 8-10 membered partially saturated nitrogen-containing fused heterocyclic group, and NR'R", wherein R' is methyl, and R" is phenyl group optionally substituted with halogen(s); wherein the 5-6 membered heteroaryl group comprises heteroatom(s) selected from the group consisting of nitrogen and oxygen; wherein the methyl, $C_3$-$C_5$ linear alkenyl or $C_3$-$C_5$ branched alkenyl group is independently substituted with one or more phenyl groups, wherein the phenyl group is optionally substituted with methyl group(s);

optionally, the 5-6 membered cycloalkyl, phenyl, 5-6 membered nitrogen-containing aliphatic heterocyclic group, 5-6 membered heteroaryl or 8-10 membered partially saturated nitrogen-containing fused heterocyclic group is independently substituted with one or more substituents selected from the group consisting of halogen, methyl, ethyl, methoxy, phenyl, —NH$_2$, —NHCH$_3$ and —NH—CH$_2$-Ph.

In certain embodiments, $R_2$ is hydrogen. In certain embodiments, $R_2$ is Q-C(O)—, wherein Q is selected from the group consisting of methyl, $C_3$-$C_5$ linear alkenyl, $C_3$-$C_5$ branched alkenyl, 5-6 membered cycloalkyl, phenyl, 5-6 membered nitrogen-containing aliphatic heterocyclic group, 5-6 membered heteroaryl group, 8-10 membered partially saturated nitrogen-containing fused heterocyclic group, and NR'R", wherein R' is methyl, and R" is phenyl group optionally substituted with halogen(s); wherein the 5-6 membered heteroaryl group comprises heteroatom(s) selected from the group consisting of nitrogen and oxygen.

In certain embodiments, $R_3$ is hydroxyl group. In certain embodiments, $R_3$ is X—C(O)—O—, wherein X is selected from the group consisting of hydrogen, methyl, $C_3$-$C_5$ linear alkenyl, $C_3$-$C_5$ branched alkenyl, 5-6 membered cycloalkyl, phenyl, 5-6 membered nitrogen-containing aliphatic heterocyclic group, 5-6 membered heteroaryl group, 8-10 membered partially saturated nitrogen-containing fused heterocyclic group, and NR'R", wherein R' is methyl, and R" is phenyl group optionally substituted with halogen(s); wherein the 5-6 membered heteroaryl group comprises heteroatom(s) selected from the group consisting of nitrogen and oxygen.

In certain embodiments, Q and X are independently selected from the group consisting of the following groups:

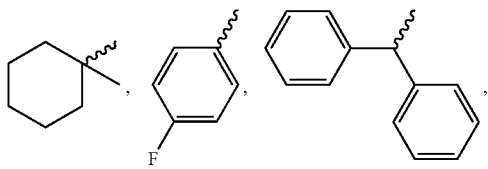

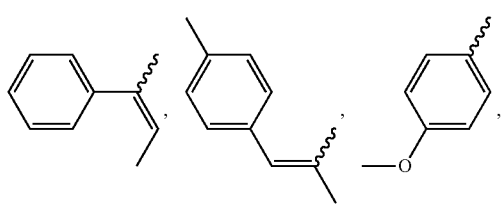

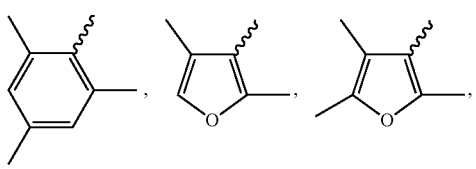

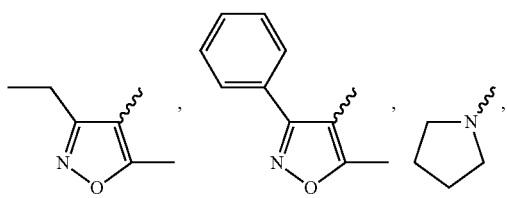

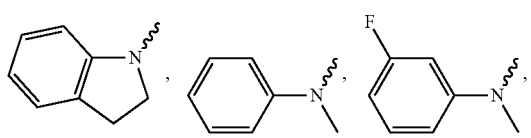

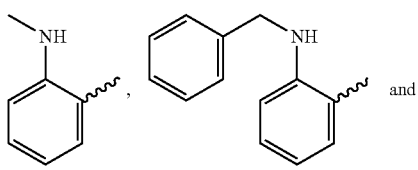

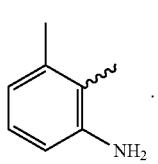

In certain embodiments, $R_1$ is M-C(O)—, and M is n-nonyl, n-heptyl or n-undecyl;

$R_2$ is selected from the group consisting of hydrogen and Q-C(O)—, wherein Q is selected from the group consisting of

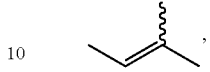

t-butyl, n-pentyl

and phenyl;

$R_3$ is selected from the group consisting of a hydroxyl group and X—C(O)—O—, wherein X is selected from the group consisting of

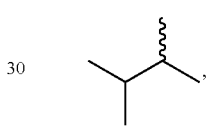

methyl, t-butyl, n-pentyl, and phenyl.

In certain embodiments, $R_2$ is hydrogen. In certain embodiments, $R_2$ is Q-C(O)—, wherein Q is selected from the group consisting of

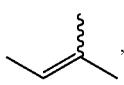

t-butyl, n-pentyl,

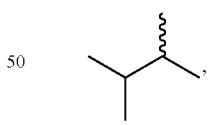

and phenyl.

In certain embodiments, $R_3$ is hydroxyl group. In certain embodiments, $R_3$ is X—C(O)—O—, wherein X is selected from the group consisting of

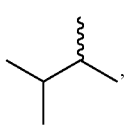

methyl, t-butyl, n-pentyl, and phenyl.

This application specifically relates to the following compounds:

| Name of Compounds | Structure of Compound | Number of Compound |
|---|---|---|
| 13-O-decanoyl-ingenol | | 1a |
| 13-O-(2'E,4'E-decadienoyl)-ingenol | | 1b |
| 20-deoxy-13-O-dodecanoyl-ingenol | | 1d |
| 6,7-epoxy-20-deoxy-ingenol | | 1e |

-continued

| Name of Compounds | Structure of Compound | Number of Compound |
|---|---|---|
| 6,7-epoxy-20-O-(2,3-di-methylbutyryl)-13-O-dodecanoyl-ingenol | | 1f |
| 3-O-angeloyl-13-hydroxy-ingenol | | 3 |
| 13-O-acetyl-ingenol | | 4a |
| 13-O-n-butanoyl-ingenol | | 5 |

-continued

| Name of Compounds | Structure of Compound | Number of Compound |
|---|---|---|
| 13-O-n-hexanoyl-ingenol | | 6 |
| 13-O-n-octanoyl-ingenol | | 7 |
| 3-O-angeloyl-13-O-acetyl-ingenol | | 8 |
| 3-O-acetyl-13-O-dodecanoyl-ingenol | | 10 |

-continued

| Name of Compounds | Structure of Compound | Number of Compound |
|---|---|---|
| 3-O-n-butanoyl-13-O-dodecanoyl-ingenol | | 11 |
| 20-O-acetyl-13-O-dodecanoyl-ingenol | | 12 |
| 20-O-n-butanoyl-13-O-dodecanoyl-ingenol | | 13 |

-continued

| Name of Compounds | Structure of Compound | Number of Compound |
|---|---|---|
| 20-O-(2,3-dimethylbutyryl)-13-O-decanoyl-ingenol | | 14 |
| 20-O-angeloyl-13-O-dodecanoyl-ingenol | | 15b |
| 3,20-O-diangeloyl-13-O-dodecanoyl-ingenol | | 15a |

| Name of Compounds | Structure of Compound | Number of Compound |
|---|---|---|
| 3-O-angeloyl-13-O-butanoyl-ingenol | | 16 |
| 3-O-angeloyl-13-O-hexanoyl-ingenol | | 17 |
| 3-O-angeloyl-13-O-octanoyl-ingenol | | 18 |
| 3-O-angeloyl-13-O-decanoyl-ingenol | | 19 |

-continued

| Name of Compounds | Structure of Compound | Number of Compound |
|---|---|---|
| 3-O-(2,3-dimethylbuten-oyl)-13-O-dodecanoyl-ingenol | | 21 |
| 3-O-(3,5-diethylisoxazo-lyl-4-formyl)-13-O-do-decanoyl-ingenol | | 22 |
| 20-O-tigloyl-13-O-do-decanoyl-ingenol | | |
| 20-O-acetyl-13-hydro-xy-ingenol | | |

| Name of Compounds | Structure of Compound | Number of Compound |
|---|---|---|
| 20-O-aceytl-13-O-acetyl-ingenol | 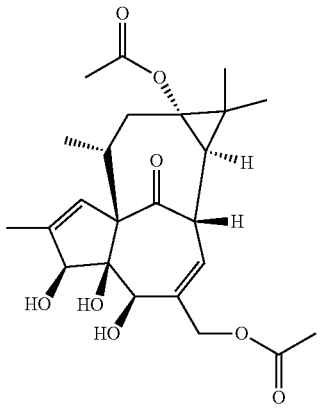 [SMILES: CC(=O)OCC1=C[C@@H]2C(=O)[C@]3(C=C(C)[C@H](O)[C@@]3(O)[C@@H]1O)[C@H](C)C[C@]1(OC(C)=O)[C@H]2C1(C)C] | |
| 20-O-acetyl-13-O-butanoyl-ingenol | 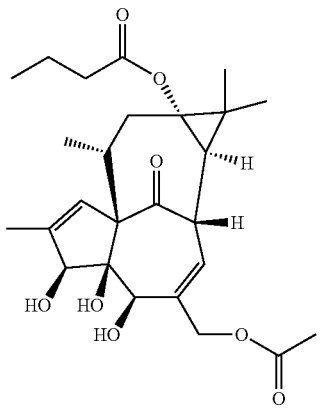 [SMILES: CCCC(=O)O[C@@]12C[C@@H](C)[C@]34C=C(C)[C@H](O)[C@@]3(O)[C@H](O)C(COC(C)=O)=C[C@H](C4=O)[C@@H]1C2(C)C] | |
| 20-O-acetyl-13-O-hexanoyl-ingenol | 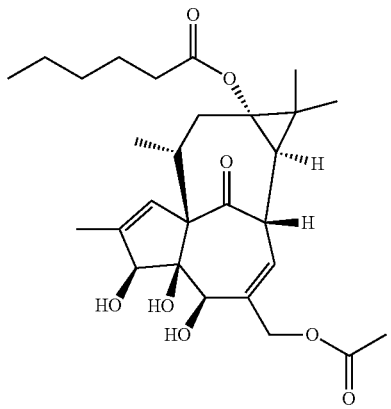 [SMILES: CCCCCC(=O)O[C@@]12C[C@@H](C)[C@]34C=C(C)[C@H](O)[C@@]3(O)[C@H](O)C(COC(C)=O)=C[C@H](C4=O)[C@@H]1C2(C)C] | |

-continued

| Name of Compounds | Structure of Compound | Number of Compound |
|---|---|---|
| 20-O-acetyl-13-O-octanoyl-ingenol | | |
| 20-O-acetyl-13-O-decanoyl-ingenol | | |
| 3-O-acetyl-13-hydroxy-ingenol | | |
| 3-O-acetyl-13-O-acetyl-ingenol | | |

-continued

| Name of Compounds | Structure of Compound | Number of Compound |
|---|---|---|
| 3-O-acetyl-13-O-butanoyl-ingenol | | |
| 3-O-acetyl-13-O-hexanoyl-ingenol | | |
| 3-O-acetyl-13-O-octanoyl-ingenol | | |
| 3-O-acetyl-13-O-decanoyl-ingenol | | |

-continued

| Name of Compounds | Structure of Compound | Number of Compound |
|---|---|---|
| 3-O-butyroyl-13-hydroxy-ingenol | | |
| 3-O-butyroyl-13-O-acetyl-ingenol | | |
| 3-O-butyroyl-13-O-butanoyl-ingenol | | |
| 3-O-butyroyl-13-O-hexanoyl-ingenol | | |

| Name of Compounds | Structure of Compound | Number of Compound |
|---|---|---|
| 3-O-butyroyl-13-O-octanoyl-ingenol | | |
| 3-O-butyroyl-13-O-decanoyl-ingenol | | |
| 3-O-hexanoyl-13-hydroxy-ingenol | | |
| 3-O-hexanoyl-13-O-acetyl-ingenol | | |

-continued

| Name of Compounds | Structure of Compound | Number of Compound |
|---|---|---|
| 3-O-hexanoyl-13-O-butanoyl-ingenol | | |
| 3-O-hexanoyl-13-O-hexanoyl-ingenol | | |
| 3-O-hexanoyl-13-O-octanoyl-ingenol | | |
| 3-O-hexanoyl-13-O-decanoyl-ingenol | | |

-continued
| Name of Compounds | Structure of Compound | Number of Compound |
|---|---|---|
| 3-O-(2,3-dimethylbutyryl)-13-hydroxy-ingenol | 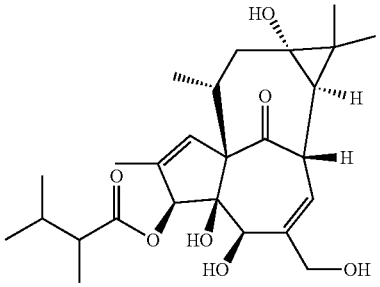 [SMILES: CC1=C[C@]23C(=O)[C@@H](C=C(CO)[C@@H](O)[C@]2(O)[C@H]1OC(=O)C(C)C(C)C)[C@@H]1C(C)(C)[C@]1(O)C[C@H]3C] | |
| 3-O-(2,3-dimethylbutyroyl)-13-O-acetyl-ingenol | 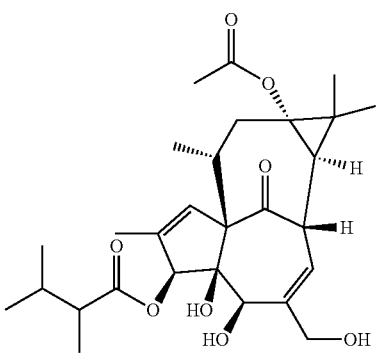 [SMILES: CC(=O)O[C@@]12C[C@@H](C)[C@]34C=C(C)[C@H](OC(=O)C(C)C(C)C)[C@@]3(O)[C@H](O)C(CO)=C[C@H](C4=O)[C@@H]1C2(C)C] | |
| 3-O-(2,3-dimethylbutyryl)-13-O-butanoyl-ingenol | 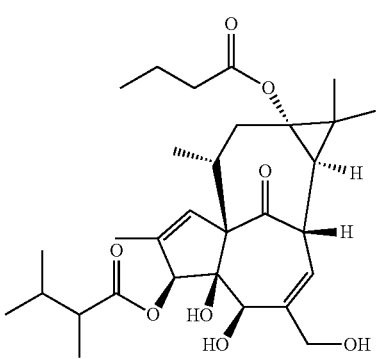 [SMILES: CCCC(=O)O[C@@]12C[C@@H](C)[C@]34C=C(C)[C@H](OC(=O)C(C)C(C)C)[C@@]3(O)[C@H](O)C(CO)=C[C@H](C4=O)[C@@H]1C2(C)C] | |
| 3-O-(2,3-dimethylbutyryl)-13-O-hexanoyl-ingenol | 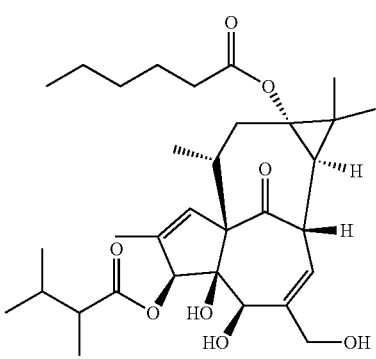 [SMILES: CCCCCC(=O)O[C@@]12C[C@@H](C)[C@]34C=C(C)[C@H](OC(=O)C(C)C(C)C)[C@@]3(O)[C@H](O)C(CO)=C[C@H](C4=O)[C@@H]1C2(C)C] | |

-continued

| Name of Compounds | Structure of Compound | Number of Compound |
|---|---|---|
| 3-O-2,3-dimethylbuten-oyl)-13-hydroxy-ingenol | | |
| 3-O-(2,3-dimethylbutenoyl)-13-O-acetyl-ingenol | | |
| 3-O-2,3-dimethylbutenoyl)-13-O-butanoyl-ingenol | | |
| 3-O-(2,3-dimethylbutenoyl)-13-O-hexanoyl-ingenol | | |

-continued

| Name of Compounds | Structure of Compound | Number of Compound |
|---|---|---|
| 3-O-(2,3-dimethylbutenoyl)-13-O-octanoyl-ingenol | | |
| 3-O-(2,3-dimethylbutenoyl)-13-O-decanoyl-ingenol | | |
| 3-O-trimethylacetyl-13-hydroxy-ingenol | | |
| 3-O-trimethylacetyl-13-O-acetyl-ingenol | | |

-continued

| Name of Compounds | Structure of Compound | Number of Compound |
|---|---|---|
| 3-O-trimethylacetyl-13-O-butanoyl-ingenol | | |
| 3-O-trimethylacetyl-13-O-hexanoyl-ingenol | | |
| 3-O-trimethylacetyl-13-O-octanoyl-ingenol | | |
| 3-O-trimethylacetyl-13-O-decanoyl-ingenol | | |

| Name of Compounds | Structure of Compound | Number of Compound |
|---|---|---|
| 3-O-tigloyl-13-hydroxy-ingenol | | |
| 3-O-tigloyl-13-O-acetyl-ingenol | | |
| 3-O-tigloyl-13-O-butanoyl-ingenol | | |
| 3-O-tigloyl-13-O-hexanoyl-ingenol | | |

| Name of Compounds | Structure of Compound | Number of Compound |
|---|---|---|
| 3-O-tigloyl-13-O-octanoyl-ingenol | | |
| 3-O-tigloyl-13-O-decanoyl-ingenol | | |
| 3-O-tigloyl-13-O-dodecanoyl-ingenol | | 20 |
| 3-O-(3,5-diethylisoxazolyl-4-formyl)-13-hydroxy-ingenol | | |

| Name of Compounds | Structure of Compound | Number of Compound |
|---|---|---|
| 3-O-(3,5-diethylisoxazoolyl-4-formyl)-13-O-acetyl-ingenol | 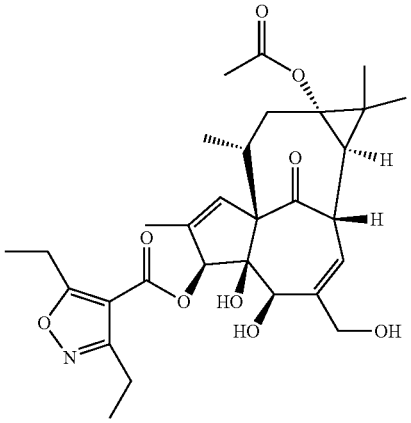 [SMILES: CCc1noc(CC)c1C(=O)O[C@H]1C(C)=C[C@]23C(=O)[C@@H](C=C(CO)[C@@H](O)[C@]12O)[C@@H]1C(C)(C)[C@]1(OC(C)=O)C[C@H]3C] | |
| 3-O-(3,5-diethylisoxazolyl-4-formyl)-13-O-butanoyl-ingenol | 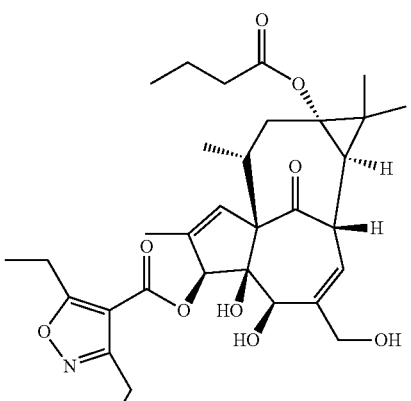 | |
| 3-O-(3,5-diethylisoxazolyl-4-formyl)-13-O-hexanoyl-ingenol | 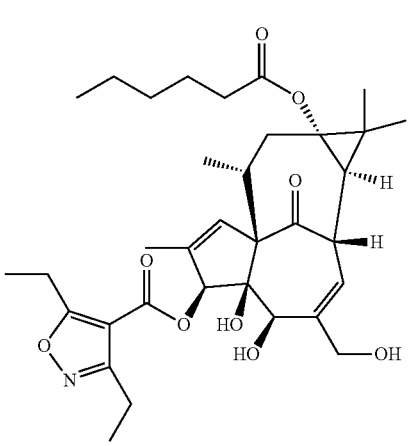 [SMILES: CCCCCC(=O)O[C@@]12C[C@@H](C)[C@]34C=C(C)[C@H](OC(=O)c5c(CC)noc5CC)[C@@]3(O)[C@H](O)C(CO)=C[C@H](C4=O)[C@@H]1C2(C)C] | |

-continued

| Name of Compounds | Structure of Compound | Number of Compound |
|---|---|---|
| 3-O-(3,5-diethylisoxazolyl-4-formyl)-13-O-octanoyl-ingenol | | |
| 3-O-(3,5-diethylisoxazolyl-4-formyl)-13-O-decanoyl-ingenol | | |
| 20-O-buturoyl-13-hydroxy-ingenol | | |

-continued

| Name of Compounds | Structure of Compound | Number of Compound |
|---|---|---|
| 20-O-butyroyl-13-O-acetyl-ingenol | | |
| 20-O-butyroyl-13-O-butanoyl-ingenol | | |
| 20-O-butyroyl-13-O-hexanoyl-ingenol | | |

-continued

| Name of Compounds | Structure of Compound | Number of Compound |
|---|---|---|
| 20-O-butyroyl-13-O-octanoyl-ingenol | | |
| 20-O-butyroyl-13-O-decanoyl-ingenol | | |
| 20-O-hexanoyl-13-hydroxy-ingenol | | |

| Name of Compounds | Structure of Compound | Number of Compound |
|---|---|---|
| 20-O-hexanoyl-13-O-acetyl-ingenol | | |
| 20-O-hexanoyl-13-O-butanoyl-ingenol | | |
| 20-O-hexanoyl-13-O-hexanoyl-ingenol | | |

-continued

| Name of Compounds | Structure of Compound | Number of Compound |
|---|---|---|
| 20-O-hexanoyl-13-O-octanoyl-ingenol | | |
| 20-O-hexanoyl-13-O-decanoyl-ingenol | | |
| 20-O-angeloyl-13-hydroxy-ingenol | | |

| Name of Compounds | Structure of Compound | Number of Compound |
|---|---|---|
| 20-O-angeloyl-13-O-butanoyl-ingenol | | |
| 20-O-angeloyl-13-O-hexanoyl-ingenol | | |
| 20-O-angeloyl-13-O-octanoyl-ingenol | | |

| Name of Compounds | Structure of Compound | Number of Compound |
|---|---|---|
| 20-O-angeloyl-13-O-decanoyl-ingenol | | |
| 20-O-tigloyl-13-hydroxy-ingenol | | |
| 20-O-tigloyl-13-O-acetyl-ingenol | | |

-continued

| Name of Compounds | Structure of Compound | Number of Compound |
|---|---|---|
| 20-O-tigloyl-13-O-butanoyl-ingenol | | |
| 20-O-tigloyl-13-O-hexanoyl-ingenol | | |
| 20-O-tigloyl-13-O-octanoyl-ingenol | | |

-continued

| Name of Compounds | Structure of Compound | Number of Compound |
|---|---|---|
| 20-O-tigloyl-13-O-decanoyl-ingenol | | |
| 20-O-(2,3-dimethylbutyryl)-13-hydroxy-ingenol | | |
| 20-O-(2,3-dimethylbutyryl)-13-O-acetyl-ingenol | | |

-continued

| Name of Compounds | Structure of Compound | Number of Compound |
|---|---|---|
| 20-O-(2,3-dimethylbu-tyryl)-13-O-butanoyl-ingenol | | |
| 20-O-(2,3-dimethylbu-tyryl)-13-O-hexanoyl-ingenol | | |
| 20-O-(2,3-dimethylbu-tyryl)-13-O-octanoyl-ingenol | | |

| Name of Compounds | Structure of Compound | Number of Compound |
|---|---|---|
| 20-O-(2,3-dimethylbutenoyl)-13-hydroxy-ingenol | | |
| 20-O-(2,3-dimethylbutenoyl)-13-O-acetyl-ingenol | | |
| 20-O-(2,3-dimethylbutenoyl)-13-O-butanoyl-ingenol | | |

-continued

| Name of Compounds | Structure of Compound | Number of Compound |
|---|---|---|
| 20-O-(2,3-dimethylbutenoyl)-13-O-hexanoyl-ingenol | | |
| 20-O-(2,3-dimethylbutenoyl)-13-O-octanoyl-ingenol | | |
| 20-O-(2,3-dimethylbutenoyl)-13-O-decanoyl-ingenol | | |

-continued

| Name of Compounds | Structure of Compound | Number of Compound |
|---|---|---|
| 20-O-(2,3-dimethylbutenoyl)-13-O-dodecanoyl-ingenol | | |
| 20-O-trimethylacetyl-13-O-acetyl-ingenol | | |
| 20-O-trimethylacetyl-13-O-butanoyl-ingenol | | |

| Name of Compounds | Structure of Compound | Number of Compound |
|---|---|---|
| 20-O-trimethylacetyl-13-O-hexanoyl-ingenol | | |
| 20-O-trimethylacetyl-13-O-octanoyl-ingenol | | |
| 20-O-trimethylacetyl-13-O-decanoyl-ingenol | | |

| Name of Compounds | Structure of Compound | Number of Compound |
|---|---|---|
| 20-O-(3,5-diethylisoxazolyl-4-formyl)-13-hydroxy-ingenol | | |
| 20-O-(3,5-diethylisoxazolyl-4-formyl)-13-O-acetyl-ingenol | | |
| 20-O-(3,5-diethylisoxazolyl-4-formyl)-13-O-butanoyl-ingenol | | |

-continued

| Name of Compounds | Structure of Compound | Number of Compound |
|---|---|---|
| 20-O-(3,5-diethylisoxazolyl-4-formyl)-13-O-hexanoyl-ingenol | | |
| 20-O-(3,5-diethylisoxazolyl-4-formyl)-13-O-octanoyl-ingenol | | |
| 20-O-(3,5-diethylisoxazolyl-4-formyl)-13-O-decanoyl-ingenol | | |

-continued

| Name of Compounds | Structure of Compound | Number of Compound |
|---|---|---|
| 20-O-(3,5-diethylisoxazolyl-4-formyl)-13-O-dodecanoyl-ingenol | | |
| | and | |
| 13-O-dodecanoyl-ingenol | | 1c |
| 3-O-angeloyl-13-O-dodecanoyl-ingenol | | 9 |
| 3-O-trimethylacetyl-13-O-dodecanoyl-ingenol | | |

-continued

| Name of Compounds | Structure of Compound | Number of Compound |
|---|---|---|
| 3-O-hexanoyl-13-O-dodecanoyl-ingenol | | |
| 3-O-(2,3-dimethylbutyryl)-13-O-dodecanoyl-ingenol | | |
| 20-O-trimethylacetyl-13-O-dodecanoyl-ingenol | | |
| 20-O-(2,3-dimethylbutyryl)-13-O-dodecanoyl-ingenol | | |

-continued
| Name of Compounds | Structure of Compound | Number of Compound |
|---|---|---|
| 20-O-hexanoyl-13-O-dodecanoyl-ingenol | 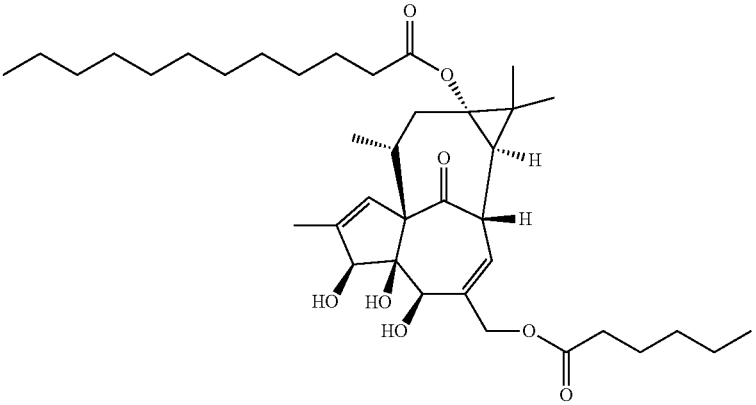 [SMILES: CCCCCCCCCCCC(=O)O[C@@]12C[C@@H](C)[C@]34C=C(C)[C@H](O)[C@@]3(O)[C@H](O)C(COC(=O)CCCCC)=C[C@H](C4=O)[C@@H]1C2(C)C] | |
| 3-O-(2,3-dimethylbutyryl)-13-O-dodecanoyl-20-O-aceytl-ingenol | 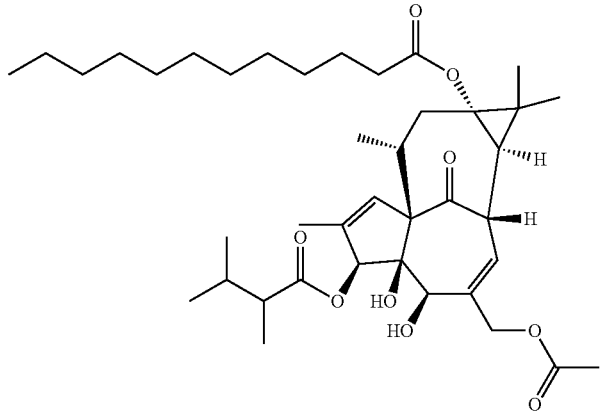 [SMILES: CCCCCCCCCCCC(=O)O[C@@]12C[C@@H](C)[C@]34C=C(C)[C@H](OC(=O)C(C)C(C)C)[C@@]3(O)[C@H](O)C(COC(C)=O)=C[C@H](C4=O)[C@@H]1C2(C)C] | |
| 3-O-(2,3-dimethylbutyryl)-13-O-decanoyl-ingenol | 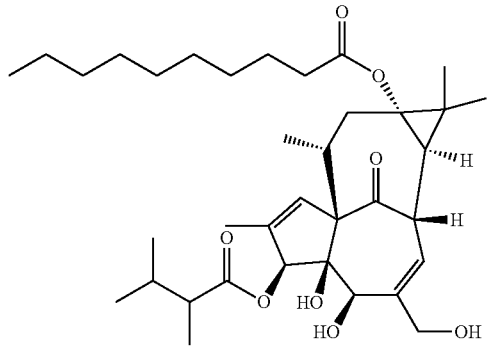 [SMILES: CCCCCCCCCC(=O)O[C@@]12C[C@@H](C)[C@]34C=C(C)[C@H](OC(=O)C(C)C(C)C)[C@@]3(O)[C@H](O)C(CO)=C[C@H](C4=O)[C@@H]1C2(C)C] | |

| Name of Compounds | Structure of Compound | Number of Compound |
|---|---|---|
| 3-O-(2,3-dimethylbutyryl)-13-O-decanoyl-20-O-acetyl-ingenol | | |
| 3-O-(2,3-dimethylbutyryl)-13-O-octanoyl-ingenol | | |
| 3-O-benzoyl-13-O-dodecanoyl-ingenol | | |

| Name of Compounds | Structure of Compound | Number of Compound |
|---|---|---|
| 20-O-benzoyl-13-O-dodecanoyl-ingenol | 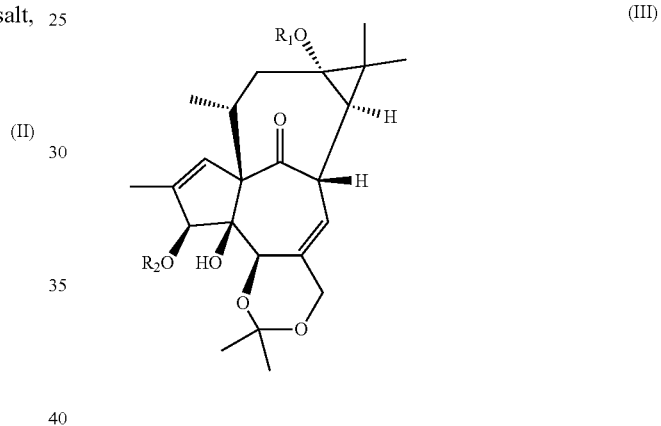 | |

In one aspect, the application also provides a compound of Formula (II), or a pharmaceutically acceptable salt, solvate, prodrug, metabolite or crystal form thereof,

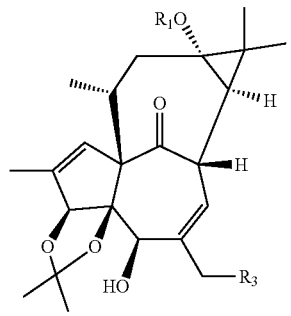

(II)

wherein, $R_1$ and $R_3$ are as defined in any one of the above.

In certain embodiments, $R_1$ is selected from the group consisting of hydrogen and M-C(O)—, wherein M is selected from the group consisting of $C_1$-$C_{11}$ linear alkyl (e.g., methyl, n-propyl, n-pentyl, n-heptyl, n-nonyl, and n-undecyl).

In certain embodiments, $R_3$ is hydroxyl group.

In certain embodiments, the compound is selected from the group consisting of:

13-hydroxy-ingenol 3,4-acetonide
13-O-acetyl-ingenol 3,4-acetonide
13-O-n-butanoyl-ingenol 3,4-acetonide
13-O-n-hexanoyl-ingenol 3,4-acetonide
13-O-n-octanoyl-ingenol 3,4-acetonide
13-O-decanoyl-ingenol 3,4-acetonide
13-O-dodecanoyl-ingenol 3,4-acetonide (2c).

In one aspect, the application also provides a compound of Formula (III), or a pharmaceutically acceptable salt, solvate, prodrug, metabolite or crystal form thereof, (III)

wherein, $R_1$ and $R_2$ are as defined in any one of the above.

In certain embodiments, $R_1$ is selected from the group consisting of hydrogen and M-C(O)—, wherein M is selected from the group consisting of $C_1$-$C_{11}$ linear alkyl (e.g., methyl, n-propyl, n-pentyl, n-heptyl, n-nonyl, and n-undecyl).

In certain embodiments, $R_2$ is selected from the group consisting of hydrogen and Q-C(O)—, wherein Q is selected from the group consisting of methyl, n-propyl, t-butyl, n-pentyl,

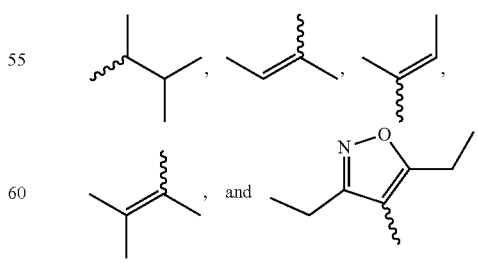

In certain embodiments, $R_2$ is hydrogen. In certain embodiments, $R_2$ is Q-C(O)—, wherein Q is selected from the group consisting of methyl, n-propyl, t-butyl, n-pentyl,

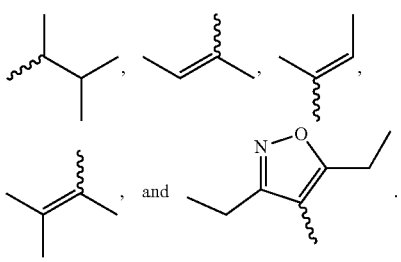

In certain embodiments, when $R_1$ is M-C(O)— and M is n-undecyl, $R_2$ is not hydrogen.

In certain embodiments, when $R_1$ is M-C(O)—, M is n-undecyl, and $R_2$ is Q-C(O)—, Q is not

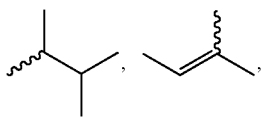

t-butyl, n-pentyl, n-undecyl or phenyl.

Preferably, the compound is selected from the group consisting of:
13-hydroxy-ingenol 5,20-acetonide (33)
13-O-acetyl-ingenol 5,20-acetonide (81)
13-O-n-butanoyl-ingenol 5,20-acetonide
13-O-n-hexanoyl-ingenol 5,20-acetonide
13-O-n-octanoyl-ingenol 5,20-acetonide
13-O-decanoyl-ingenol 5,20-acetonide
3-O-angeloyl-13-hydroxy-ingenol 5,20-acetonide (34)
3-O-angeloyl-13-O-acetyl-ingenol 5,20-acetonide (82)
3-O-angeloyl-13-O-n-butanoyl-ingenol 5,20-acetonide
3-O-angeloyl-13-O-n-hexanoyl-ingenol 5,20-acetonide
3-O-angeloyl-13-O-n-octanoyl-ingenol 5,20-acetonide
3-O-angeloyl-13-O-decanoyl-ingenol 5,20-acetonide
3-O-acetyl-13-O-dodecanoyl-ingenol 5,20-acetonide
3-O-n-butanoyl-13-O-dodecanoyl-ingenol 5,20-acetonide
3-O-tigloyl-13-O-dodecanoyl-ingenol 5,20-acetonide
3-O-(2,3-dimethylbutenoyl)-13-O-dodecanoyl-ingenol 5,20-acetonide
3-O-(3,5-diethylisoxazolyl-4-formyl)-13-O-dodecanoyl-ingenol 5,20-acetonide.

In one aspect, the application also provides a compound of Formula (IV), or a pharmaceutically acceptable salt, solvate, prodrug, metabolite or crystal form thereof,

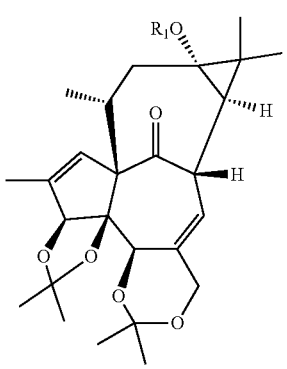

(IV)

wherein, $R_1$ is as defined in any one of the above.

In certain embodiments, $R_1$ is M-C(O)—, wherein M is selected from the group consisting of $C_1$-$C_{10}$ linear alkyl.

In certain embodiments, the compound is selected from the group consisting of:
13-O-acetyl-ingenol 3,4,5,20-diacetonide (41)
13-O-n-butanoyl-ingenol 3,4,5,20-diacetonide (51)
13-O-n-hexanoyl-ingenol 3,4,5,20-diacetonide (61)
13-O-n-octanoyl-ingenol 3,4,5,20-diacetonide (71)
13-O-decanoyl-ingenol 3,4,5,20-diacetonide.

In another aspect, the present application relates to a pharmaceutical composition comprising a compound as described above, or a pharmaceutically acceptable salt, solvate, prodrug, metabolite or crystal form thereof, as well as a pharmaceutically acceptable carrier (for example, an excipient, a disintegrant, a binder, an absorption enhancer, a flavoring agent or a surfactant). The pharmaceutical composition may be formulated into any pharmaceutically acceptable dosage form including, but not limited to, tablet, capsule, granule, pill, powder, solution, suspension, aerosol, dispersion, emulsion, gel, and ointment, etc. The dosage form can be an immediate release, sustained release or controlled release dosage form.

The pharmaceutical composition of the present invention may also be administered to a subject in need thereof by any suitable administration mode (for example, orally, parenterally, intravenously, intraarterially, intraperitoneally, transdermally, sublingually, rectally, intramuscularly, transbuccally, intranasally, inhalation, vaginally, subcutaneously, intralipidly, intraocularly, intraarticularly, intrathecally, liposome, topical application to the skin, and intratumoral injection, etc.). For oral administration, the pharmaceutical composition can be prepared into a conventional solid preparation such as tablet, capsule, pill, and granule, etc.; or it can also be prepared into an oral liquid preparation such as oral solution, oral suspension and syrup, etc. When an oral preparation is prepared, a suitable filler, a binder, a disintegrant, and a lubricant, etc., may be added. For parenteral administration, the pharmaceutical composition can be prepared into an injection, including an injection solution, a sterile powder for injection, and a concentrated solution for injection. When an injection is prepared, it can be produced by a conventional method in the prior art, and when an injection is formulated, an additive may not be added, or a suitable additive may be added depending on the nature of the drug. For rectal administration, the pharmaceutical composition can be formulated as a suppository, etc. For pulmonary administration, the pharmaceutical composition can be formulated as an inhalant or a spray, etc.

In another aspect, the present application relates to use of a compound as described above, or a pharmaceutically acceptable salt, solvate, prodrug, metabolite or crystal form thereof for the manufacture of a medicament for the prevention and/or treatment of a cosmetic indication or a disease associated with proliferation or tumor in a subject.

In certain embodiments, the cosmetic indication is selected from the group consisting of skin phototrauma, seborrheic keratosis, and keloids.

In certain embodiments, the disease associated with proliferation or tumor is selected from the group consisting of cutaneous wart, genital wart, porokeratosis, lung cancer, gastric cancer, breast cancer, colon cancer, bladder cancer, leukemia, liver cancer, cervical cancer, lymphoma, malignant melanoma, basal cell carcinoma, squamous cell carcinoma, Merkel cell carcinoma, vaginal cancer, vulvar cancer, and a precancerous lesion, including solar keratosis, malignant freckle, cervical intraepithelial neoplasia, anal intraepithelial neoplasia, and vulvar intraepithelial neoplasia.

The present application also relates to use of a compound as described above, or a pharmaceutically acceptable salt, solvate, prodrug, metabolite or crystal form thereof for the manufacture of a medicament for facilitating the healing of a skin wound, or for the prevention and/or treatment of the following disease in a subject: a disease responsive to neutrophil oxidative burst, a disease responsive to a release of IL-8 by keratinocyte, or a disease responsive to induction of necrosis.

In certain embodiments, the wound is a wound associated with diabetes or a wound caused by pathogenic infection.

In certain embodiments, the disease is selected from the group consisting of: viral infectious dermatosis, including verruca vulgaris, verruca plana, molluscum contagiosum, genital warts; skin cancers, including malignant melanoma, basal cell carcinoma, squamous cell carcinoma, Merkel cell carcinoma, vaginal cancer, and vulvar cancer; and a precancerous lesion of skin, including solar keratosis, malignant freckle, cervical intraepithelial neoplasia, anal intraepithelial neoplasia, and vulvar intraepithelial neoplasia.

The present application also relates to the use of a compound as described above, or a pharmaceutically acceptable salt, solvate, prodrug, metabolite or crystal form thereof for the preparation of a formulation for inhibiting proliferation of a cell associated with proliferation or a tumor, for stimulating neutrophil oxidative burst, or for stimulating a release of IL-8 by keratinocyte.

In certain embodiments, the proliferation or tumor is selected from the group consisting of cutaneous wart, genital wart, porokeratosis, lung cancer, gastric cancer, breast cancer, colon cancer, bladder cancer, leukemia, liver cancer, cervical cancer, lymphoma, malignant melanoma, basal cell carcinoma, squamous cell carcinoma, Merkel cell carcinoma, vaginal cancer, vulvar cancer, and a precancerous lesion, including solar keratosis, malignant freckle, cervical intraepithelial neoplasia, anal intraepithelial neoplasia, and vulvar intraepithelial neoplasia.

In another aspect, the present application relates to a method for the prevention and/or treatment of a cosmetic indication or a disease associated with proliferation or tumor in a subject, the method comprises administering to a subject in need thereof an effective amount of a compound as described above, or a pharmaceutically acceptable salt, solvate, prodrug, metabolite or crystal form thereof.

In certain embodiments, the cosmetic indication is selected from the group consisting of skin phototrauma, seborrheic keratosis, and keloids.

In certain embodiments, the disease associated with proliferation or tumor is selected from the group consisting of cutaneous wart, genital wart, porokeratosis, lung cancer, gastric cancer, breast cancer, colon cancer, bladder cancer, leukemia, liver cancer, cervical cancer, lymphoma, malignant melanoma, basal cell carcinoma, squamous cell carcinoma, Merkel cell carcinoma, vaginal cancer, vulvar cancer, and a precancerous lesion, including solar keratosis, malignant freckle, cervical intraepithelial neoplasia, anal intraepithelial neoplasia, and vulvar intraepithelial neoplasia.

The present application also relates to a method for facilitating the healing of a skin wound, or for the prevention and/or treatment of the following diseases in a subject: a disease responsive to neutrophil oxidative burst, a disease responsive to a release of IL-8 by keratinocyte, or a disease responsive to induction of necrosis, wherein the method comprises administering to a subject in need thereof an effective amount of a compound as described above, or a pharmaceutically acceptable salt, solvate, prodrug, metabolite or crystal form thereof.

In certain embodiments, the wound is a wound associated with diabetes or a wound caused by pathogenic infection.

In certain embodiments, the disease is selected from the group consisting of: viral infectious dermatosis, including verruca vulgaris, verruca plana, molluscum contagiosum, genital warts; skin cancers, including malignant melanoma, basal cell carcinoma, squamous cell carcinoma, Merkel cell carcinoma, vaginal cancer, and vulvar cancer; and a precancerous lesion of skin, including solar keratosis, malignant freckle, cervical intraepithelial neoplasia, anal intraepithelial neoplasia, and vulvar intraepithelial neoplasia.

The present application also relates to a method capable of inhibiting proliferation of a cell associated with proliferation or a tumor, stimulating neutrophil oxidative burst, and/or stimulating a release of IL-8 by keratinocyte, the method comprises administering to a cell in need thereof an effective amount of a compound as described above, or a pharmaceutically acceptable salt, solvate, prodrug, metabolite or crystal form thereof.

In certain embodiments, the proliferation or tumor is selected from the group consisting of cutaneous wart, genital wart, porokeratosis, lung cancer, gastric cancer, breast cancer, colon cancer, bladder cancer, leukemia, liver cancer, cervical cancer, lymphoma, malignant melanoma, basal cell carcinoma, squamous cell carcinoma, Merkel cell carcinoma, vaginal cancer, vulvar cancer, and a precancerous lesion, including solar keratosis, malignant freckle, cervical intraepithelial neoplasia, anal intraepithelial neoplasia, and vulvar intraepithelial neoplasia.

In certain embodiments, the cell associated with proliferation or a tumor, the neutrophil or the keratinocyte is a primary cell from a subject or a culture thereof, or an established cell line.

In the present invention, the subject may be any animals, preferably mammals, such as a bovine, an equid, a caprid, a porcine, a canid, a felid, a rodent, and a primate. Among them, the particularly preferred subject is human.

The present invention also provides various exemplary methods for preparing the compounds of Formula (I), as shown in Schemes 1, 2, and 3, respectively:

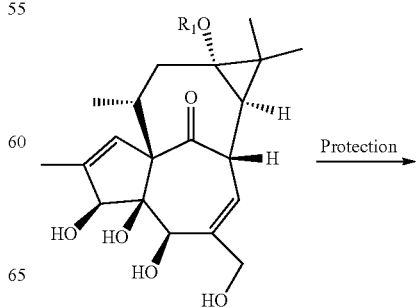

Scheme 1

105
-continued
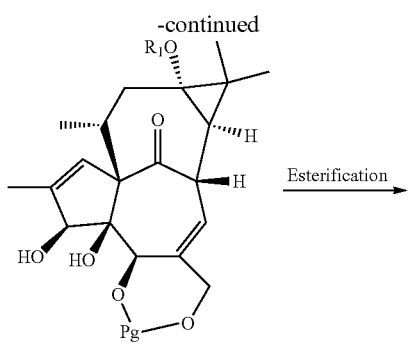
→ Esterification
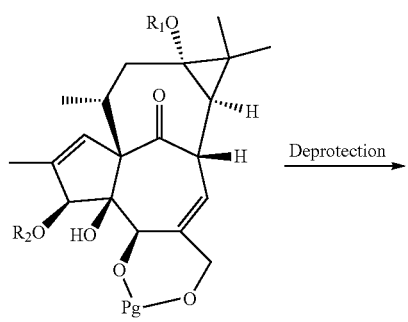
→ Deprotection
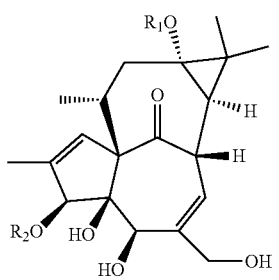
Scheme 2
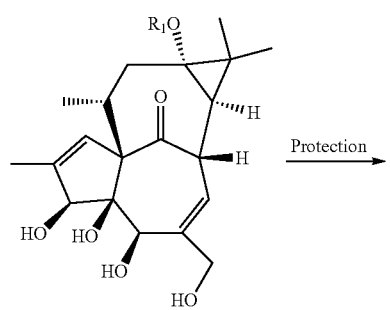
→ Protection
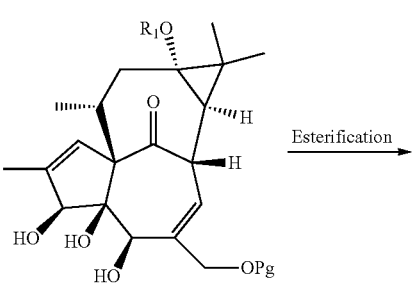
→ Esterification
106
-continued
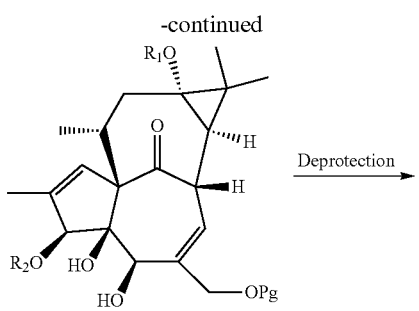
→ Deprotection
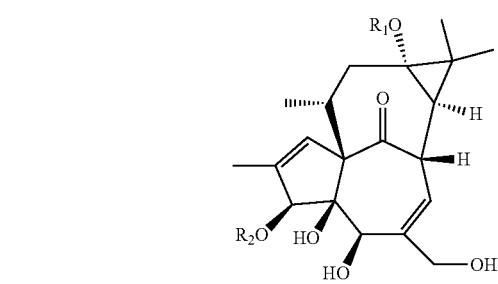
Scheme 3
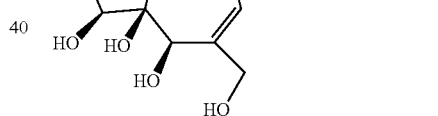
→ Esterification
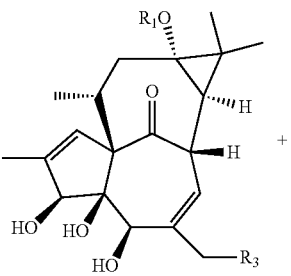
+
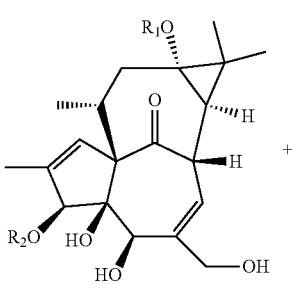
+

-continued

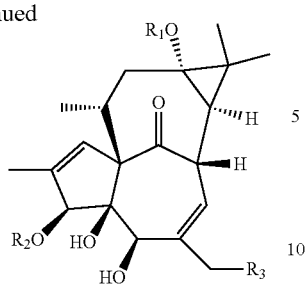

In the present invention, the 13-oxidized ingenol 3-O-acylate can be synthesized according to, for example, the method of Scheme 1, 2 or 3. Wherein, the protecting group (Pg) may be a protecting group for hydroxyl commonly used in organic chemistry. For example, in the Scheme 1, the Pg may be an acetal or a ketal, etc., and in the Scheme 2, the Pg may be a silyl group or a trityl group, or a tetrahydropyran, and the like. The esterification reaction in Scheme 1, 2 or 3 may be carried out by an esterification reaction commonly used in organic synthesis, for example, a reaction carried out using an acid, an acid anhydride, a mixed acid anhydride or an acid halide as an acylating agent, and in the presence of an acidic or basic catalyst in a suitable solvent. The deprotection reaction in Scheme 1, 2 or 3 can be carried out using the deprotection reaction conditions for an acetal, a ketal, a silyl, a trityl or a tetrahydropyran, etc., which are commonly used in organic synthesis.

The starting synthetic materials in Scheme 1, 2 or 3 can be obtained from *Euphorbia* (e.g., *kansui* L., *Leptochloa chinensis.*, *Euphorbia cornigera*, *Euphorbia cyparissias* L., *uphorbia papillosa*, etc.) by a conventional method such as alcohol extraction, alkali hydrolysis or column chromatography.

The starting synthetic materials in Scheme 1, 2, or 3 can also be prepared according to the following non-limiting general methods.

Scheme a

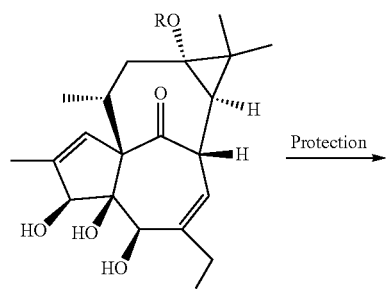

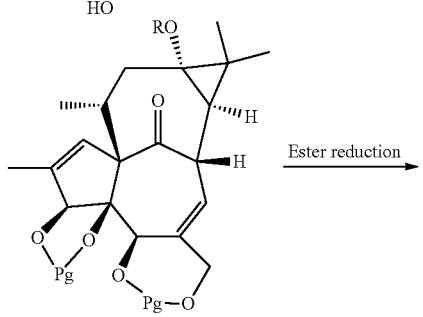

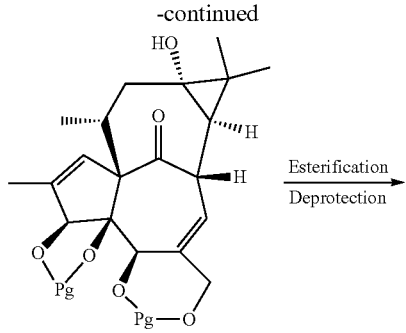

Scheme b

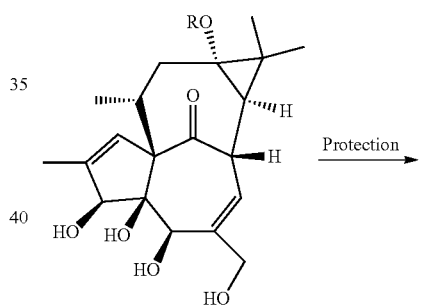

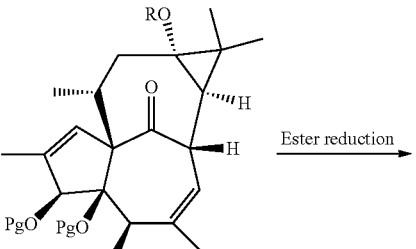

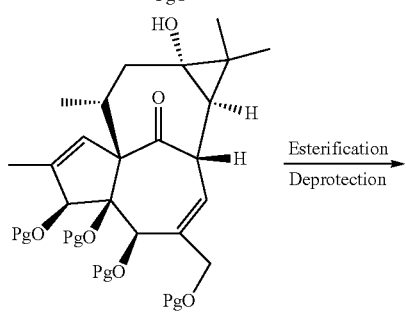

-continued

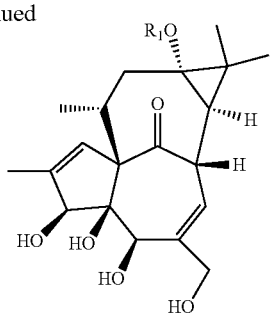

In the Scheme a or b, R represents an aliphatic acyl group or a benzoyl group, and when R is an aliphatic acyl group, it may be selected from the group consisting of acetyl, n-octanoyl, decanoyl, dodecanoyl, 2E,4E-decadienoyl, 2Z,4E,6Z-decatrienoyl.

The starting synthetic materials in Scheme a or b can be obtained from Euphorbia (e.g., kansui L., Leptochloa chinensis., Euphorbia cornigera, Euphorbia cyparissias L., Euphorbia papillosa, etc.) by a conventional method such as alcohol extraction, alkali hydrolysis or column chromatography.

In Scheme a or b, the protecting group (Pg) may be a protecting group for hydroxyl commonly used in organic chemistry. For example, in the Scheme a, the Pg may be an acetal or a ketal, etc., and in the Scheme b, the Pg may be a methyl, a silyl group, a trityl group, or a tetrahydropyran, and the like. The ester reduction reaction in the Scheme a or b may be carried out by an ester reduction reaction commonly used in organic synthesis, for example, an ester reduction reaction using lithium aluminum hydride, diisobutylaluminum hydride, vitride, sodium borohydride/Lewis acid or lithium borohydride as a reducing agent in a suitable solvent. The esterification reaction in Scheme a or b may be carried out by an esterification reaction commonly used in organic synthesis, for example, an esterification reaction using an acid, an acid anhydride, a mixed acid anhydride or an acid halide as an acylating agent, in the presence of an acidic or basic catalyst in a suitable solvent. The deprotection reaction in Scheme a or b can be carried out using the deprotection reaction conditions for an acetal, a ketal, a methyl, a silyl, a trityl or a tetrahydropyran, etc., which are commonly used in organic synthesis.

Beneficial Technical Effects of the Invention

The compounds of the present invention have one or more of the following beneficial effects compared to the prior art:

1. The compounds of the present invention can induce rapid death of a variety of tumor cells, and some compounds exhibit high selectivity for leukemia cells.

2. The compounds of the present invention can stimulate neutrophil oxidative burst and are more effective than 3-O-angeloyl-ingenol. Neutrophils are an important component of the innate immune response and, therefore, the compounds of the present invention can stimulate an innate immune response.

3. The compounds of the present invention can stimulate the release of IL-8 by keratinocytes and are as efficient as 3-O-angeloyl-ingenol or higher than 3-O-angeloyl-ingenol. IL-8 is a chemokine of neutrophils, whereby the compounds of the present invention can induce immune stimulation.

4. The compounds of the present invention are less polar than 3-O-angeloyl-ingenol and are more accessible to the dermis layer than 3-O-angeloyl-ingenol.

SPECIFIC EMBODIMENTS

Exemplary embodiments for some of the compounds of the invention are provided below to demonstrate the advantageous activity and beneficial technical effects of the compounds of the invention. However, it should be understood that the following experimental schemes are merely illustrative of the present invention and are not intended to limit the scope of the invention. A person skilled in the art can make appropriate modifications or changes to the technical solutions of the present invention with the teachings of the present description without departing from the spirit and scope of the present invention.

Examples wherein the specific conditions are not specified are carried out according to the conventional conditions or conditions suggested by manufacturer. The reagents or instruments used wherein the manufacturers are not indicated, are all commercially available conventional products.

Example 1 Preparation of 13-O-decanoyl-ingenol (Compound 1a), 13-O-(2'E,4'E-decadienoyl)-ingenol (Compound 1b) and 13-O-dodecanoyl-ingenol (Compound 1c), 20-O-deoxy-13-O-dodecanoyl-ingenol (Compound 1d), 6,7-epoxy-20-deoxy-ingenol (Compound 1e), 6,7-epoxy-20-O-(2,3-dimethylbutyryl)-13-O-dodecanoyl-ingenol (Compound 1f)

20 kg of kansui L. medicinal herbs was cold-soak extracted by 3 to 6 folds amount of 95% ethanol, until complete extraction; the extracting solutions were combined, and concentrated under reduced pressure until an alcohol-free taste to obtain an extract. To the extract, 10 folds amount of a solution of NaOH in methanol (0.5 M) was added, the mixture was stirred for about 2 hours. The mixture was adjusted to pH about 7 with dilute hydrochloric acid, and extracted 3 times with ethyl acetate, and then the ethyl acetate layers were combined, concentrated under reduced pressure to dryness. The extract was purified by normal phase silica gel column chromatography eluted with a gradient of petroleum ether: ethyl acetate (100:1 to 1:2) to obtain fractions rich in 13-oxidized ingenol and fractions rich in deoxy-ingenol, respectively. The fractions rich in 13-oxidized ingenol were purified by reverse-phase silica gel column chromatography, eluted with a gradient of methanol: water (10% methanol to 100% methanol), and the same fractions were combined to obtain 13-O-decanoyl-ingenol (Compound 1a), 13-O-(2'E,4'E-decadienoyl)-ingenol (Compound 1b), 13-O-dodecanoyl-ingenol (Compound 1c), and 6,7-epoxy-20-O-(2,3-dimethylbutyryl)-13-O-dodecanoyl-ingenol (Compound 1f).

The fractions rich in deoxy-ingenol were purified by normal phase silica gel column chromatography eluted with a gradient of petroleum ether:acetone (20:1 to 1:2), and the same fractions were combined to obtain 20-O-deoxy-13-O-dodecanoyl-ingenol (Compound 1d), and 6,7-epoxy-20-deoxy-ingenol (Compound 1e).

The structural formula and hydrogen nuclear magnetic resonance spectrum ($^1$H-NMR) of the compounds are as follows:

1) 13-O-decanoyl-ingenol (Compound 1a)

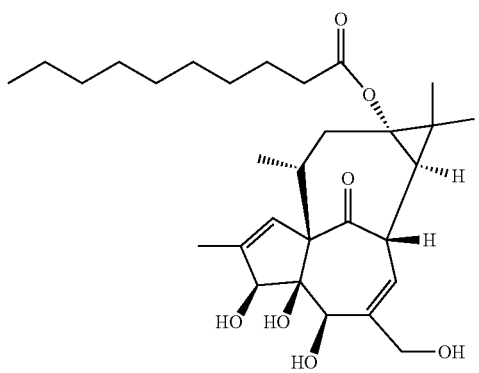 [SMILES: CCCCCCCCCC(=O)O[C@@]12C[C@@H](C)[C@]34C=C(C)[C@H](O)[C@@]3(O)[C@H](O)C(CO)=C[C@H](C4=O)[C@@H]1C2(C)C]

¹H-NMR (400 MHz, CDCl₃) δ 6.02 (d, 1H), 5.88 (d, 1H), 4.39 (d, 1H), 4.02-4.21 (m, 4H), 3.83 (d, 1H), 3.59 (d, 1H), 3.25 (brs, 1H), 2.73 (brd, 1H), 2.46 (m, 1H), 2.15-2.22 (m, 3H), 1.85 (s, 3H), 1.55 (m, 2H), 1.25-1.29 (m, 13H), 1.22 (s, 3H), 1.07 (s, 3H), 0.96 (d, 3H), 0.88 (t, 3H).

2) 13-O-(2'E,4'E-decadienoyl)-ingenol (Compound 1b)

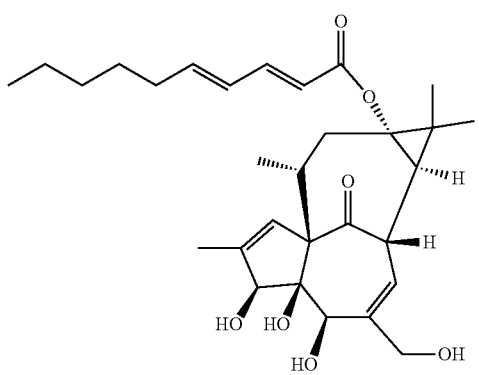 [SMILES: CCCCC/C=C/C=C/C(=O)O[C@@]12C[C@@H](C)[C@]34C=C(C)[C@H](O)[C@@]3(O)[C@H](O)C(CO)=C[C@H](C4=O)[C@@H]1C2(C)C]

¹H-NMR (400 MHz, CDCl₃) δ 7.20 (m, 1H), 6.12-6.14 (m, 2H), 6.03 (d, 1H), 5.90 (s, 1H), 5.71 (d, 1H), 4.41 (brs, 1H), 4.05-4.22 (m, 4H), 3.84 (brs, 1H), 3.57 (brs, 1H), 3.13 (brs, 1H), 2.76 (d, 1H), 2.58 (brs, 1H), 2.45 (brs, 1H), 2.24 (dd, 1H), 2.15 (m, 2H), 1.86 (s, 3H), 1.42 (m, 2H), 1.24-1.29 (m, 8H), 1.08 (s, 3H), 0.96 (d, 3H), 0.89 (t, 3H).

3) 13-O-dodecanoyl-ingenol (Compound 1c)

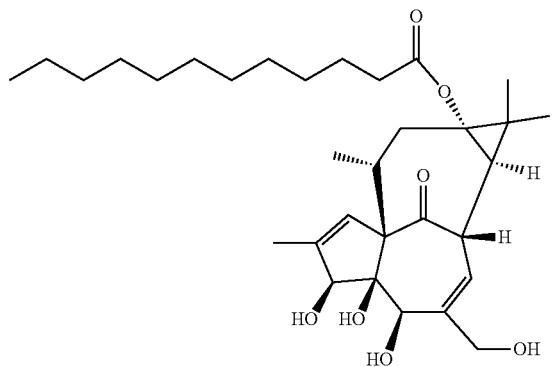 [SMILES: CCCCCCCCCCCC(=O)O[C@@]12C[C@@H](C)[C@]34C=C(C)[C@H](O)[C@@]3(O)[C@H](O)C(CO)=C[C@H](C4=O)[C@@H]1C2(C)C]

¹H-NMR (400 MHz, CDCl₃) δ 6.01 (d, 1H), 5.85 (brs, 1H), 4.37 (s, 1H), 4.24 (brs, 1H), 4.17 (d, 1H), 4.08 (d, 1H), 4.05 (dd, 1H), 3.82 (brs, 1H), 2.72 (m, 1H), 2.46 (m, 1H), 2.19 (t, 2H), 2.15 (m, 1H), 1.84 (s, 3H), 1.54 (m, 2H), 1.20-1.29 (m, 20H), 1.06 (s, 3H), 0.94 (d, 3H), 0.87 (t, 3H).

4) 20-deoxy-13-O-dodecanoyl-ingenol (Compound 1d)

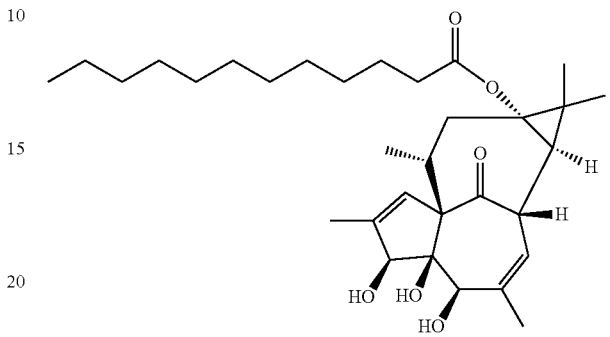

¹H-NMR (400 MHz, CDCl₃) δ 5.94 (s, 1H), 5.70 (d, 1H), 4.40 (brs, 1H), 4.15 (s, 1H), 3.96 (brd, 1H), 3.46 (d, 1H), 2.93 (brd, 1H), 2.66-2.74 (m, 2H), 2.36 (m, 1H), 2.17-2.23 (m, 3H), 1.85 (s, 3H), 1.77 (s, 3H), 1.54 (m, 2H), 1.22-1.24 (m, 17H), 1.21 (s, 3H), 1.05 (s, 3H), 0.96 (d, 3H), 0.87 (t, 3H).

5) 6,7-epoxy-20-deoxy-ingenol (Compound 1e)

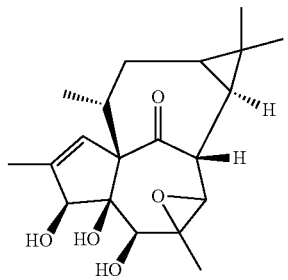

¹H-NMR (400 MHz, CDCl₃) δ 5.96 (d, 1H), 4.28 (s, 1H), 3.26-3.32 (m, 2H), 3.16 (ddd, 1H), 2.26 (m, 1H), 2.16 (m, 1H), 1.82 (s, 3H), 1.70 (m, 1H), 1.41 (s, 3H), 1.18 (s, 3H), 1.07 (s, 3H), 0.93 (d, 3H), 0.86 (m, 1H), 0.69 (m, 1H).

6) 6,7-epoxy-20-O-(2,3-dimethylbutyryl)-13-O-dodecanoyl-ingenol (Compound 1f)

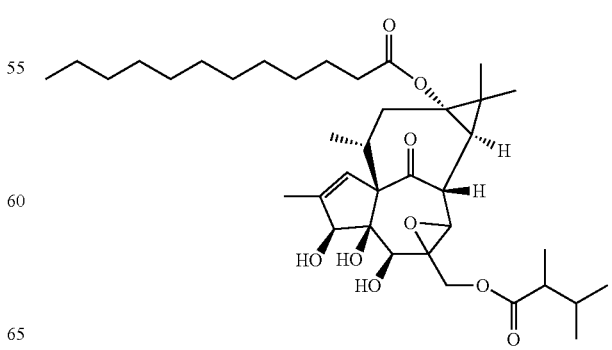

$^1$H-NMR (400 MHz, CDCl$_3$) δ 5.97 (d, 1H), 4.41 (d, 1H), 4.33 (brs, 1H), 4.00 (s, 1H), 3.98 (d, 1H), 3.52 (brd, 1H), 3.46 (d, 1H), 3.11 (dd, 1H), 2.74 (m, 1H), 2.62 (m, 1H), 2.16-2.29 (m, 4H), 1.84-1.91 (m, 4H), 1.55 (m, 2H), 1.18-1.31 (m, 20H), 1.08 (t, 9H), 0.85-0.95 (m, 9H).

Example 2 Preparation of 13-O-dodecanoyl-ingenol acetonide

13-O-dodecanoyl-ingenol (0.2 mmol) was dissolved in 0.5 mg/mL of a solution of p-toluenesulfonic acid monohydrate in acetone and stirred at 30° C. for 12 h. The reaction solution was concentrated to dryness under reduced pressure, re-dissolved in ethyl acetate, and washed with water and saturated aqueous sodium chloride solution, successively, and then the organic layer was concentrated to dryness under reduced pressure. The resulting residual was purified by flash chromatography (petroleum ether: ethyl acetate=10:1 to 6:4) to obtain 13-O-dodecanoyl-ingenol 3,4,5,20-diacetonide (Compound 2a), 13-O-dodecanoyl-ingenol 5,20-acetonide (Compound 2b), 13-O-dodecanoyl-ingenol 3,4-acetonide (Compound 2c), respectively.

The structural formula and hydrogen nuclear magnetic resonance spectrum ($^1$H-NMR) of the compounds are as follows:

1) 13-O-dodecanoyl-ingenol 3,4,5,20-diacetonide (Compound 2a)

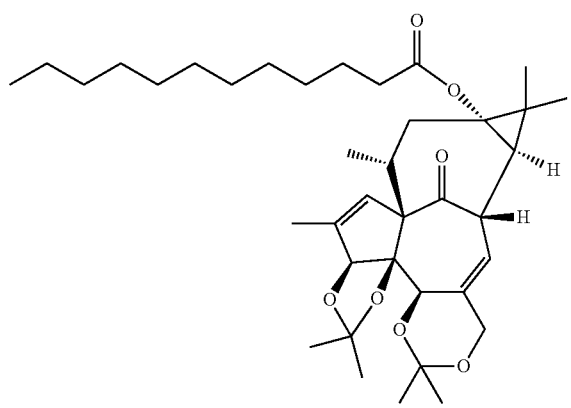 [SMILES: CCCCCCCCCCCC(=O)O[C@@]12C[C@@H](C)[C@]34C=C(C)[C@@H]5OC(C)(C)O[C@@]53[C@@H]3OC(C)(C)OCC3=C[C@H](C4=O)[C@@H]1C2(C)C]

$^1$H-NMR (400 MHz, CDCl$_3$) δ 5.93 (d, 1H), 5.67 (d, 1H), 4.86 (s, 1H), 4.25 (dd, 1H), 4.10 (d, 1H), 3.93 (s, 1H), 3.54 (brd, 1H), 2.72 (dd, 1H), 2.61 (dt, 1H), 2.21 (t, 2H), 2.10 (dd, 1H), 1.86 (s, 3H), 1.51-1.58 (m, 8H), 1.40 (s, 3H), 1.32 (s, 3H), 1.23-1.30 (m, 17H), 1.21 (s, 3H), 1.06 (s, 3H), 0.98 (d, 3H), 0.87 (t, 3H).

2) 13-O-dodecanoyl-ingenol 5,20-acetonide (Compound 2b)

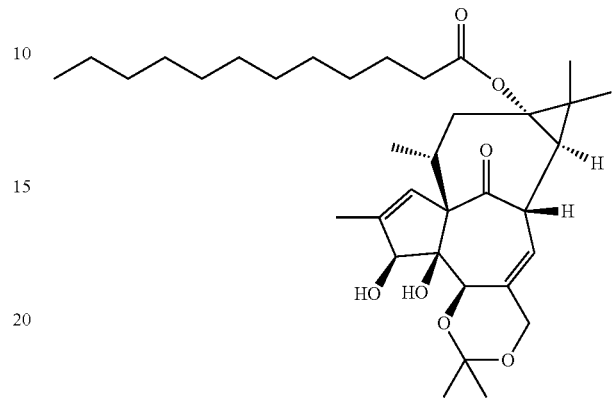

$^1$H-NMR (400 MHz, CDCl$_3$) δ 5.89 (d, 1H), 5.77 (d, 1H), 4.28 (d, 1H), 4.18 (s, 2H), 4.04 (brd, 1H), 3.94 (s, 1H), 3.55 (s, 1H), 2.74 (dd, 1H), 2.59 (dt, 1H), 2.53 (d, 1H), 2.20 (t, 2H), 2.15 (dd, 1H), 1.86 (s, 3H), 1.55 (m, 2H), 1.41 (s, 3H), 1.36 (s, 3H), 1.25 (brs, 17H), 1.23 (s, 3H), 1.07 (s, 3H), 0.95 (d, 3H), 0.87 (t, 3H).

3) 13-O-dodecanoyl-ingenol 3,4-acetonide (Compound 2c)

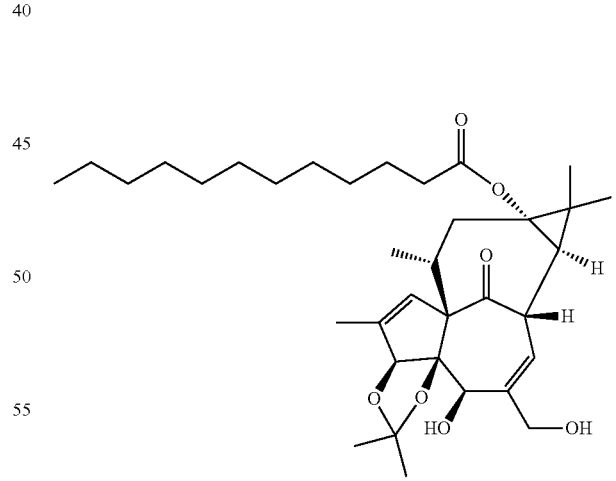

$^1$H-NMR (400 MHz, CDCl$_3$) δ 6.09 (d, 1H), 5.75 (d, 1H), 4.77 (s, 1H), 4.10-4.17 (m, 4H), 3.22 (d, 1H), 2.73-2.79 (m, 2H), 2.20 (t, 2H), 1.95 (m, 1H), 1.86 (s, 3H), 1.54 (s, 5H), 1.49 (s, 3H), 1.22-1.31 (m, 20H), 1.08 (s, 3H), 1.01 (d, 3H), 0.88 (t, 3H).

Example 3 Preparation of 3-O-angeloyl-13-hydroxy-ingenol (Compound 3)

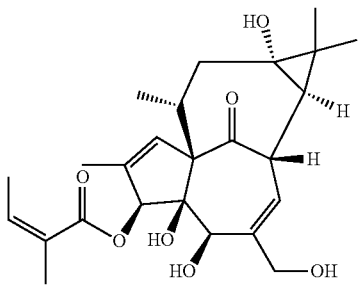 [SMILES: C/C=C(/C)C(=O)O[C@H]1C(C)=C[C@]23C(=O)[C@@H](C=C(CO)[C@@H](O)[C@]12O)[C@@H]1C(C)(C)[C@]1(O)C[C@H]3C]

13-O-dodecanoyl-ingenol 3,4,5,20-diacetonide (Compound 2a, for which the preparation procedure may refer to Example 2) (0.5 mmol) was dissolved in diethyl ether, and lithium aluminium hydride was added in the condition of ice water bath and stirred for 15 min. The reaction solution was added with a saturated aqueous sodium sulfate solution, and extracted with diethyl ether. The organic layer was washed with saturated aqueous sodium chloride solution, and then concentrated to dryness under reduced pressure. The resulting residual was purified by flash chromatography (petroleum ether: ethyl acetate=7:3) to obtain 13-OH-ingenol 3,4,5,20-diacetonide (Compound 31).

Compound 31 (0.4 mmol) was dissolved in methanol, 4 M diluted hydrochloric acid was added and stirred at room temperature for 15 h. The reaction solution was poured into water, adjusted to pH about 7 with sodium hydrogen carbonate solution, and extracted with ethyl acetate. The organic layer was washed with saturated aqueous sodium chloride solution, and then concentrated to dryness under reduced pressure. The resulting residual was purified by flash chromatography (petroleum ether:acetone=3:2) to obtain 13-OH-ingenol (Compound 32).

Compound 32 (0.3 mmol) was dissolved in 0.5 mg/mL of a solution of p-toluenesulfonic acid monohydrate in acetone and stirred at room temperature for 1 h. The reaction solution was concentrated to dryness under reduced pressure, re-dissolved in ethyl acetate, and washed with water and saturated aqueous sodium chloride solution, successively, and then the organic layer was concentrated to dryness under reduced pressure. The resulting residual was purified by flash chromatography (petroleum ether:acetone=3:1) to obtain 13-OH-ingenol 5,20-acetonide (Compound 33).

Compound 33 (0.2 mmol) was dissolved in acetonitrile, angelic anhydride (0.24 mmol), and cesium carbonate (0.3 mmol) were added, and stirred at room temperature for 24 h. The reaction solution was poured into water, extracted with diethyl ether. The organic layer was washed with saturated aqueous sodium chloride solution, and then concentrated to dryness under reduced pressure. The resulting residual was purified by flash chromatography (petroleum ether:acetone=7:1) to obtain 3-O-angeloyl-13-OH-ingenol 5,20-acetonide (Compound 34).

Compound 34 (0.1 mmol) was dissolved in methanol, 4 M diluted hydrochloric acid was added and stirred at room temperature for 8 h. The reaction solution was poured into water, extracted with ethyl acetate. The organic layer was washed with saturated aqueous sodium chloride solution, and then concentrated to dryness under reduced pressure. The resulting residual was purified by flash chromatography (petroleum ether:acetone=2:1) to obtain the title compound (Compound 3).

The hydrogen nuclear magnetic resonance spectrum of Compound 3: $^1$H-NMR (400 MHz, Acetone-d6) δ 6.11 (dq, 1H), 6.00 (d, 1H), 5.93 (brd, 1H), 5.82 (s, 1H), 4.10-4.15 (m, 3H), 3.95 (s, 1H), 2.79 (m, 1H), 2.68 (dd, 1H), 1.97 (m, 3H), 1.86-1.92 (m, 4H), 1.78 (d, 3H), 1.16 (s, 3H), 1.10 (d, 3H), 1.07 (s, 3H), 0.96 (d, 1H).

Example 4 Preparation of 13-O-acetyl-ingenol (Compound 4a)

Method 1:

50 kg of dry aboveground part of *Euphorbia cornigera* was cold-soak extracted by 3 to 6 folds amount of 95% ethanol, until complete extraction, the extracting solutions were combined, and concentrated under reduced pressure until an alcohol-free taste to obtain an extract. To the extract, 10 folds amount of a solution of NaOH in methanol (0.5 M) was added, the mixture was stirred for about 2 hours. The mixture was adjusted to pH about 7 with dilute hydrochloric acid, and extracted with ethyl acetate for 3 times, and then the ethyl acetate layers were combined, and concentrated under reduced pressure to dryness. The extract was purified by normal phase silica gel column chromatography eluted with a gradient of petroleum ether: ethyl acetate (100:1 to 1:2) to obtain fractions rich in 13-oxidized ingenol. The fractions were further purified by reverse-phase silica gel column chromatography eluted with a gradient of acetonitrile: water (10% acetonitrile to 100% acetonitrile), and the same fractions were combined to obtain 13-O-acetyl-ingenol (Compound 4a), 13-O-(2'Z,4'E,6'Z-decatrienoyl)-ingenol (Compound 4b) and 13-O-dodecanoyl-ingenol (Compound 1c), respectively.

Method 2:

13-OH-ingenol 3,4,5,20-diacetonide (Compound 31, for which the preparation procedure may refer to Example 3) (0.4 mmol) was dissolved in anhydrous pyridine, and acetic anhydride (0.5 mmol) was added and stirred at 50° C. for 24 h. The reaction solution was poured into ice water, adjusted to pH about 7 with sodium hydrogen carbonate solution, and extracted with diethyl ether. The organic layer was washed with saturated aqueous sodium chloride solution, and then concentrated to dryness under reduced pressure. The resulting residual was purified by flash chromatography (petroleum ether: ethyl acetate=10:1) to obtain 13-O-acetyl-ingenol 3,4,5,20-diacetonide (Compound 41).

Compound 41 (0.25 mmol) was dissolved in methanol, 4 M diluted hydrochloric acid was added and stirred at room temperature for 15 h. The reaction solution was poured into water, adjusted to pH about 7 with sodium hydrogen carbonate solution, and extracted with ethyl acetate. The organic layer was washed with saturated aqueous sodium chloride solution, and then concentrated to dryness under reduced pressure. The resulting residual was purified by flash chromatography (chloroform:methanol=94:6) to obtain 13-O-acetyl-ingenol (Compound 4a). The structural formula and hydrogen nuclear magnetic resonance spectrum are as follows:

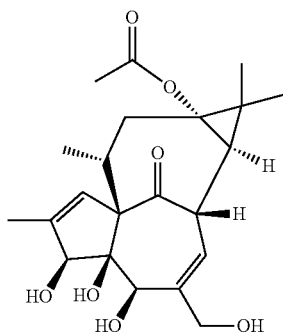

$^1$H-NMR (400 MHz, CDCl$_3$) δ 6.01 (d, 1H), 5.84 (d, 1H), 4.37 (d, 1H), 4.23 (s, 1H), 4.03-4.18 (m, 3H), 3.81 (d, 1H), 3.68-3.71 (m, 2H), 2.93 (m, 1H), 2.72 (dd, 1H), 2.47 (m, 1H), 2.15 (dd, 1H), 1.96 (s, 3H), 1.84 (d, 3H), 119-1.24 (m, 4H), 1.08 (s, 3H), 0.95 (d, 3H).

Example 5 Preparation of 13-O-n-butanoyl-ingenol (Compound 5)

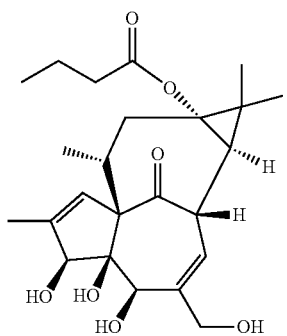

13-O-n-butanoyl-ingenol 3,4,5,20-diacetonide (Compound 51) was prepared according to the preparation method of 13-O-acetyl-ingenol 3,4,5,20-diacetonide (Compound 41) (refer to Example 4), except that acetic anhydride was replaced with n-butyric anhydride.

Using Compound 51 as a raw material, the acetonide-protecting group was removed according to the preparation procedure of Compound 4a to obtain 13-O-n-butanoyl-ingenol (Compound 5).

The hydrogen nuclear magnetic resonance spectrum of Compound 5: $^1$H-NMR (400 MHz, CDCl$_3$) δ 6.02 (d, 1H), 5.88 (d, 1H), 4.39 (d, 1H), 4.03-4.20 (m, 4H), 3.82 (d, 1H), 3.54 (d, 1H), 3.16 (d, 1H), 2.73 (dd, 1H), 2.58 (m, 1H), 2.45 (m, 1H), 2.14-2.25 (m, 3H), 1.85 (s, 3H), 1.59 (m, 2H), 1.24 (d, 1H), 1.22 (s, 3H), 1.07 (s, 3H), 0.96 (d, 3H), 0.92 (t, 3H).

Example 6 Preparation of 13-O-n-hexanoyl-ingenol (Compound 6)

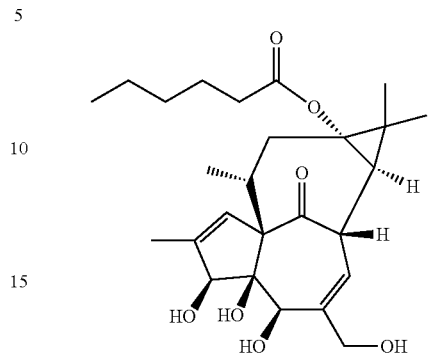

13-O-n-hexanoyl-ingenol 3,4,5,20-diacetonide (Compound 61) was prepared according to the preparation method of 13-O-acetyl-ingenol 3,4,5,20-diacetonide (Compound 41) (refer to Example 4), except that acetic anhydride was replaced with n-hexanoic anhydride.

Using Compound 61 as a raw material, the acetonide-protecting group was removed according to the preparation method of Compound 4a to obtain 13-O-n-hexanoyl-ingenol (Compound 6).

The hydrogen nuclear magnetic resonance spectrum of Compound 6: $^1$H-NMR (400 MHz, CDCl$_3$) δ 6.00 (d, 1H), 5.84 (d, 1H), 4.35 (d, 1H), 4.25 (s, 1H), 4.03-4.18 (m, 3H), 3.85 (d, 1H), 3.76-3.82 (m, 2H), 3.08 (m, 1H), 2.72 (dd, 1H), 2.46 (m, 1H), 2.10-2.22 (m, 3H), 1.84 (s, 3H), 1.55 (m, 2H), 1.23-1.30 (m, 5H), 1.21 (s, 3H), 1.06 (s, 3H), 0.94 (d, 3H), 0.87 (t, 3H).

Example 7 Preparation of 13-O-n-octanoyl-ingenol (Compound 7)

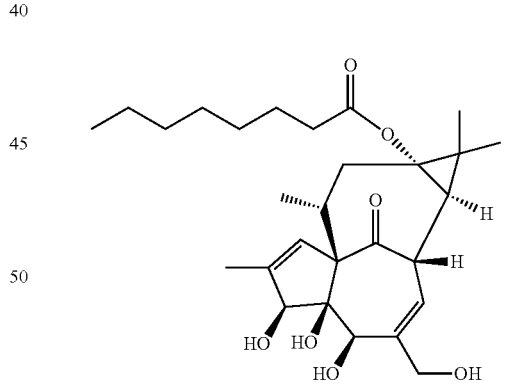

13-O-n-octanoyl-ingenol 3,4,5,20-diacetonide (Compound 71) was prepared according to the preparation method of 13-O-acetyl-ingenol 3,4,5,20-diacetonide (Compound 41) (refer to Example 4), except that acetic anhydride was replaced with n-octanoic anhydride.

Using Compound 71 as a raw material, the acetonide-protecting group was removed according to the preparation method of Compound 4a to obtain 13-O-n-octanoyl-ingenol (Compound 7).

The hydrogen nuclear magnetic resonance spectrum of Compound 7: $^1$H-NMR (400 MHz, CDCl$_3$) δ 6.00 (d, 1H), 5.84 (d, 1H), 4.36 (d, 1H), 4.24 (s, 1H), 4.03-4.18 (m, 3H), 3.73-3.82 (m, 3H), 3.00 (brs, 1H), 2.72 (brd, 1H), 2.46 (m, 1H), 2.11-2.21 (m, 3H), 1.84 (s, 3H), 1.54 (m, 2H), 1.22-1.32 (m, 9H), 1.21 (s, 3H), 1.06 (s, 3H), 0.94 (d, 3H), 0.86 (t, 3H).

Example 8 Preparation of 3-O-angeloyl-13-O-acetyl-ingenol (Compound 8)

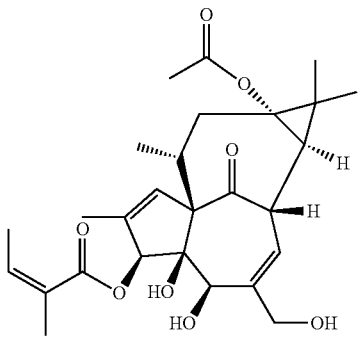 [SMILES: C/C=C(/C)C(=O)O[C@H]1C(C)=C[C@]23C(=O)[C@@H](C=C(CO)[C@@H](O)[C@]12O)[C@@H]1C(C)(C)[C@]1(OC(C)=O)C[C@H]3C]

13-O-acetyl-ingenol (Compound 4a, for which the preparation procedure may refer to Example 4) (0.5 mmol) was dissolved in 0.4 mg/mL of a solution of p-toluenesulfonic acid monohydrate in acetone and stirred at room temperature for 1 h. The reaction solution was concentrated to dryness under reduced pressure, re-dissolved in ethyl acetate, and washed with water and saturated aqueous sodium chloride solution, successively, and then the organic layer was concentrated to dryness under reduced pressure. The resulting residual was purified by flash chromatography (petroleum ether: ethyl acetate=2:1) to obtain 13-O-acetyl-ingenol 5,20-acetonide (Compound 81).

Compound 81 (0.4 mmol) was dissolved in acetonitrile, angelic anhydride (0.6 mmol), and cesium carbonate (0.6 mmol) were added, and stirred at room temperature for 24 h. The reaction solution was poured into water, extracted with diethyl ether. The organic layer was washed with saturated aqueous sodium chloride solution, and then concentrated to dryness under reduced pressure. The resulting residual was purified by flash chromatography (petroleum ether: ethyl acetate=8:1) to obtain 3-O-angeloyl-13-O-acetyl-ingenol 5,20-acetonide (Compound 82).

Compound 82 (0.3 mmol) was dissolved in methanol, 4 M diluted hydrochloric acid was added and stirred at room temperature for 12 h. The reaction solution was poured into water and extracted with ethyl acetate. The organic layer was washed with saturated aqueous sodium chloride solution, and then concentrated to dryness under reduced pressure. The resulting residual was purified by flash chromatography (petroleum ether:acetone=4:1) to obtain the title compound (Compound 8).

The hydrogen nuclear magnetic resonance spectrum of Compound 8: $^1$H-NMR (400 MHz, CDCl$_3$) δ 6.17 (dq, 1H), 6.01-6.05 (m, 2H), 5.53 (s, 1H), 4.43 (brs, 1H), 4.16 (brs, 2H), 4.07-4.11 (m, 2H), 3.56 (s, 1H), 2.72 (dd, 1H), 2.65 (m, 1H), 2.45 (brs, 1H), 2.19 (m, 1H), 2.01 (dd, 3H), 1.96 (s, 3H), 1.91 (m, 3H), 1.81 (d, 3H), 1.24 (d, 1H), 1.19 (s, 3H), 1.08 (s, 3H), 0.97 (d, 3H).

Example 9 Preparation of 3-O-angeloyl-13-O-dodecanoyl-ingenol (Compound 9)

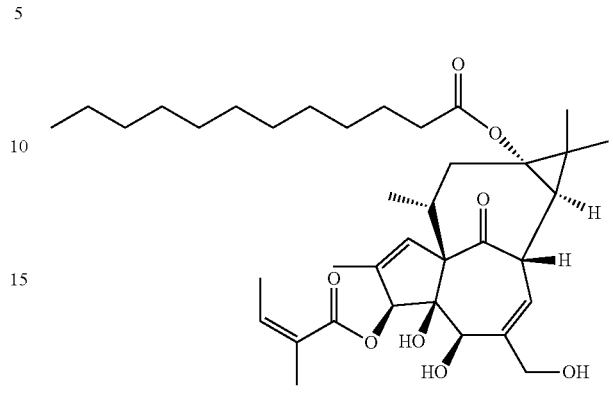

Using 13-O-dodecanoyl-ingenol (Compound 1c, for which the preparation method may refer to Example 1) as raw material, acetonide protection reaction, esterification reaction, and the reaction of removing acetonide-protecting group were carried out in sequence according to the synthesis method of Compound 8 to obtain the title Compound (Compound 9).

The hydrogen nuclear magnetic resonance spectrum of Compound 9: $^1$H-NMR (400 MHz, CDCl$_3$) δ 6.17 (dq, 1H), 6.02-6.04 (m, 2H), 5.53 (s, 1H), 4.34 (d, 1H), 4.16 (d, 2H), 4.08-4.11 (m, 2H), 3.54 (s, 1H), 2.73 (dd, 1H), 2.65 (m, 1H), 2.32 (t, 1H), 2.16-2.22 (m, 3H), 2.01 (dd, 3H), 1.91 (s, 3H), 1.81 (s, 3H), 1.60 (s, 2H), 1.55 (m, 2H), 1.22-1.28 (m, 15H), 1.19 (s, 3H), 1.06 (s, 3H), 0.97 (d, 3H), 0.88 (t, 3H).

Example 10 Preparation of 3-O-acetyl-13-O-dodecanoyl-ingenol (Compound 10)

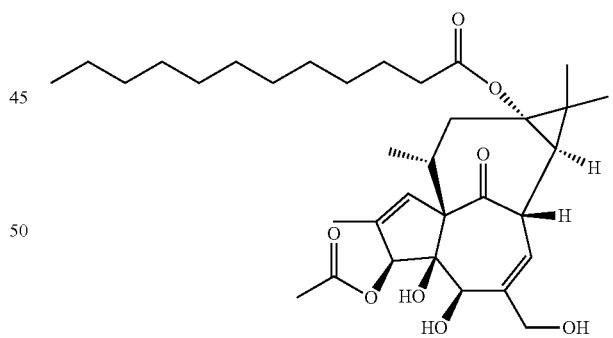

Using 13-O-dodecanoyl-ingenol (Compound 1c, for which the preparation method may refer to Example 1) as a starting material, according to the synthesis method in Example 8, 13-O-dodecanoyl-ingenol 5,20-acetonide was synthesized and then angelic anhydride was replaced with acetic anhydride to synthesize 3-O-acetyl-13-O-dodecanoyl-ingenol 5,20-acetonide, and the acetonide-protecting group was removed to obtain the title Compound (Compound 10).

The hydrogen nuclear magnetic resonance spectrum of Compound 10: $^1$H-NMR (400 MHz, CDCl$_3$) δ 6.01-6.03 (m, 2H), 5.47 (s, 1H), 4.32 (d, 1H), 3.98-4.16 (m, 4H), 3.58 (s, 1H), 2.71 (dd, 1H), 2.60 (m, 1H), 2.47 (t, 1H), 2.16-2.24 (m, 3H), 2.15 (s, 3H), 1.78 (s, 3H), 1.55 (m, 2H), 1.21-1.33 (m, 17H), 1.19 (s, 3H), 1.06 (s, 3H), 0.97 (d, 3H), 0.87 (t, 3H).

Example 11 Preparation of 3-O-n-butanoyl-13-O-dodecanoyl-ingenol (Compound 11)

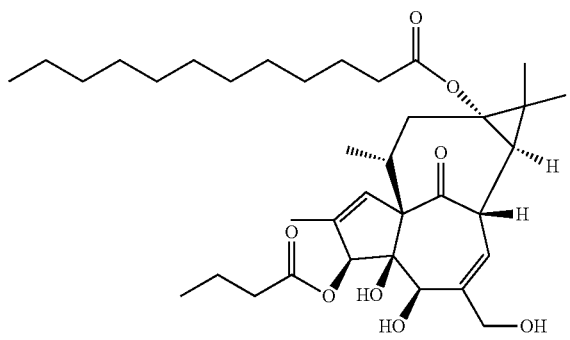 [SMILES: CCCCCCCCCCCC(=O)O[C@@]12C[C@@H](C)[C@]34C=C(C)[C@H](OC(=O)CCC)[C@@]3(O)[C@H](O)C(CO)=C[C@H](C4=O)[C@@H]1C2(C)C]

Using 13-O-dodecanoyl-ingenol (Compound 1c, for which the preparation method may refer Example 1) as a starting material, according to the synthesis method in Example 8, 13-O-dodecanoyl-ingenol 5,20-acetonide was synthesized, and then angelic anhydride was replaced with butyric anhydride to synthesize 3-O-n-butanoyl-13-O-dodecanoyl-ingenol 5,20-acetonide, and the acetonide-protecting group was removed to obtain the title Compound (Compound 11).

The hydrogen nuclear magnetic resonance spectrum of Compound 11: $^1$H-NMR (400 MHz, CDCl$_3$) δ 6.01-6.03 (m, 2H), 5.46 (s, 1H), 4.34 (d, 1H), 4.02-4.18 (m, 4H), 3.55 (s, 1H), 2.71 (dd, 1H), 2.60 (m, 1H), 2.47 (m, 1H), 2.38 (dt, 2H), 2.16-2.24 (m, 3H), 1.78 (s, 3H), 1.63-1.72 (m, 2H), 1.55 (m, 2H), 1.20-1.33 (m, 17H), 1.19 (s, 3H), 1.06 (s, 3H), 0.96-1.00 (m, 6H), 0.87 (t, 3H).

Example 12 Preparation of 20-O-acetyl-13-O-dodecanoyl-ingenol (Compound 12)

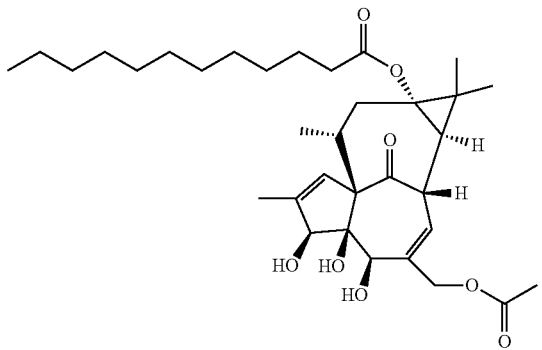 [SMILES: CCCCCCCCCCCC(=O)O[C@@]12C[C@@H](C)[C@]34C=C(C)[C@H](O)[C@@]3(O)[C@H](O)C(COC(C)=O)=C[C@H](C4=O)[C@@H]1C2(C)C]

13-O-dodecanoyl-ingenol (Compound 1c, for which the preparation method may refer to Example 1) (0.06 mmol) was dissolved in dichloromethane, acetic anhydride (0.06 mmol) and 4-dimethylaminopyridine (0.06 mmol) were added, and stirred at room temperature for 8 h. The reaction solution was poured into water, extracted with diethyl ether. The organic layer was washed with saturated aqueous sodium chloride solution, and then concentrated to dryness under reduced pressure. The resulting residual was purified by flash chromatography (petroleum ether:acetone=4:1) to obtain the title compound (Compound 12).

The hydrogen nuclear magnetic resonance spectrum of Compound 12: $^1$H-NMR (400 MHz, CDCl$_3$) δ 6.07 (d, 1H), 5.92 (d, 1H), 4.71 (d, 1H), 4.52 (d, 1H), 4.45 (d, 1H), 4.12 (s, 1H), 4.03 (dd, 1H), 3.69 (d, 1H), 2.91 (d, 1H), 2.73 (dd, 1H), 2.65 (d, 1H), 2.42 (m, 1H), 2.16-2.22 (m, 3H), 2.06 (s, 3H), 1.86 (s, 3H), 1.55 (m, 2H), 1.23-1.29 (m, 17H), 1.22 (s, 3H), 1.07 (s, 3H), 0.97 (d, 3H), 0.88 (t, 3H).

Example 13 Preparation of 20-O-n-butanoyl-13-O-dodecanoyl-ingenol (Compound 13)

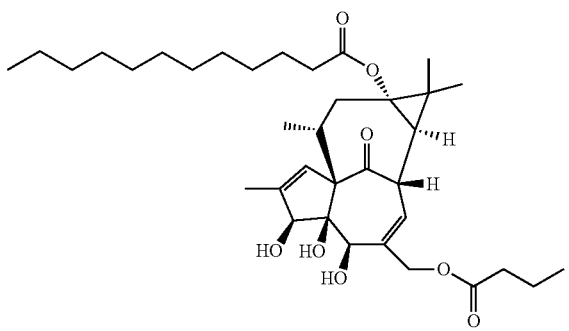 [SMILES: CCCCCCCCCCCC(=O)O[C@@]12C[C@@H](C)[C@]34C=C(C)[C@H](O)[C@@]3(O)[C@H](O)C(COC(=O)CCC)=C[C@H](C4=O)[C@@H]1C2(C)C]

13-O-dodecanoyl-ingenol (Compound 1c, for which the preparation method may refer to Example 1) (0.07 mmol) was dissolved in dichloromethane, n-butyric anhydride (0.08 mmol) and 4-dimethylaminopyridine (0.08 mmol) were added, and stirred at room temperature for 8 h. The reaction solution was poured into water, extracted with diethyl ether. The organic layer was washed with saturated aqueous sodium chloride solution, and then concentrated to dryness under reduced pressure. The resulting residual was purified by flash chromatography (petroleum ether:acetone=5:1) to obtain the title compound (Compound 13).

The hydrogen nuclear magnetic resonance spectrum of Compound 13: $^1$H-NMR (400 MHz, CDCl$_3$) δ 6.07 (brd, 1H), 5.91 (s, 1H), 4.73 (d, 1H), 4.53 (d, 1H), 4.44 (d, 1H), 4.09 (s, 1H), 4.03 (m, 1H), 3.69 (brd, 1H), 2.95 (d, 1H), 2.73 (brd, 1H), 2.61 (d, 1H), 2.43 (m, 1H), 2.29 (t, 2H), 2.17-2.22 (m, 3H), 1.86 (s, 3H), 1.55 (m, 2H), 1.22-1.29 (m, 19H), 1.21 (s, 3H), 1.07 (s, 3H), 0.86-0.98 (m, 9H).

Example 14 Preparation of 20-O-(2,3-dimethylbutyryl)-13-O-decanoyl-ingenol (Compound 14)

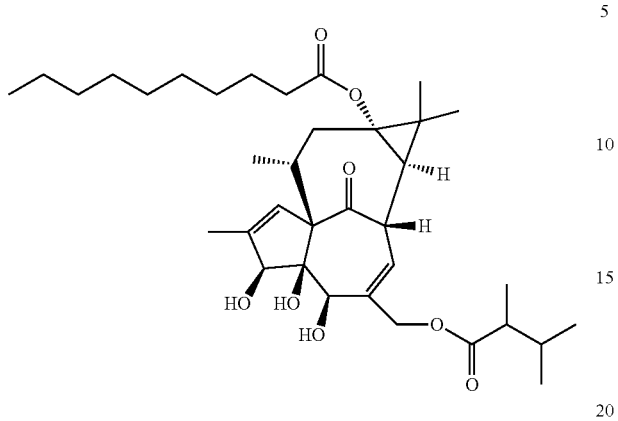

13-O-decanoyl-ingenol (Compound 1a, for which the preparation method may refer to Example 1) (0.06 mmol) was dissolved in dichloromethane, and 2,3-dimethylbutyric acid (0.06 mmol), N,N'-dicyclohexylcarbodiimide (0.08 mmol) and 4-dimethylaminopyridine (0.08 mmol) were added in the condition of ice water bath, then stirred at 20° C. for 32 h. The reaction solution was poured into water, extracted with diethyl ether. The organic layer was washed with saturated aqueous sodium chloride solution, and then concentrated to dryness under reduced pressure. The resulting residual was purified by flash chromatography (petroleum ether:acetone=4:1) to obtain the desired compound (Compound 14).

The hydrogen nuclear magnetic resonance spectrum of Compound 14: $^1$H-NMR (400 MHz, CDCl$_3$) δ 6.08 (d, 1H), 5.89 (d, 1H), 4.72 (d, 1H), 4.53 (d, 1H), 4.43 (s, 1H), 4.03 (dd, 1H), 3.66 (d, 1H), 2.72 (dd, 1H), 2.43 (m, 1H), 2.15-2.28 (m, 4H), 1.89 (m, 1H), 1.84 (s, 3H), 1.55 (m, 2H), 1.23-1.28 (m, 13H), 1.20 (s, 3H), 1.08 (d, 3H), 1.07 (s, 3H), 0.96 (d, 3H), 0.86-0.90 (m, 9H).

Example 15 Preparation of 3,20-O-diangeloyl-13-O-dodecanoyl-ingenol (Compound 15a) and 20-O-angeloyl-13-O-dodecanoyl-ingenol (Compound 15b)

13-O-dodecanoyl-ingenol (Compound 1c, for which the preparation procedure may refer to Example 1) (0.06 mmol) was dissolved in acetonitrile, angelic anhydride (0.08 mmol) and cesium carbonate (0.08 mmol) were added, and stirred at room temperature for 30 h. The reaction solution was poured into water, extracted with diethyl ether. The organic layer was washed with saturated aqueous sodium chloride solution, and then concentrated to dryness under reduced pressure. The resulting residual was purified by flash chromatography (petroleum ether:acetone=12:1 to 6:1), to obtain 3,20-O-diangeloyl-13-O-dodecanoyl-ingenol (Compound 15a), and 20-O-angeloyl-13-O-dodecanoyl-ingenol (Compound 15b), respectively.

1) 3,20-O-diangeloyl-13-O-dodecanoyl-ingenol (Compound 15a)

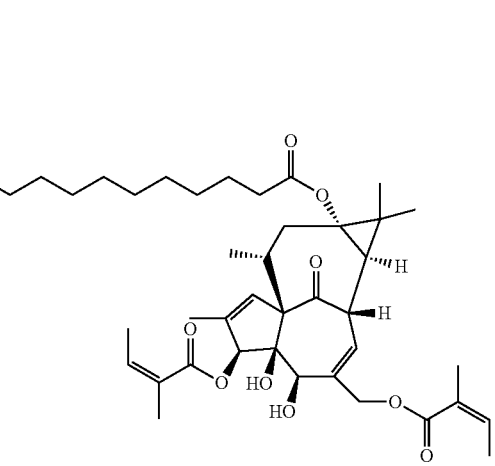

$^1$H-NMR (400 MHz, CDCl$_3$) δ 6.04-6.20 (m, 4H), 5.55 (s, 1H), 4.86 (d, 1H), 4.57 (d, 1H), 4.08 (dd, 1H), 3.92 (d, 1H), 3.77 (d, 1H), 3.53 (s, 1H), 2.72 (dd, 1H), 2.62 (m, 1H), 2.18-2.25 (m, 3H), 2.01 (dd, 3H), 1.90-1.95 (m, 6H), 1.88 (brs, 3H), 1.80 (brs, 3H), 1.56 (m, 2H), 1.24-1.28 (m, 17H), 1.18 (s, 3H), 1.06 (s, 3H), 0.98 (d, 3H), 0.88 (t, 3H).

2) 20-O-angeloyl-13-O-dodecanoyl-ingenol (Compound 15b)

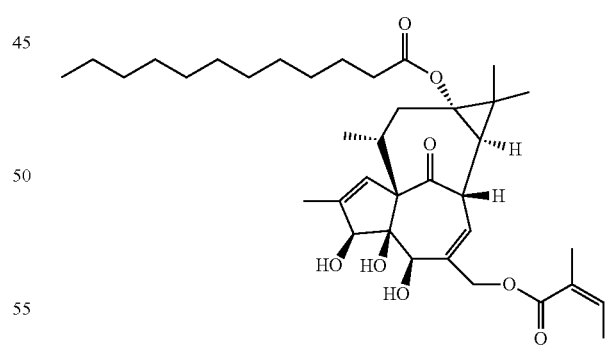

$^1$H-NMR (400 MHz, CDCl$_3$) δ 6.05-6.09 (m, 2H), 5.91 (d, 1H), 4.79 (d, 1H), 4.62 (d, 1H), 4.43 (d, 1H), 4.04-4.09 (m, 2H), 3.72 (d, 1H), 3.06 (d, 1H), 2.73 (dd, 1H), 2.62 (d, 1H), 2.44 (m, 1H), 2.16-2.22 (m, 3H), 1.94 (m, 3H), 1.85-1.89 (m, 6H), 1.56 (m, 2H), 1.24-1.28 (m, 17H), 1.22 (s, 3H), 1.07 (s, 3H), 0.97 (d, 3H), 0.88 (t, 3H).

Example 16 Preparation of 3-O-angeloyl-13-O-butanoyl-ingenol (Compound 16)

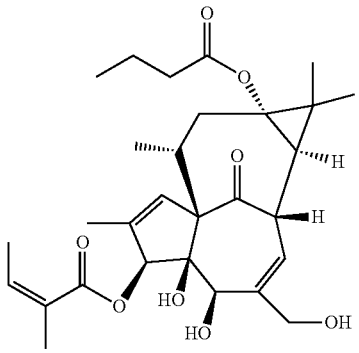 [SMILES: C/C=C(/C)C(=O)O[C@H]1C(C)=C[C@]23C(=O)[C@@H](C=C(CO)[C@@H](O)[C@]12O)[C@@H]1C(C)(C)[C@]1(OC(=O)CCC)C[C@H]3C]

Using 13-O-n-butanoyl-ingenol (Compound 5, for which the preparation method may refer to Example 5) as raw material, acetonide protection reaction, esterification reaction, and the reaction of removing acetonide-protecting group were carried out in sequence according to the synthesis method in Example 8 to obtain the title Compound (Compound 16).

$^1$H-NMR (400 MHz, CDCl$_3$) δ 6.15 (dq, 1H), 6.00-6.03 (m, 2H), 5.55 (s, 1H), 4.56 (brs, 1H), 4.05-4.17 (m, 4H), 3.61 (s, 1H), 2.61-2.76 (m, 3H), 2.14-2.23 (m, 3H), 1.99 (dd, 3H), 1.89 (t, 3H), 1.79 (d, 3H), 1.58 (m, 2H), 1.22 (d, 1H), 1.18 (s, 3H), 1.05 (s, 3H), 0.96 (d, 3H), 0.91 (t, 3H).

Example 17 Preparation of 3-O-angeloyl-13-O-hexanoyl-ingenol (Compound 17)

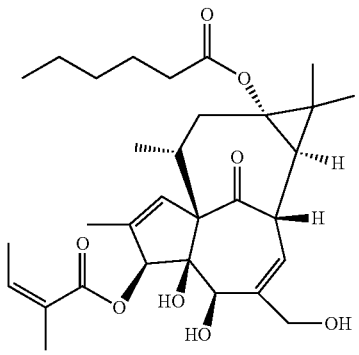 [SMILES: C/C=C(/C)C(=O)O[C@H]1C(C)=C[C@]23C(=O)[C@@H](C=C(CO)[C@@H](O)[C@]12O)[C@@H]1C(C)(C)[C@]1(OC(=O)CCCCC)C[C@H]3C]

Using 13-O-n-hexanoyl-ingenol (Compound 6, for which the preparation method may refer to Example 6) as raw material, acetonide protection reaction, esterification reaction, and the reaction of removing acetonide-protecting group were carried out in sequence according to the synthesis method in Example 8 to obtain the title Compound (Compound 17).

$^1$H-NMR (400 MHz, CDCl$_3$) δ 6.15 (dq, 1H), 5.98-6.03 (m, 2H), 5.55 (s, 1H), 4.59 (brs, 1H), 4.05-4.18 (m, 4H), 3.62 (s, 1H), 2.59-2.75 (m, 2H), 2.14-2.23 (m, 3H), 1.99 (dd, 3H), 1.89 (t, 3H), 1.80 (s, 3H), 1.55 (m, 2H), 1.19-1.31 (m, 5H), 1.17 (s, 3H), 1.05 (s, 3H), 0.96 (d, 3H), 0.86 (t, 3H).

Example 18 Preparation of 3-O-angeloyl-13-O-octanoyl-ingenol (Compound 18)

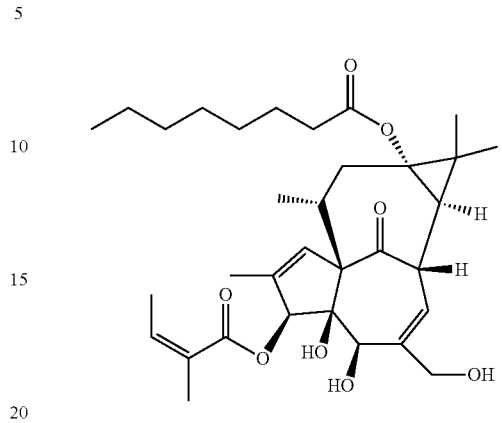

Using 13-O-n-octanoyl-ingenol (Compound 7, for which the preparation method may refer to Example 7) as raw material, acetonide protection reaction, esterification reaction, and the reaction of removing acetonide-protecting group were carried out in sequence according to the synthesis method in Example 8 to obtain the title Compound (Compound 18).

$^1$H-NMR (400 MHz, CDCl$_3$) δ 6.15 (dq, 1H), 5.98-6.05 (m, 2H), 5.54 (s, 1H), 4.53 (brs, 1H), 4.05-4.19 (m, 4H), 3.60 (s, 1H), 2.58-2.74 (m, 3H), 2.14-2.23 (m, 3H), 1.99 (dd, 3H), 1.90 (t, 3H), 1.80 (s, 3H), 1.54 (m, 2H), 1.20-1.31 (m, 9H), 1.18 (s, 3H), 1.05 (s, 3H), 0.96 (d, 3H), 0.86 (t, 3H).

Example 19 Preparation of 3-O-angeloyl-13-O-decanoyl-ingenol (Compound 19)

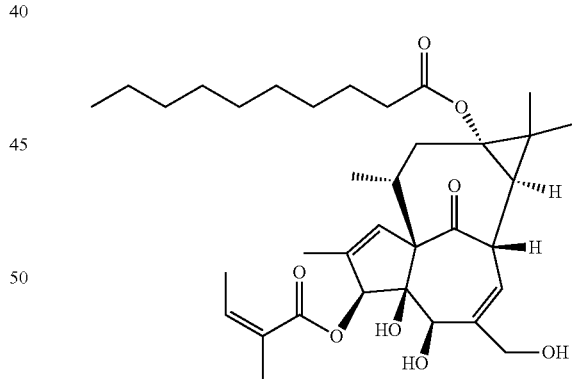

Using 13-O-decanoyl-ingenol (Compound 1a, for which the preparation method may refer to Example 1) as raw material, acetonide protection reaction, esterification reaction, and the reaction of removing acetonide-protecting group were carried out in sequence according to the synthesis method in Example 8 to obtain the title Compound (Compound 19).

$^1$H-NMR (400 MHz, CDCl$_3$) δ 6.14 (q, 1H), 6.00 (brs, 2H), 5.55 (s, 1H), 4.60 (brs, 1H), 4.03-4.19 (m, 4H), 3.63 (s, 1H), 2.58-2.76 (m, 3H), 2.13-2.24 (m, 3H), 1.99 (d, 3H), 1.89 (brs, 3H), 1.79 (s, 3H), 1.54 (m, 2H), 1.19-1.28 (m, 13H), 1.17 (s, 3H), 1.05 (s, 3H), 0.95 (d, 3H), 0.86 (t, 3H).

Example 20 Preparation of 3-O-tigloyl-13-O-dodecanoyl-ingenol (Compound 20)

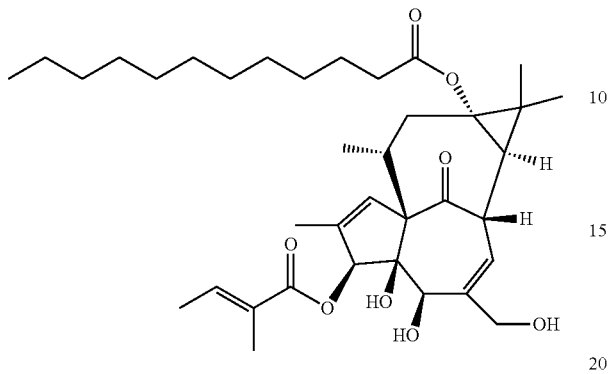

Using Compound 13-O-dodecanoyl-ingenol (Compound 1c, for which the preparation method may refer to Example 1) as a starting material, according to the synthesis method in Example 8, 13-O-dodecanoyl-ingenol 5,20-acetonide was synthesized, and then angelic anhydride was replaced with tiglic anhydride to synthesize 3-O-tigloyl-13-O-dodecanoyl-ingenol 5,20-acetonide, and the reaction of removing acetonide-protecting group were carried out to obtain the title Compound (Compound 20).

$^1$H-NMR (400 MHz, CDCl$_3$) δ 6.87 (q, 1H), 6.00 (s, 2H), 5.52 (s, 1H), 4.65 (m, 1H), 4.00-4.18 (m, 4H), 3.61 (s, 1H), 2.96 (m, 1H), 2.71 (dd, 1H), 2.61 (m, 1H), 2.11-2.23 (m, 3H), 1.83 (s, 3H), 1.81 (d, 3H), 1.77 (s, 3H), 1.54 (m, 2H), 1.19-1.33 (m, 17H), 1.16 (s, 3H), 1.04 (s, 3H), 0.97 (d, 3H), 0.86 (t, 3H).

Example 21 Preparation of 3-O-(2,3-dimethyl-butenoyl)-13-O-dodecanoyl-ingenol (Compound 21)

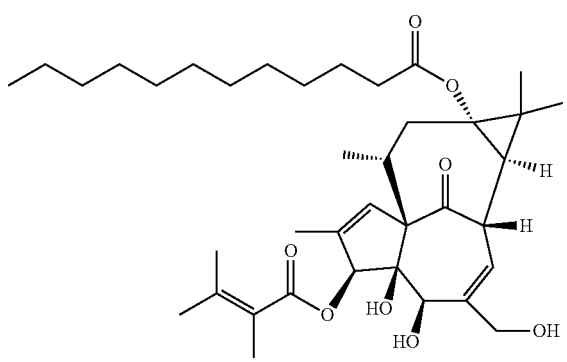 [SMILES: CCCCCCCCCCCC(=O)O[C@@]12C[C@@H](C)[C@]34C=C(C)[C@H](OC(=O)C(C)=C(C)C)[C@@]3(O)[C@H](O)C(CO)=C[C@H](C4=O)[C@@H]1C2(C)C]

Using Compound 13-O-dodecanoyl-ingenol (Compound 1c, for which the preparation method may refer to Example 1) as a starting material, according to the synthesis method in Example 8, 13-O-dodecanoyl-ingenol 5,20-acetonide was synthesized, and then angelic anhydride was replaced with 2,3-dimethylbutenoyl chloride to synthesize 3-O-(2,3-dimethylbutenoyl)-13-O-dodecanoyl-ingenol 5,20-acetonide, and the reaction of removing acetonide-protecting group was carried out to obtain the title Compound (Compound 21).

$^1$H-NMR (400 MHz, CDCl$_3$) δ 5.96-6.05 (m, 2H), 5.50 (s, 1H), 4.50 (d, 1H), 4.02-4.18 (m, 4H), 3.60 (s, 1H), 2.56-2.78 (m, 2H), 2.15-2.24 (m, 3H), 2.04 (d, 3H), 1.86 (s, 3H), 1.84 (s, 3H), 1.79 (d, 3H), 1.54 (m, 2H), 1.19-1.32 (m, 17H), 1.18 (s, 3H), 1.05 (s, 3H), 0.96 (d, 3H), 0.87 (t, 3H).

Example 22 Preparation of 3-O-(3,5-diethylisoxazolyl-4-formyl)-13-O-dodecanoyl-ingenol (Compound 22)

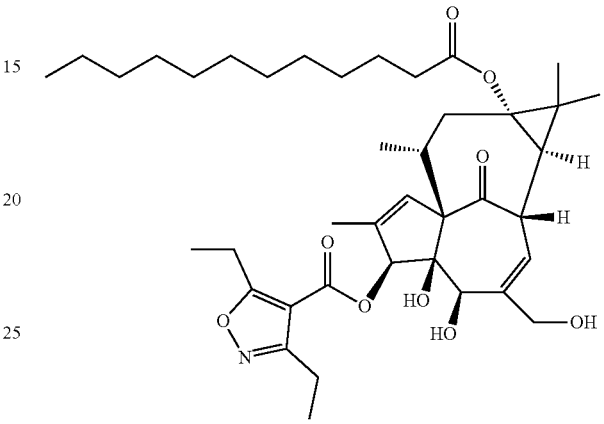

13-O-dodecanoyl-ingenol (Compound 1c, for which the preparation procedure may refer to Example 1) (0.5 mmol) was dissolved in 0.4 mg/mL of a solution of p-toluenesulfonic acid monohydrate in acetone and stirred at room temperature for 1 h. The reaction solution was concentrated to dryness under reduced pressure, re-dissolved in ethyl acetate, and washed with water and saturated aqueous sodium chloride solution, successively, and then the organic layer was concentrated to dryness under reduced pressure. The resulting residual was purified by flash chromatography (petroleum ether: ethyl acetate=4:1) to obtain 13-O-dodecanoyl-ingenol 5,20-acetonide (Compound 221).

Compound 221 (0.1 mmol) was dissolved in dichloromethane, and 3,5-diethylisoxazolyl-4-carboxylic acid (0.15 mmol), N,N'-dicyclohexylcarbodiimide (0.15 mmol), and 4-dimethylaminopyridine (0.15 mmol) were added in the condition of ice water bath, and stirred at 20° C. for 8 h. The reaction solution was poured into water and extracted with diethyl ether, The organic layer was washed with saturated aqueous sodium chloride solution, and then concentrated to dryness under reduced pressure. The resulting residual was purified by flash chromatography (petroleum ether:acetone=15:1) to obtain 3-O-(3,5-diethylisoxazolyl-4-formyl)-13-O-dodecanoyl-ingenol 5,20-acetonide (Compound 222).

Compound 222 (0.05 mmol) was dissolved in methanol, 4 M diluted hydrochloric acid was added and stirred at room temperature for 12 h. The reaction solution was poured into water and extracted with ethyl acetate. The organic layer was washed with saturated aqueous sodium chloride solution, and then concentrated to dryness under reduced pressure. The resulting residual was purified by flash chromatography (petroleum ether:acetone=2:1) to obtain the title compound (Compound 22).

$^1$H-NMR (400 MHz, CDCl$_3$) δ 6.10 (d, 1H), 6.03 (d, 1H), 5.69 (s, 1H), 4.07-4.22 (m, 4H), 3.78 (brs, 1H), 3.06 (dq, 2H), 2.85 (m, 2H), 2.58-2.74 (m, 2H), 2.26 (dd, 1H), 2.19 (t, 2H), 2.03 (s, 1H), 1.83 (s, 3H), 1.54 (m, 2H), 1.17-1.32 (m, 23H), 1.15 (s, 3H), 1.04 (s, 3H), 0.99 (d, 3H), 0.86 (t, 3H).

Example 23 Test of the Inhibitory Activity of Compounds of the Present Invention Against Proliferation of Tumor Cell Strains In this example, the inhibitory activity of compounds of the present invention against proliferation of seven human tumor cell lines and mouse B16-F10 melanoma cells was tested in vitro, and the $IC_{50}$ value (50% inhibitory concentration) of compounds against each tumor cell line was calculated.

The seven human tumor cell lines are: MCF-7 (human breast cancer cells), LOVO (human colon cancer cells), A549 (human lung cancer cells), BGC-823 (human gastric cancer cells), SMMC-7721 (human liver cancer cells), K562 (human leukemia cells), and HeLa (human cervical cancer cells).

(1) Test Method $IC_{50}$ values of the compounds for A549, BGC-823, LOVO, MCF-7, SMMC-7721, HeLa, and B16-F10 cells were tested. The above cells were routinely cultured in 1640 nutrient solution containing 10% calf serum, with passage for 1 time every 2 days, and the cells in logarithmic growth phase were taken for experiments. After the A549, BGC-823, LOVO, MCF-7, SMMC-7721, HeLa and B16-F10 cells in logarithmic growth phase were subjected to 0.25% trypsin digestion, they were blown into a single cell suspension, and then the cell concentration was adjusted to about $1\times10^5 \cdot mL^{-1}$ using RPMI 1640 solution containing 10% calf serum. The cells were seeded in a 96-well culture plate at 100 µL per well, and cultured for 24 hours until the cells were attached. K562 cells were taken and centrifuged and diluted into $2\times10^5 \cdot mL^{-1}$ single cell suspension with RPMI 1640 solution containing 10% calf serum, and inoculated into a 96-well culture plate at 100 µL per well.

100 µL of sample solution with different concentrations to be tested were added to the above 96-well plate, each concentration was added to 4 wells in parallel, and the cell control group was added with an equal volume of RPMI 1640 medium containing 10% calf serum to make a reaction volume of 200 µL. After incubating in an incubator at 37° C., 5% $CO_2$ for 72 h, 10 µL of 5 $mg \cdot mL^{-1}$ MTT solution was added to each well, and incubated at 37° C. for 4 h. The supernatant was carefully aspirated, 180 µL of DMSO was added to each well followed by shaking, and the absorbance (OD) value was measured at 570 nm on the microplate reader. The inhibition rate was calculated, and regression equation was established with the logarithmic value of the sample concentration and the inhibition rate (IR) to find the $IC_{50}$ value of the compound against the cells to be tested.

IR (%)=(1−OD value of the experimental group/OD value of the cell control group)×100%

(2) Test Results

The $IC_{50}$ values of compounds of the present invention for inhibition of proliferation of seven human tumor cell lines and mouse B16-F10 melanoma cells are shown in Table 1.

TABLE 1

$IC_{50}$ value of compound for inhibition of proliferation of tumor cell lines (µg/mL)

| Compound name and number | Cell line | | | | | | | |
|---|---|---|---|---|---|---|---|---|
| | A549 | BGC-823 | LOVO | K562 | SMMC-7721 | MCF-7 | HeLA | B16-F10 |
| 20-deoxy-13-O-dodecanoyl-ingenol (Compound 1d) | 26.8 | 15.4 | 19.2 | 6.88 | 31.5 | 29.2 | — | — |
| 13-O-decanoyl-ingenol (Compound 1a) | 15.1 | 15.0 | 9.77 | 0.70 | 19.5 | 13.8 | 29.1 | — |
| 13-O-(2'E,4'E-decadienoyl)-ingenol (Compound 1b) | 12.8 | 10.6 | 12.9 | 8.97 | 8.01 | 11.8 | — | — |
| 13-O-dodecanoyl-ingenol (Compound 1c) | 11.1 | 6.19 | 8.97 | 5.51 | 6.49 | 6.36 | 15.1 | — |
| 6,7-epoxy-20-deoxy-ingenol (Compound 1e) | >200 | >200 | >200 | 5.52 | >200 | >200 | — | — |
| 6,7-epoxy-20-O-(2,3-dimethylbutyryl)-13-O-dodecanoyl-ingenol (Compound 1f) | — | — | — | — | — | — | 16.8 | — |
| 13-O-n-octanoyl-ingenol (Compound 7) | 29.7 | 25.1 | 24.1 | 1.72 | 16.0 | 16.2 | 29.3 | 38.4 |
| 3-O-acetyl-13-O-dodecanoyl-ingenol (Compound 10) | 10.7 | 14.7 | 9.41 | 0.22 | 13.1 | 16.3 | 10.9 | 21.4 |
| 3-O-n-butanoyl-13-O-dodecanoyl-ingenol (Compound 11) | 14.3 | 13.4 | 8.82 | 0.10 | 19.1 | 18.5 | 20.3 | 26.2 |
| 20-O-acetyl-13-O-dodecanoyl-ingenol (Compound 12) | 16.0 | 10.3 | 6.71 | 0.06 | 12.7 | 12.7 | 32.3 | 14.0 |
| 20-O-n-butanoyl-13-O-dodecanoyl-ingenol (Compound 13) | 17.2 | 12.4 | 6.93 | 0.07 | 12.5 | 18.0 | 24.2 | 30.5 |
| 20-O-angeloyl-13-O-dodecanoyl-ingenol (Compound 15b) | 10.0 | 20.6 | 15.2 | 0.001 | 13.1 | 23.3 | 10.2 | 9.09 |
| 3,20-O-diangeloyl-13-O-dodeanoyl-ingenol (Compound 15a) | >100 | >100 | >100 | 3.22 | 26.9 | >100 | — | — |
| 13-O-dodecanoyl-ingenol 5,20-acetonide (Compound 2b) | 15.0 | 17.8 | 23.0 | 0.85 | 15.2 | 13.7 | — | — |
| 13-O-dodecanoyl-ingenol 3,4-acetonide (Compound 2c) | 9.59 | 5.30 | 10.3 | 0.42 | 8.21 | 8.89 | — | — |
| 3-O-angeloyl-13-O-acetyl-ingenol (Compound 8) | >50 | >100 | >50 | 0.0065 | 96.6 | >50 | >100 | — |
| 3-O-angeloyl-13-O-butanoyl-ingenol (Compound 16) | 46.8 | 44.1 | 36.9 | 4.21 | 43.5 | 38.4 | 61.1 | 17.0 |
| 3-O-angeloyl-13-O-hexanol-ingenol (Compound 17) | 21.7 | 21.7 | 16.9 | 2.93 | 21.1 | 18.6 | 18.6 | 6.50 |

TABLE 1-continued

IC$_{50}$ value of compound for inhibition of proliferation of tumor cell lines (μg/mL)

| Compound name and number | A549 | BGC-823 | LOVO | K562 | SMM C-7721 | MCF-7 | HeLA | B16-F10 |
|---|---|---|---|---|---|---|---|---|
| 3-O-angeloyl-13-O-octanoyl-ingenol (Compound 18) | 13.6 | 10.1 | 8.47 | 1.41 | 12.4 | 11.7 | 12.2 | 8.43 |
| 3-O-angeloyl-13-O-decanoyl-ingenol (Compound 19) | 12.6 | 14.0 | 7.90 | 2.13 | 13.4 | 9.30 | 8.58 | 9.85 |
| 3-O-tigloyl-13-O-dodecanoyl-ingenol (Compound 20) | 13.1 | 11.0 | 9.91 | 0.81 | 18.4 | 6.80 | 7.45 | 3.33 |
| 3-O-(2,3-dimethylbutenoyl)-13-O-dodecanoyl-ingenol (Compund 21) | 11.8 | 10.4 | 12.4 | 2.06 | 12.8 | 8.32 | 15.3 | 15.1 |
| 3-O-(3,5-diethylisoxazolyl-4-formyl)-13-O-dodecanoyl-ingenol (Compound 22) | 18.3 | 11.3 | 11.0 | 1.14 | 20.1 | 10.9 | 9.59 | 2.96 |
| 3-O-angeloyl-13-O-dodecanoyl-ingenol (Compound 9) | 10.8 | 0.85 | 10.1 | 1.87 | 8.86 | 10.1 | 12.5 | 10.4 |
| 3-O-(2,3-dimethylbutyryl)-13-O-dodecanol-ingenol | 11.0 | 10.4 | 7.60 | 0.12 | 14.5 | 9.05 | 24.3 | 17.8 |
| 3-O-trimethylacetyl-13-O-dodecanoyl-ingenol | 17.5 | 6.81 | 9.68 | <0.20 | 15.1 | 8.79 | 14.2 | 7.70 |
| 3-O-hexanoyl-13-O-dodecanoyl-ingenol | 18.5 | 18.3 | 16.5 | <0.20 | 16.1 | 14.0 | — | — |
| 20-O-(2,3-dimethylbutyryl)-13-O-dodecanoyl-ingenol | 8.89 | 11.0 | 8.36 | 0.64 | 10.7 | 10.1 | 14.5 | 16.6 |
| 3-O-angeloyl-ingenol | 31.2 | 43.5 | 33.4 | 0.0076 | 28.2 | 57.4 | 49.4 | 38.1 |

The results in Table 1 indicate that the derivative of 13-oxidized ingenol can exhibit inhibitory effect on the proliferation of various tumor cells, and some compounds exhibit selective inhibitory effect on leukemia cells.

Example 24 Effects of Compounds on the Neutrophil Oxidative Burst

This example investigated the effect of compound on neutrophil oxidative burst and calculated the efficiency of each compound in stimulating neutrophil oxidative burst.

(1) Test Method

Blood was taken from the abdominal aorta of rat. The neutrophilic granulocytes were isolated by the operational procedure of the rat peripheral blood neutrophil isolation kit. The neutrophilic granulocytes were re-suspended by Hanks, and were plated in a 96-well white plate at $1\times10^5$ cells/well, 80 μL/well; 1 mM of Luminol was added at 10 μL/well; 10 μL of the sample was added to each well, and the degree of oxidative burst was evaluated by chemiluminescence.

Calculation formula of Efficiency: Efficiency (%)= $(C_{sample}-C_{control})/C_{control}\times100\%$ (2) Test Results The efficiency of compounds in stimulating neutrophil oxidative burst is shown in Table 2.

TABLE 2

Efficiency of compounds in stimulating neutrophil oxidative burst

| | Efficiency (%) | |
|---|---|---|
| Compound name and number | 3 μg/mL | 0.1 μg/mL |
| 3-O-angeloy1-13-OH-ingenol (Compound 3) | 65.0 | — |
| 13-O-decanoyl-ingenol (Compound 1a) | 65.2 | — |
| 13-O-n-octanoyl-ingenol (Compound 7) | 45.0 | — |
| 20-O-(2,3-dimethylbutyryl)-13-O-decanoyl-ingenol (Compound 14) | 62.8 | — |
| 3-O-angeloy1-13-O-dodecanoyl-ingenol (Compound 9) | 77.0 | — |
| 3-O-n-butanoyl-13-O-dodecanoyl-ingenol (Compound 11) | 33.5 | — |
| 20-O-acetyl-13-O-dodecanoyl-ingenol (Compound 12) | 88.3 | — |
| 20-O-n-butanoyl-13-O-dodecanoyl-ingenol (Compound 13) | 62.4 | — |
| 13-O-dodecanoyl-ingenol 3,4-acetonide (Compound 2c) | 64.6 | — |
| 3-O-angeloyl-13-O-butanoyl-ingenol (Compound 16) | 80.1 | — |
| 3-O-angeloyl-13-O-hexanoyl-ingenol (Compound 17) | — | 82.1 |
| 3-O-angeloyl-13-O-octanoyl-ingenol (Compound 18) | — | 69.1 |
| 3-O-angeloyl-13-O-decanoyl-ingenol (Compound 19) | — | 43.5 |
| 3-O-tigloyl-13-O-dodecanoyl-ingenol (Compound 20) | 43.8 | — |
| 3-O-(2,3-dimethylbutenoyl)-13-O-dodecanoyl-ingenol (Compound 21) | 34.8 | — |
| 3-O-(3,5-diethylisoxazolyl-4-formyl)-13-O-dodecanoyl-ingenol (Compound 22) | — | 124 |
| 20-O-(2,3-dimethylbutyryl)-13-O-dodecanoyl-ingenol | 64.5 | — |
| 3-O-trimethylacetyl-13-O-dodecanoyl-ingenol | — | 205 |
| 3-O-acetyl-13-O-dodecanoyl-ingenol (Compound 10) | — | 111 |
| 20-O-angeloyl-13-O-dodecanoyl-ingenol (Compound 15b) | 360 | — |
| 13-O-n-hexanoyl-ingenol (Compound 6) | 52.2 | — |
| 3-O-(2,3-dimethylbutyryl)-13-O-dodecanoyl-ingenol | — | 71.4 |
| 3-O-hexanoyl-13-O-dodecanoyl-ingenol | — | 173 |
| 3-O-angeloyl-ingenol | 51.4 | — |

As can be seen from Table 2, the derivative of 13-oxidized ingenol has a stimulating effect on neutrophil oxidative burst, and the efficiency of most of the compounds is higher than that of 3-O-angeloyl-ingenol.

Example 25 Effect of Compounds on Release of IL-8 by Human Keratinocytes (HaCaT)

This Example investigated the effect of compound on release of IL-8 by human keratinocytes (HaCaT) and calculated the efficiency of each compound in stimulating the release of IL-8 by human keratinocytes (HaCaT).

(1) Test Method

Hacat cells were cultured in MEM+10% FBS under the conditions of 37° C., 5% $CO_2$, and when the cells reached 80-95% fusion, they were inoculated into a 96-well culture plate ($1\times10^4$ cells/well) at 100 μL/well, and incubated for 18-24 h. The supernatant was discarded and the cells were incubated for 3-6 h in 1% FBS medium. Different concentrations of the sample solution of compound to be tested were added to each well, and the cell control group was added with an equal volume of 1% FBS medium at 10 μL/well, and incubated for 24 h. The supernatant was taken and tested according to the operation sequence of the IL-8 Elisa kit.

Calculation formula of Efficiency: Efficiency (%)= $(C_{sample} - C_{control})/C_{control} \times 100\%$ (2) Test Results The efficiency of compound in stimulating the release of IL-8 by human keratinocytes (HaCaT) is shown in Table 3.

TABLE 3

Efficiency of compound in stimulating the release of IL-8 by HaCaT cells

| Compound name and number | Efficiency 1 μg/mL | Efficiency 0.1 μg/mL |
|---|---|---|
| 3-O-angeloyl-13-OH-ingenol (Compound 3) | 23.8 | — |
| 3-O-angeloyl-13-O-acetyl-ingenol (Compound 8) | 38.3 | — |
| 20-O-(2,3-dimethylbutyryl)-13-O-decanoyl-ingenol (Compound 14) | 22.6 | — |
| 3-O-angeloyl-13-O-dodecanoyl-ingenol (Compound 9) | 23.5 | — |
| 3-O-acetyl-13-O-dodecanoyl-ingenol (Compound 10) | — | 79.5 |
| 20-O-acetyl-13-O-dodecanoyl-ingenol (Compound 12) | 37.0 | — |
| 20-O-n-butanoyl-13-O-dodecanoyl-ingenol (Compound 13) | — | 30.3 |
| 3-O-angeloyl-13-O-butanoyl-ingenol (Compound 16) | — | 84.6 |
| 3-O-angeloyl-13-O-hexanoyl-ingenol (Compound 17) | — | 121 |
| 3-O-angeloyl-13-O-octanoyl-ingenol (Compound 18) | — | 29.8 |
| 3-O-angeloyl-13-O-decanoyl-ingenol (Compound 19) | — | 144 |
| 3-O-tigloyl-13-O-dodecanoyl-ingenol (Compound 20) | — | 109 |
| 3-O-(2,3-dimethylbutenoyl)-13-O-dodecanoyl-ingenol (Compound 21) | — | 127 |
| 3-O-(3,5-diethylisoxazolyl-4-formyl)-13-O-dodecanoyl-ingenol (Compound 22) | — | 144 |
| 3-O-trimethylacetyl-13-O-dodecanoyl-ingenol | — | 83.7 |
| 3-O-(2,3-dimethylbutyryl)-13-O-dodecanoyl-ingenol | — | 50 |
| 3-O-hexanoyl-13-O-dodecanoyl-ingenol | — | 66.0 |
| 3-O-angeloyl-ingenol | 41.4 | 31.9 |

As can be seen from Table 3, the derivative of 13-oxidized ingenol has a stimulating effect on release of IL-8 by HaCaT cells, and the efficiency is comparable to that of 3-O-angeloyl-ingenol, or higher than 3-O-angeloyl-ingenol.

Example 26 Evaluation of Antitumor Activity of Compounds in B16-F0 Mouse Melanoma Model This Example investigated the antitumor activity of compounds in B16-F0 mouse melanoma model.

(1) Test Method

In vitro passage of B16-F0 tumor source was inoculated subcutaneously into female C57BL/6J mice, and passage was carried out after tumor formation. After passage, the subcutaneous tumor tissue of the tumor-bearing mice was taken and ground with 3 times amount of physiological saline to form a tumor cell suspension, and 0.2 mL/mouse of which was inoculated subcutaneously into the axilla of forelimb of mice, which were used as the tumor-source mice. Female C57BL/6J mice were taken and their hair in an area of 4 $cm^2$ on the neck and back was shaven. After anesthesia with diethyl ether, B16 tumor source was inoculated intradermally at 0.05 mL/mouse. After 3 days of inoculation, the skin was continuously administered for 3 days, once per day, 20 μL/mouse each time, and in the test, a solvent group as a negative control group was included. On the 19th day of the experiment, the experiment was terminated. After the mice were euthanized, the intradermally transplanted tumors were completely separated and excised, and the tumor was weighed to calculate the tumor inhibition rate.

Calculation formula of tumor inhibition rate: tumor inhibition rate (%)=$(W_{model\ group} - W_{administration\ group})/W_{model\ group} \times 100\%$ The tumor growths of the experimental group and the solvent control group were compared to evaluate the antitumor activity of each compound, and the compound with $P<0.05$ was considered to be effective. The tumor inhibition rate of the compounds is shown in Table 4.

TABLE 4

Tumor inhibition rate of compounds in B16-F0 mouse melanoma model

| Compound name and number | Tumor-inhibition rate |
|---|---|
| 3-O-angeloyl-13-O-acetyl-ingenol (Compound 8) | 90.3% |
| 3-O-angeloyl-13-O-butanoyl-ingenol (Compound 16) | 89.6% |
| 3-O-angeloyl-13-O-hexanoyl-ingenol (Compound 17) | 68.8% |
| 3-O-angeloyl-13-O-octanoyl-ingenol (Compound 18) | 59.0% |
| 3-O-angeloyl-13-O-decanoyl-ingenol (Compound 19) | 65.7% |
| 3-O-(3,5-diethylisoxazolyl-4-formyl)-13-O-dodecanoyl-ingenol (Compound 22) | 39.5% |
| 3-O-angeloyl-13-O-dodecanoyl-ingenol (Compound 9) | 71.8% |
| 3-O-(2,3-dimethylbutenoyl)-13-O-dodecanoyl-ingenol (Compound 21) | 64.1% |
| 3-O-trimethylacetyl-13-O-dodecanoyl-ingenol | 47.4% |
| 20-O-acetyl-13-O-dodecanoyl-ingenol | 40.7% |

Although specific embodiments of the invention have been described in detail, those skilled in the art will understand that: according to all teachings that have been disclosed, various modifications and substitutions can be made to those details, all of which are within the protection scope of the present invention. The full scope of the present invention is given by the appended claims and any equivalents thereof.

The invention claimed is:

1. A compound of Formula (I), or a pharmaceutically acceptable salt, solvate, prodrug, metabolite or crystal form thereof:

(I)

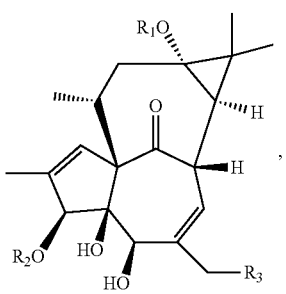

wherein:
R₁ is selected from the group consisting of hydrogen and M-C(O)—, wherein M is selected from the group consisting of hydrogen, 1,3-nonadienyl, C₁-C₄ linear alkyl, C₁-C₄ branched alkyl, C₄-C₉ linear alkyl, C₄-C₉ branched alkyl, n-decyl, and n-undecyl; R₂ is Q-C(O)—, wherein Q is selected from the group consisting of methyl, n-propyl,

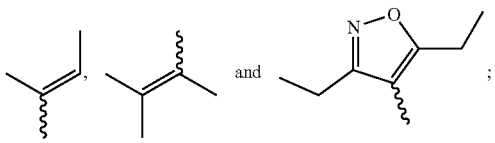

and R₃ is selected from the group consisting of hydrogen, hydroxyl and X—C(O)—O—, wherein X is selected from the group consisting of methyl, n-propyl, n-pentyl, t-butyl,

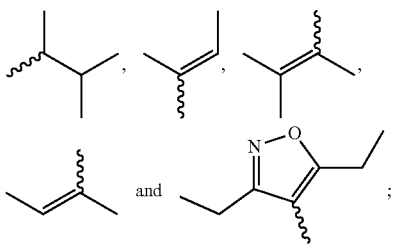

or R₁ is M-C(O)—, wherein M is selected from the group consisting of C₁-C₉ linear or branched alkyl and C₂-C₁₁ linear or branched alkenyl containing 1 or 2 carbon-carbon double bonds; R₂ is selected from the group consisting of hydrogen and Q-C(O)—, wherein Q is selected from the group consisting of methyl, n-propyl, t-butyl,

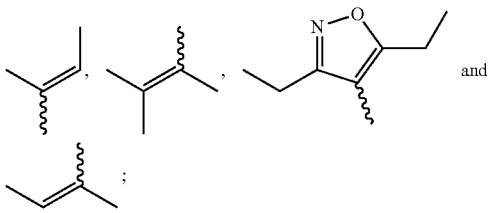

and R₃ is selected from the group consisting of hydrogen and hydroxyl;

or R₁ is M-C(O)—, and M is n-undecyl; R₂ is Q-C(O)—, wherein Q is

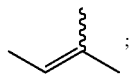

and R₃ is selected from the group consisting of hydrogen and X—C(O)—O—, wherein X is selected from the group consisting of methyl, n-propyl,

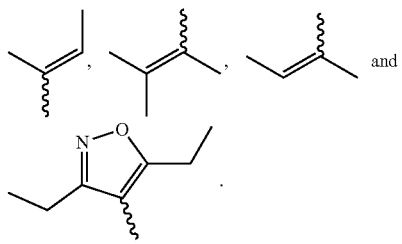

2. A compound of Formula (I), or a pharmaceutically acceptable salt, solvate, prodrug, metabolite or crystal form thereof:

(I)

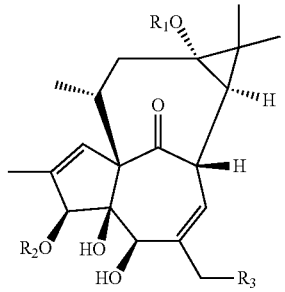

wherein:
R₁ is selected from the group consisting of hydrogen and M-C(O)—, wherein M is selected from the group consisting of methyl, n-propyl, n-pentyl, n-heptyl, n-nonyl, 1,3-nondienyl and 1,3,5-nontrienyl;
R₂ is selected from the group consisting of hydrogen and Q-C(O)—, wherein Q is selected from the group consisting of methyl, n-propyl, n-pentyl, t-butyl,

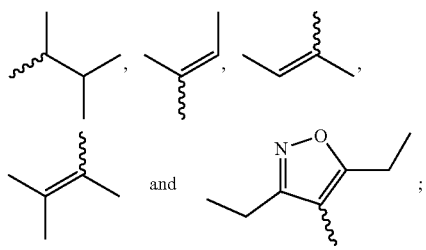

R₃ is selected from the group consisting of hydrogen and X—C(O)—O—, wherein X is selected from the group consisting of methyl, n-propyl, t-butyl, n-pentyl,

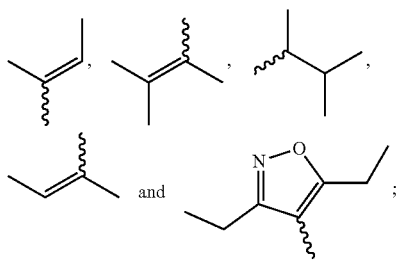

and, when R₁ is M-C(O)—, M is methyl or 1,3,5-nontrienyl, R₃ is X—C(O)—O— and X is

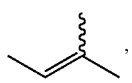

R₂ is not hydrogen;

when R₁ is M-C(O)—, M is n-nonyl and R₃ is CH₃—C(O)—O—, R₂ is not

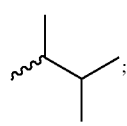

when R₁ is hydrogen and R₃ is (CH₃)₃C—C(O)—O—, R₂ is not hydrogen or (CH₃)₃C—C(O)—.

3. The compound of claim 1, or a pharmaceutically acceptable salt, solvate, prodrug, metabolite or crystal form thereof, wherein, R₁ is M-C(O)—, and M is n-undecyl; R₂ is Q-C(O)—, wherein Q is selected from the group consisting of methyl, n-propyl,

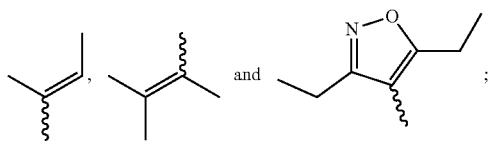

R₃ is selected from the group consisting of hydrogen, hydroxyl and X—C(O)—O—, wherein X is selected from the group consisting of methyl, n-propyl, t-butyl,

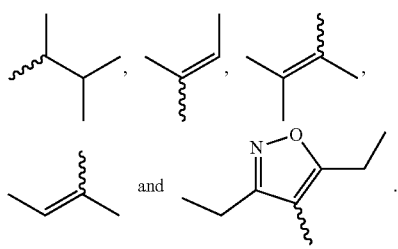

4. A compound of Formula (I), or a pharmaceutically acceptable salt, solvate, prodrug, metabolite or crystal form thereof:

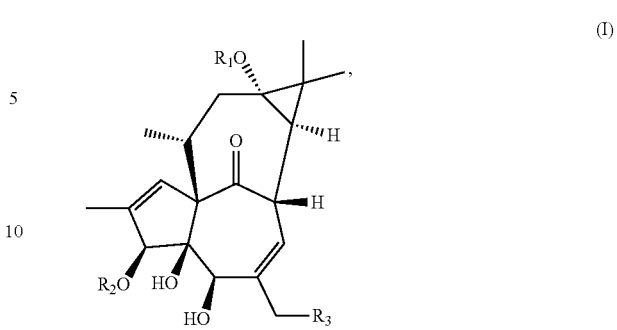

wherein:

R₁ is M-C(O)—, and M is n-undecyl;

R₂ is hydrogen;

R₃ is X—C(O)—O—, wherein, X is selected from the group consisting of methyl, n-propyl,

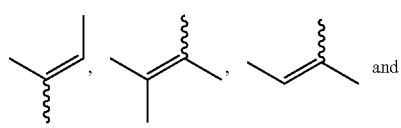

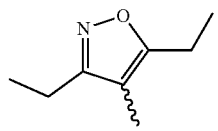

5. The compound of claim 1, or a pharmaceutically acceptable salt, solvate, prodrug, metabolite or crystal form thereof, wherein, R₁ is M-C(O)—, and M is n-undecyl; R₂ is Q-C(O)—, wherein Q is

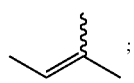

R₃ is X—C(O)—O—, wherein, X is selected from the group consisting of methyl, n-propyl,

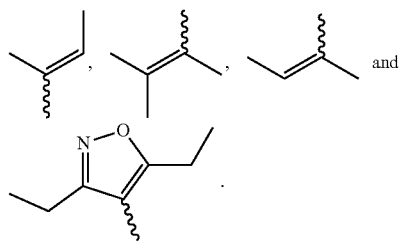

6. A compound or a pharmaceutically acceptable salt, solvate, prodrug, metabolite or crystal form thereof, wherein the compound is one of the following:

| Name of Compounds | Structure of Compounds |
|---|---|
| 13-O-decanoyl-ingenol | 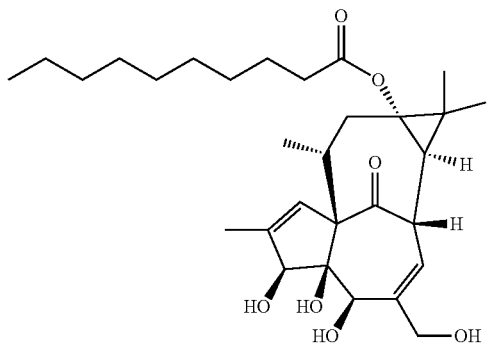 [SMILES: CCCCCCCCCC(=O)O[C@@]12C[C@@H](C)[C@]34C=C(C)[C@H](O)[C@@]3(O)[C@H](O)C(CO)=C[C@H](C4=O)[C@@H]1C2(C)C] |
| 13-O-(2'E,4'-E-decadienoyl)-ingenol | 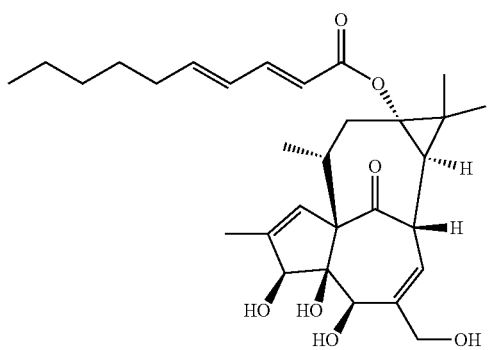 [SMILES: CCCCC/C=C/C=C/C(=O)O[C@@]12C[C@@H](C)[C@]34C=C(C)[C@H](O)[C@@]3(O)[C@H](O)C(CO)=C[C@H](C4=O)[C@@H]1C2(C)C] |
| 20-deoxy-13-O-dodecanoyl-ingenol | 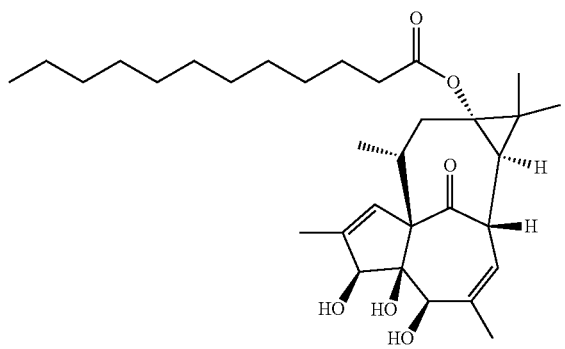 [SMILES: CCCCCCCCCCCC(=O)O[C@@]12C[C@@H](C)[C@]34C=C(C)[C@H](O)[C@@]3(O)[C@H](O)C(C)=C[C@H](C4=O)[C@@H]1C2(C)C] |
| 6,7-epoxy-20-deoxy-ingenol | 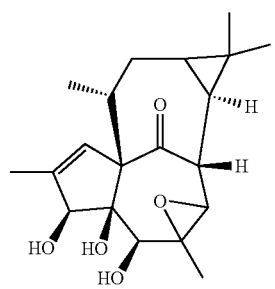 |

| Name of Compounds | Structure of Compounds |
|---|---|
| 6,7-epoxy-20-O-(2,3-dimethylbutyryl)-13-O-dodecanoyl-ingenol | |
| 3-O-angeloyl-13-hydroxy-ingenol | |
| 13-O-acetyl-ingenol | |
| 13-O-n-butanoyl-ingenol | |

| Name of Compounds | Structure of Compounds |
|---|---|
| 13-O-n-hexanoyl-ingenol | |
| 13-O-n-octanoyl-ingenol | |
| 3-O-angeloyl-13-O-acetyl-ingenol | |
| 3-O-acetyl-13-O-dodecanoyl-ingenol | |

| Name of Compounds | Structure of Compounds |
|---|---|
| 3-O-n-butanoyl-13-O-dodecanoyl-ingenol | 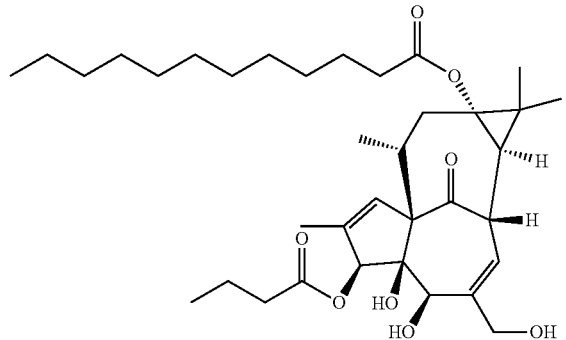 [SMILES: CCCCCCCCCCCC(=O)O[C@@]12C[C@@H](C)[C@]34C=C(C)[C@H](OC(=O)CCC)[C@@]3(O)[C@H](O)C(CO)=C[C@H](C4=O)[C@@H]1C2(C)C] |
| 20-O-acetyl-13-O-dodecanoyl-ingenol | 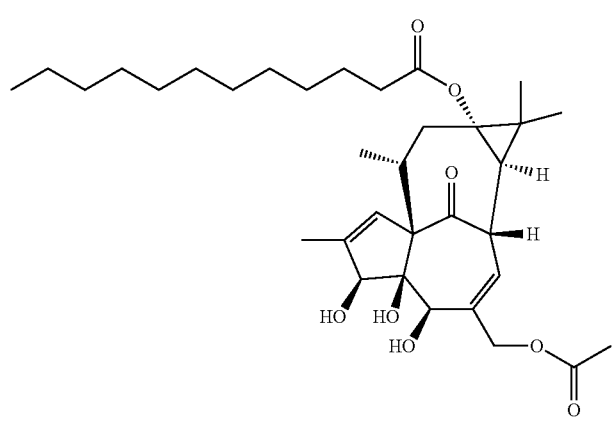 [SMILES: CCCCCCCCCCCC(=O)O[C@@]12C[C@@H](C)[C@]34C=C(C)[C@H](O)[C@@]3(O)[C@H](O)C(COC(C)=O)=C[C@H](C4=O)[C@@H]1C2(C)C] |
| 20-O-n-butanoyl-13-O-dodecanoyl-ingenol | 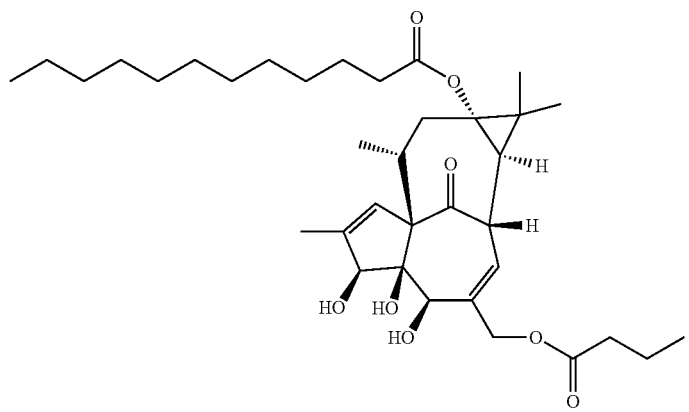 |
| 20-O-(2,3-dimethylbutyryl)-13-O-dodecanoyl-ingenol | 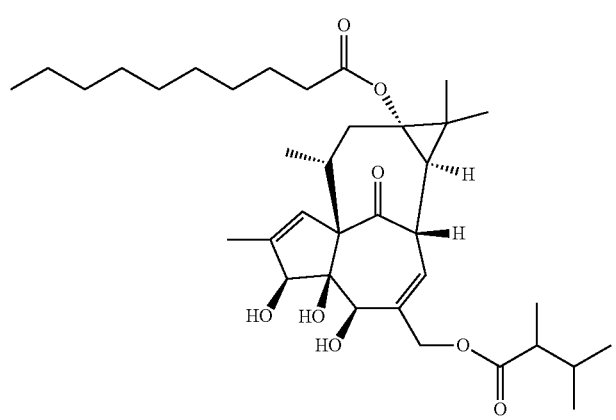 |

| Name of Compounds | Structure of Compounds |
|---|---|
| 20-O-angeloyl-13-O-dodecanoyl-ingenol | |
| 3,20-O-diangeloyl-13-O-dodecanoyl-ingenol | |
| 3-O-angeloyl-13-O-hexanoyl-ingenol | |
| 3-O-angeloyl-13-O-hexaoyl-ingenol | |

| Name of Compounds | Structure of Compounds |
| --- | --- |
| 3-O-angeloyl-13-O-octanoyl-ingenol | |
| 3-O-angeloyl-13-O-decanoyl-ingenol | |
| 3-O-(2,3-dimethylbutenoyl)-13-O-dodecanoyl-ingenol | |
| 3-O-(3,5-diethylisoxazolyl-4-formyl)-13-O-dodecanoyl-ingenol | |

-continued
| Name of Compounds | Structure of Compounds |
|---|---|
| 20-O-tigloyl-13-O-dodecanoyl-ingenol | 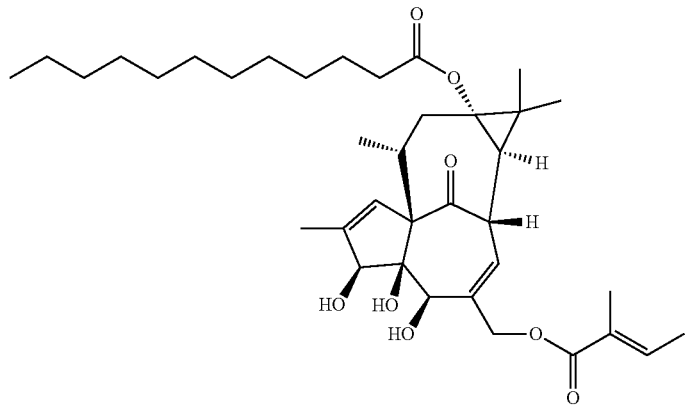 [SMILES: C/C=C(\C)C(=O)OCC1=C[C@@H]2C(=O)[C@]3(C=C(C)[C@H](O)[C@@]3(O)[C@@H]1O)[C@H](C)C[C@]1(OC(=O)CCCCCCCCCCC)[C@H]2C1(C)C] |
| 3-O-tigloyl-13-O-dodecanoyl-ingenol | 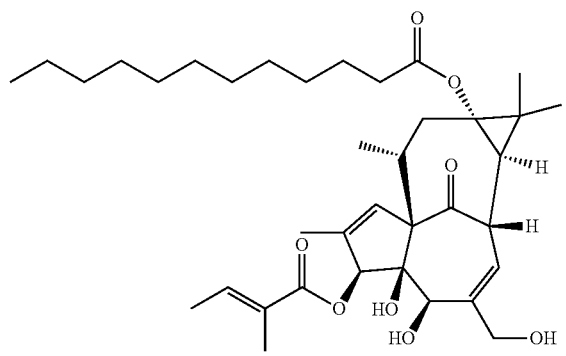 [SMILES: C/C=C(\C)C(=O)O[C@H]1C(C)=C[C@]23C(=O)[C@@H](C=C(CO)[C@@H](O)[C@]12O)[C@@H]1C(C)(C)[C@]1(OC(=O)CCCCCCCCCCC)C[C@H]3C] |
| 20-O-(2,3-dimethylbutenoyl)-13-O-dodecanoyl-ingenol | 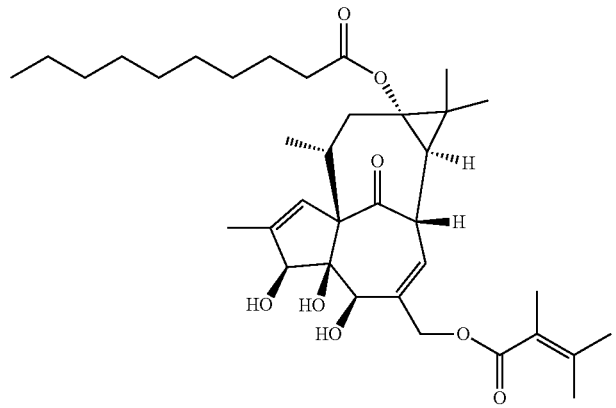 |

7. A compound of Formula (II), or a pharmaceutically acceptable salt, solvate, prodrug, metabolite or crystal form thereof:

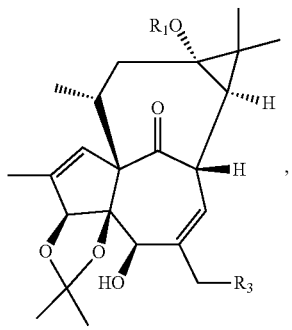

(II)

wherein:
R₁ is selected from the group consisting of hydrogen and M-C(O)—, wherein M is selected from the group consisting of hydrogen, 1,3-nonadienyl, $C_1$-$C_4$ linear alkyl, $C_1$-$C_4$ branched alkyl, $C_4$-$C_9$ linear alkyl, $C_4$-$C_9$ branched alkyl, n-decyl, and n-undecyl; and R₃ is selected from the group consisting of hydrogen, hydroxyl, and X—C(O)—O—, wherein X is selected from the group consisting of methyl, n-propyl, n-pentyl, t-butyl,

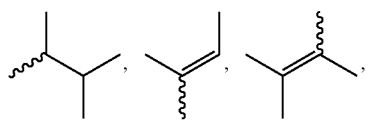

or R₁ is M-C(O)—, wherein M is selected from the group consisting of $C_1$-$C_9$ linear or branched alkyl and $C_2$-$C_{11}$ linear or branched alkenyl containing 1 or 2 carbon-carbon double bonds; and R₃ is selected from the group consisting of hydrogen and hydroxyl;

or R₁ is M-C(O)—, and M is n-undecyl; and R₃ is selected from the group consisting of hydrogen and X—C(O)—O—, wherein X is selected from the group consisting of methyl, n-propyl,

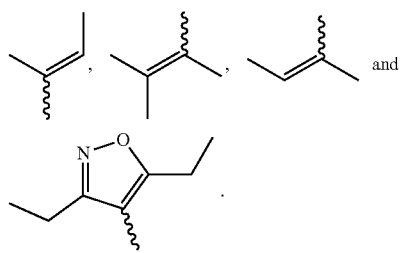

8. A pharmaceutical composition comprising the compound or the pharmaceutically acceptable salt, solvate, prodrug, metabolite or crystal form of claim 1, and a pharmaceutically acceptable carrier.

* * * * *